US 8,138,119 B2

(12) United States Patent
Fischer et al.

(10) Patent No.: US 8,138,119 B2
(45) Date of Patent: Mar. 20, 2012

(54) ALKOXYALKYL SPIROCYCLIC TETRAMIC ACIDS AND TETRONIC ACIDS

(75) Inventors: Reiner Fischer, Monheim (DE); Oliver Gaertzen, Köln (DE); Stefan Lehr, Liederbach (DE); Dieter Feucht, Eschborn (DE); Olga Malsam, Rösrath (DE); Mark Wilhelm Drewes, Langenfeld (DE); Eva-Maria Franken, Leichlingen (DE); Christian Arnold, Langenfeld (DE); Thomas Auler, Leichlingen (DE); Martin Jeffrey Hills, Idstein (DE); Heinz Kehne, Hofheim (DE); Chris Hugh Rosinger, Hofheim (DE); Thomas Bretschneider, Lohmar (DE); Guido Bojack, Wiesbaden-Naurod (DE); Jan Dittgen, Frankfurt (DE)

(73) Assignee: Bayer Cropscience AG, Monheim (DE)

( * ) Notice: Subject to any disclaimer, the term of this patent is extended or adjusted under 35 U.S.C. 154(b) by 625 days.

(21) Appl. No.: 12/083,691

(22) PCT Filed: Oct. 20, 2006

(86) PCT No.: PCT/EP2006/010130
§ 371 (c)(1),
(2), (4) Date: May 4, 2009

(87) PCT Pub. No.: WO2007/048545
PCT Pub. Date: May 3, 2007

(65) Prior Publication Data
US 2009/0215624 A1    Aug. 27, 2009

(30) Foreign Application Priority Data

Oct. 27, 2005   (DE) .................. 10 2005 051 325

(51) Int. Cl.
| A01N 25/32 | (2006.01) |
| A01N 43/38 | (2006.01) |
| A01N 43/08 | (2006.01) |
| A01N 43/56 | (2006.01) |
| A01N 43/80 | (2006.01) |
| C07D 209/54 | (2006.01) |
| C07D 307/94 | (2006.01) |
| C07D 231/06 | (2006.01) |
| C07D 261/02 | (2006.01) |

(52) U.S. Cl. ........ 504/106; 504/138; 504/140; 504/139; 514/409; 514/462; 514/403; 514/378; 549/240; 548/408; 548/379; 548/240

(58) Field of Classification Search .................. None
See application file for complete search history.

(56) References Cited

U.S. PATENT DOCUMENTS

| 4,021,224 A | 5/1977 | Pallos et al. |
| 4,186,130 A | 1/1980 | Teach |
| 4,623,727 A | 11/1986 | Hübele |
| 4,639,266 A | 1/1987 | Heubach et al. |
| 4,881,966 A | 11/1989 | Nyffeler et al. |
| 4,891,057 A | 1/1990 | Sohn et al. |
| 4,902,340 A | 2/1990 | Hubele |
| 5,258,527 A | 11/1993 | Krauskopf et al. |
| 5,262,383 A | 11/1993 | Fischer et al. |
| 5,314,863 A | 5/1994 | Löher et al. |
| 5,380,852 A | 1/1995 | Schütze et al. |
| 5,401,700 A | 3/1995 | Sohn et al. |
| 5,407,897 A | 4/1995 | Cary et al. |
| 5,462,913 A | 10/1995 | Fischer et al. |
| 5,504,057 A | 4/1996 | Fischer et al. |
| 5,508,436 A | 4/1996 | Fischer et al. |
| 5,516,750 A | 5/1996 | Willms et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,700,758 A | 12/1997 | Rösch et al. |
| 5,739,079 A | 4/1998 | Holdgrün et al. |

(Continued)

FOREIGN PATENT DOCUMENTS

CA    2 492 096 A1    1/2004

(Continued)

OTHER PUBLICATIONS

Oldfield et al., Journal of Medicinal Chemistry (1965), vol. 8(2), p. 239-249.*

(Continued)

*Primary Examiner* — Yong Chu
(74) *Attorney, Agent, or Firm* — Sterne, Kessler, Goldstein & Fox PLLC

(57) ABSTRACT

The invention relates to novel alkoxyalkyl spirocyclic tetramic and tetronic acids of the formula (I), in which
A, B, D, $Q^1$, $Q^2$, $Q^3$, $Q^4$, G, W, X, Y and Z are as defined above,
to a plurality of processes and intermediates for their preparation and to their use as pesticides and/or herbicides and/or microbicides, and also to selective herbicidal compositions comprising, firstly, the alkoxyalkyl spirocyclic tetramic and tetronic acids and, secondly, at least one crop plant compatibility-improving compound.

27 Claims, No Drawings

U.S. PATENT DOCUMENTS

| | | | |
|---|---|---|---|
| 5,830,825 | A | 11/1998 | Fischer et al. |
| 5,830,826 | A | 11/1998 | Fischer et al. |
| 5,981,567 | A | 11/1999 | Fischer et al. |
| 6,114,374 | A | 9/2000 | Lieb et al. |
| 6,140,358 | A | 10/2000 | Lieb et al. |
| 6,200,932 | B1 | 3/2001 | Fischer et al. |
| 6,235,680 | B1 | 5/2001 | Ziemer et al. |
| 6,251,827 | B1 | 6/2001 | Ziemer et al. |
| 6,251,830 | B1 | 6/2001 | Fischer et al. |
| 6,288,102 | B1 | 9/2001 | Hagemann et al. |
| 6,316,486 | B1 | 11/2001 | Lieb et al. |
| 6,358,887 | B1 | 3/2002 | Fischer et al. |
| 6,417,370 | B1 | 7/2002 | Lieb et al. |
| 6,451,843 | B1 | 9/2002 | Lieb et al. |
| 6,458,965 | B1 | 10/2002 | Lieb et al. |
| 6,472,419 | B1 | 10/2002 | Fischer et al. |
| 6,511,940 | B1 | 1/2003 | Ziemer et al. |
| 6,511,942 | B1 | 1/2003 | Lieb et al. |
| 6,589,976 | B1 | 7/2003 | Fischer et al. |
| 6,608,211 | B1 | 8/2003 | Hagemann et al. |
| 6,861,391 | B1 | 3/2005 | Fischer et al. |
| 6,894,005 | B1 | 5/2005 | Maetzke et al. |
| 2003/0216260 | A1 | 11/2003 | Ruther et al. |
| 2005/0054535 | A1 | 3/2005 | Fischer et al. |
| 2006/0160847 | A1 | 7/2006 | Fischer et al. |
| 2006/0166829 | A1 | 7/2006 | Fischer et al. |

FOREIGN PATENT DOCUMENTS

| | | |
|---|---|---|
| CA | 2 497 074 A1 | 3/2004 |
| CA | 2 518 620 A1 | 9/2004 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| CA | 2 552 737 A1 | 7/2005 |
| CA | 2 561 076 A1 | 10/2005 |
| CA | 2 572 141 A1 | 1/2006 |
| CA | 2 586 096 A1 | 6/2006 |
| CA | 2 595 602 A1 | 6/2006 |
| EP | 0 346 620 A1 | 12/1989 |
| WO | WO 2006/029799 A1 | 3/2006 |

OTHER PUBLICATIONS

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.* 6:341-345, Council of Scientific and Industrial Research (1968).

Chambers, M.S., et al., "An Asymmetric Synthesis of Thiotetronic Acids using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene," *J. Chem. Soc. Chem. Commun.*:1228-1230, Journal of Chemical Society (1987).

Ciufolini, M.A., and Byrne, N. E., "The Total Synthesis of Cystodytins," *J. Am. Chem. Soc.* 113:8016-8024, American Chemical Society (1991).

Compagnon, P.L., and Miocque, M., "Addition des Réactifs Nucléophiles sur la Triple Liaison Nitrile," *Ann. Chim.* 5:11-22, Masson (1970).

Edward, J.T., and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Etheredge, S.J., "Bicyclic Ketones by Intramolecular Alkylatons. A Reinvestigation," *J. Org. Chem.* 31:1990-1994, American Chemical Society (1966).

Harrison, H.R., et al., "Use of molecular sieves in the methyl esterification of carboxylic acids," *Chem. Ind.*, p. 1568, Society of Chemical Industry (1968).

Munday, L., "Amino-acids of the Cyclohexane Series. Part I.," *J. Chem. Soc.*, pp. 4372-4379, Royal Society of Chemistry (1961).

Sonntag, N.O.V., "The Reactions of Aliphatic Acid Chlorides," *Chem. Rev.* 52:237-416, American Chemical Society (1953).

Dialog File 351, Accession No. 4963457, Derwent WPI English language abstract for EP 0 346 620 A1 (listed as document FP1 on accompanying form PTO/SB/08A) (1989).

International Search Report for International Application No. PCT/EP2006/010130, European Patent Office, Netherlands, mailed on May 2, 2007.

\* cited by examiner

ALKOXYALKYL SPIROCYCLIC TETRAMIC ACIDS AND TETRONIC ACIDS

This application is a U.S. National Stage of International Application No. PCT/EP2006/010130, filed Oct. 20, 2006, which claims the benefit of German Patent Application No. 102005051325.5, filed Oct. 27, 2005. The entirety of each of these applications is incorporated by reference herein.

The present invention relates to novel alkoxyalkyl-substituted spirocyclic ketoenols, to a plurality of processes for their preparation and to their use as pesticides and/or microbicides and/or herbicides. The invention also provides selective herbicidal compositions comprising, firstly, alkoxyalkyl-substituted spirocyclic ketoenols and, secondly, a crop plant compatibility-improving compound.

1-H-Arylpyrrolidinedione derivatives having herbicidal, insecticidal or acaricidal action are known: EP-A456 063, EP-A-521 334, EP-A-613 884, EP-A-613 885, WO 95/01 358, WO 98/06 721, WO 98/25 928, WO 99/16 748, WO 99/24 437 or WO 01/17 972.

Also known are alkoxy-substituted spirocyclic 1H-arylpyrrolidinedione derivatives: EP-A-596 298, WO 95/26 954, WO 95/20 572, EP-A-0 668 267, WO 96/25 395, WO 96/35 664, WO 97/01 535, WO 97/02 243, WO 97/36 868, WO 98/05 638, WO 99/43 649, WO 99/48 869, WO 99/55 673, WO 01/23 354, WO 01/74 770, WO 01/17 972, WO 03/013 249, WO 04/02 4688, WO 04/065 366, WO 04/08 0962, WO 04/00 7448, WO 04/111 042, WO 05/044 791, WO 05/044 796, WO 05/048 710, WO 05/049 569, WO 05/066 125, WO 05/092 897, WO 06/000 355, WO 06/029 799, WO 06/056 281, WO 06/056 282.

It is known that certain $\Delta^3$-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799.

However, the herbicidal and/or acaricidal and/or insecticidal activity and/or the activity spectrum and/or the compatibility of the known compounds with plants, in particular with crop plants, is not always sufficient.

This invention now provides novel compounds of the formula (I)

(I)

in which

W represents hydrogen, alkyl, alkenyl, alkynyl, halogen, alkoxy, haloalkyl, haloalkoxy or cyano, X represents halogen, alkyl, alkenyl, alkynyl, alkoxy, alkoxyalkoxy, haloalkyl, haloalkoxy or cyano, Y represents hydrogen, halogen, alkyl, alkoxy, cyano, haloalkyl, haloalkoxy, represents in each case optionally substituted phenyl or hetaryl, Z represents hydrogen, halogen, alkyl, haloalkyl, cyano, alkoxy or haloalkoxy, A represents hydrogen, represents in each case optionally halogen-substituted alkyl, alkenyl, alkynyl, alkoxyalkyl, alkylthioalkyl, saturated or unsaturated, optionally substituted cycloalkylalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl, hetaryl or hetarylalkyl, B represents hydrogen, alkyl or alkoxy, D represents NH or oxygen, A and $Q^1$ together with the atoms to which they are attached represent a saturated or unsaturated cycle which contains at least one heteroatom and is unsubstituted or substituted in the A,Q moiety, $Q^1$, $Q^2$, $Q^3$ and $Q^4$ independently of one another represent hydrogen or alkyl, m represents the number 0, 1 or 2, n represents the number 0 or 1, G represents hydrogen (a) or represents one of the groups (b)

(c)

(d)

(e)

(f)

E or (g)

in which

E represents a metal ion or an ammonium ion,

L represents oxygen or sulphur,

M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulphur.

Depending inter alia on the nature of the substituents, the compounds of the formula (I) may be present as optical isomers or isomer mixtures of varying composition which, if appropriate, may be separated in a customary manner. The present invention provides for the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Including D for NH (1) and D for O (2), the following principal structures (I-1) to (I-2) result:

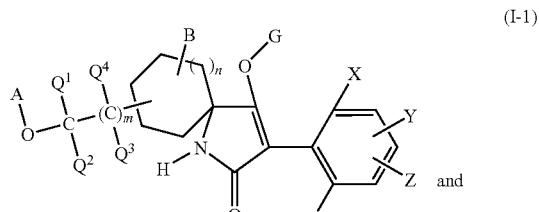
(I-1)

and

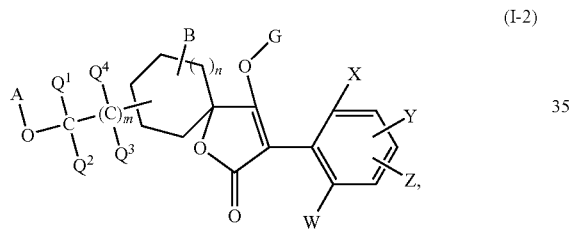
(I-2)

in which
A, B, G, m, n, $Q^1$, $Q^2$, $Q^3$, $Q^4$, W, X, Y and Z are as defined above.

Including the different meanings (a), (b), (c), (d), (e), (f) and (g) of group G, the following principal structures (I-1-a) to (I-1-g) result if D represents NH (1)

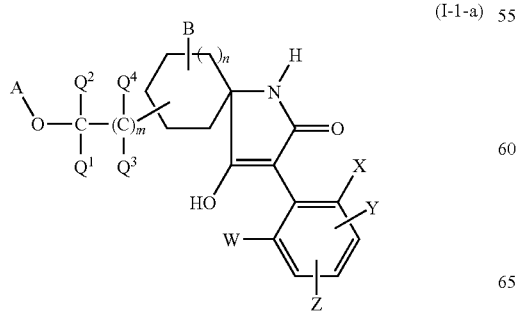
(I-1-a)

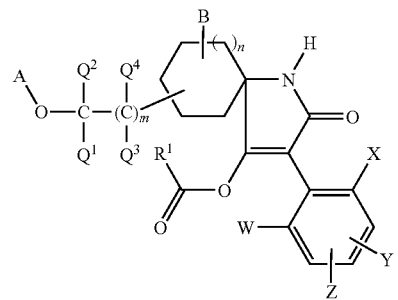
(I-1-b)

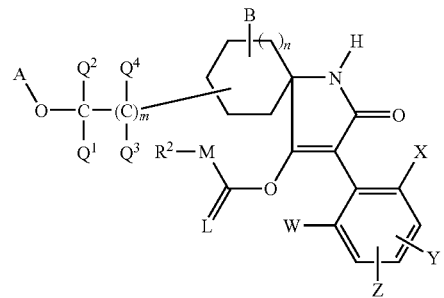
(I-1-c)

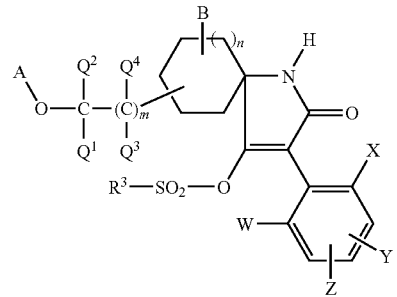
(I-1-d)

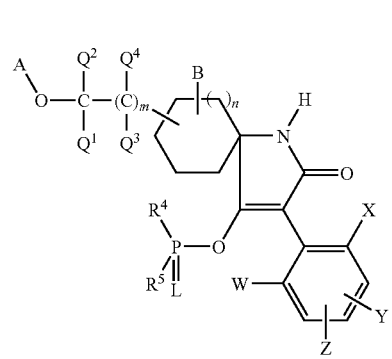
(I-1-e)

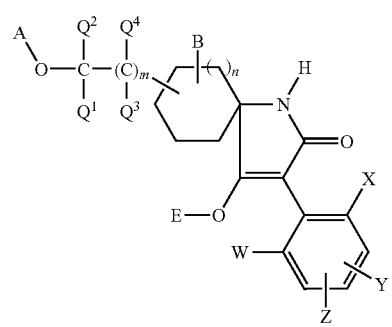
(I-1-f)

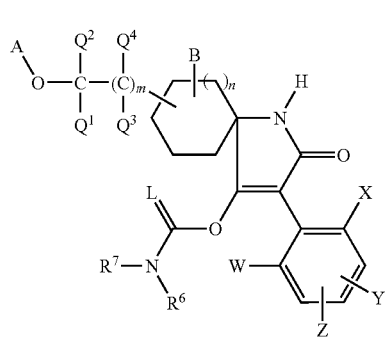
(I-1-g)

in which
A, B, E, L, m, n, M, $Q^1$, $Q^2$, $Q^3$, $Q^4$, W, X, Y, Z, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-2-a) to (I-2-g) result if D represents O (2)

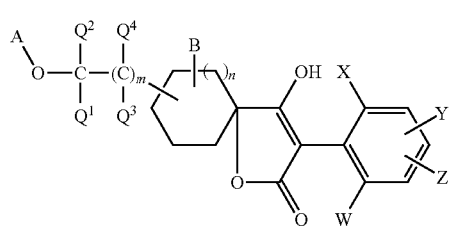
(I-2-a)

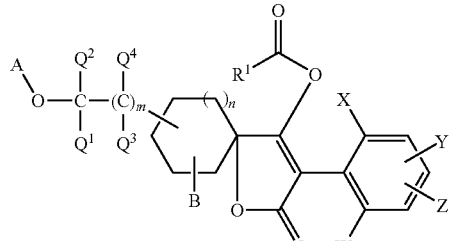
(I-2-b)

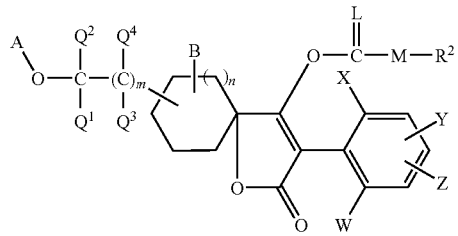
(I-2-c)

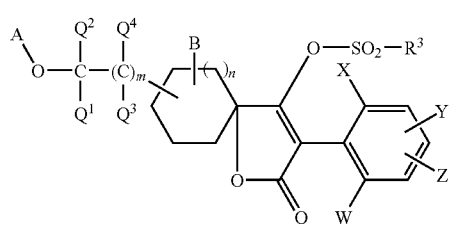
(I-2-d)

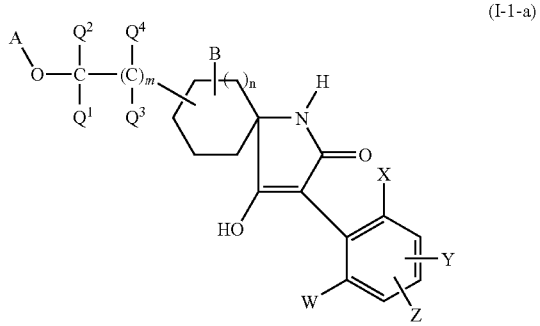
(I-2-e), (I-2-f), (I-2-g)

in which
A, B, E, L, m, n, M, $Q^1$, $Q^2$, $Q^3$, $Q^4$, W, X, Y, Z, $R^1$, $R^2$, $R^3$, $R^4$, $R^5$, $R^6$ and $R^7$ are as defined above.

Furthermore, it has been found that the novel compounds of the formula (I) are obtained by the processes described below:
(A) compounds of the formula (I-1-a)

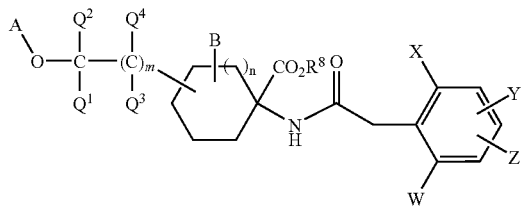
(I-1-a), (II)

in which
A, B, m, n, $Q^1$, $Q^2$, $Q^3$, $Q^4$, W, X, Y and Z are as defined above are obtained,
when
compounds of the formula (II)

in which

A, B, m, n, $Q^1$, $Q^2$, $Q^3$, $Q^4$, W, X, Y and Z are as defined above
and $R^8$ represents alkyl (preferably $C_1$-$C_6$-alkyl)

are condensed intramolecularly in the presence of a diluent and in the presence of a base.

(B) Moreover, it has been found that compounds of the formula (I-2-a)

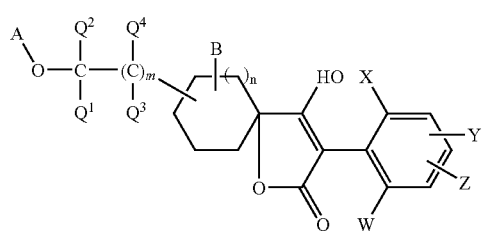

(I-2-a)

in which

A, B, m, n, $Q^1$, $Q^2$, $Q^3$, $Q^4$, W, X, Y and Z are as defined above are obtained when compounds of the formula (III)

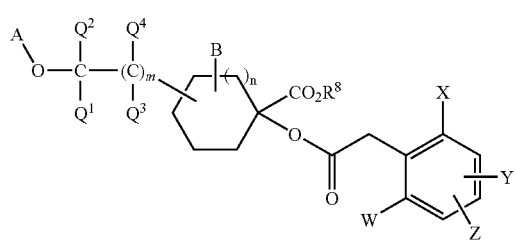

(III)

in which

A, B, m, n, $Q^1$, $Q^2$, $Q^3$, $Q^4$, W, X, Y, Z and $R^8$ are as defined above are condensed intramolecularly in the presence of a diluent and in the presence of a base.

Moreover, it has been found (C) that the compounds of the formulae (I-1-b) to (I-2-b) shown above in which $R^1$, A, B, m, n, $Q^1$, $Q^2$, $Q^3$, $Q^4$, W, X, Y and Z are as defined above are obtained when compounds of the formulae (I-1-a) to (I-2-a) shown above in which A, B, m, n, $Q^1$, $Q^2$, $Q^3$, $Q^4$, W, X, Y and Z are as defined above are in each case α) reacted with compounds of the formula (IV)

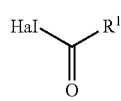

(IV)

in which $R^1$ is as defined above and

Hal represents halogen (in particular chlorine or bromine)

or

β) reacted with carboxylic anhydrides of the formula (V)

$$R^1\text{—CO—O—CO—}R^1 \qquad (V)$$

in which $R^1$ is as defined above, if appropriate in the presence of a diluent and if appropriate in the presence of an acid binder;

(D) that the compounds of the formulae (I-1-c) to (I-2-c) shown above in which $R^2$, A, B, m, n, $Q^1$, $Q^2$, $Q^3$, $Q^4$, M, W, X, Y and Z are as defined above and L represents oxygen are obtained when compounds of the formulae (I-1-a) to (I-2-a) shown above in which A, B, m, n, $Q^1$, $Q^2$, $Q^3$, $Q^4$, W, X, Y and Z are as defined above are in each case reacted with chloroformic esters or chloroformic thioesters of the formula (VI)

$$R^2\text{-M-CO—Cl} \qquad (VI)$$

in which $R^2$ and M are as defined above, if appropriate in the presence of a diluent and if appropriate in the presence of an acid binder;

(E) that compounds of the formulae (I-1-c) to (I-2-c) shown above in which $R^2$, A, B, m, n, $Q^1$, $Q^2$, $Q^3$, $Q^4$, M, W, X, Y and Z are as defined above and L represents sulphur are obtained when compounds of the formulae (I-1-a) to (I-2-a) shown above in which A, B, m, n, $Q^1$, $Q^2$, $Q^3$, $Q^4$, W, X, Y and Z are as defined above are in each case reacted with chloromonothioformic esters or chlorodithioformic esters of the formula (VII)

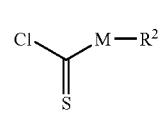

(VII)

in which

M and $R^2$ are as defined above, if appropriate in the presence of a diluent and if appropriate in the presence of an acid binder, (F) that compounds of the formulae (I-1-d) to (I-2-d) shown above in which $R^3$, A, B, m, n, $Q^1$, $Q^2$, $Q^3$, $Q^4$, W, X, Y and Z are as defined above are obtained when compounds of the formulae (I-1-a) to (I-2-a) shown above in which A, B, m, n, $Q^1$, $Q^2$, $Q^3$, $Q^4$, W, X, Y and Z are as defined above are in each case reacted with sulphonyl chlorides of the formula (VIII)

$$R^3\text{—SO}_2\text{—Cl} \qquad (VIII)$$

in which $R^3$ is as defined above, if appropriate in the presence of a diluent and if appropriate in the presence of an acid binder, (G) that compounds of the formulae (I-1-e) to (I-2-e) shown above in which L, $R^4$, $R^5$, A, B, m, n, $Q^1$, $Q^2$, $Q^3$, $Q^4$, W, X, Y and Z are as defined above are obtained when compounds of the formulae (I-1-a) to (I-2-a) shown above in which A, B, m, n, $Q^1$, $Q^2$, $Q^3$, $Q^4$, W, X, Y and Z are as defined above are in each case reacted with phosphorus compounds of the formula (IX)

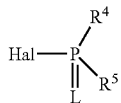
(IX)

in which

L, $R^4$ and $R^5$ are as defined above and

Hal represents halogen (in particular chlorine or bromine), if appropriate in the presence of a diluent and if appropriate in the presence of an acid binder, (H) that compounds of the formulae (I-1-f) to (I-2-f) shown above in which E, A, B, m, n, $Q^1$, $Q^2$, $Q^3$, $Q^4$, W, X, Y and Z are as defined above are obtained when compounds of the formulae (I-1-a) to (I-2-a) shown above in which A, B, m, n, $Q^1$, $Q^2$, $Q^3$, $Q^4$, W, X, Y and Z are as defined above are in each case reacted with metal compounds or amines of the formulae (X) and (XI), respectively Me(OR$^{10}$)$_t$ (X)

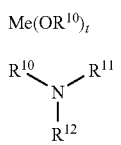
(XI)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (I) that compounds of the formulae (I-1-g) to (I-2-g) shown above in which L, $R^6$, $R^7$, A, B, m, n, $Q^1$, $Q^2$, $Q^3$, $Q^4$, W, X, Y and Z are as defined above are obtained when compounds of the formulae (I-1-a) to (I-2-a) shown above in which A, B, m, n, $Q^1$, $Q^2$, $Q^3$, $Q^4$, W, X, Y and Z are as defined above are in each case α) reacted with isocyanates or isothiocyanates of the formula (XII)

R$^6$—N=C=L (XII)

in which $R^6$ and L are as defined above, if appropriate in the presence of a diluent and if appropriate in the presence of a catalyst, or β) reacted with carbamoyl chlorides or thiocarbamoyl chlorides of the formula (XIII)

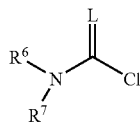
(XIII)

in which

L, $R^6$ and $R^7$ are as defined above, if appropriate in the presence of a diluent and if appropriate in the presence of an acid binder.

Furthermore, it has been found that the novel compounds of the formula (I) are very effective as pesticides, preferably as insecticides, acaricides and/or fungicides and/or herbicides, and additionally frequently tolerated very well by plants, in particular by crop plants.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, (a') at least one substituted, cyclic ketoenol of the formula (I) in which A, B, D, G, m, n, $Q^1$, $Q^2$, $Q^3$, $Q^4$, W, X, Y and Z are as defined above and (b') at least one crop plant compatibility-improving compound from the following group of compounds:

4-dichloroacetyl-1-oxa-4-azaspiro[4.5]decane (AD-67, MON4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, and/or one of the following compounds, defined by general formulae of the general formula (IIa)

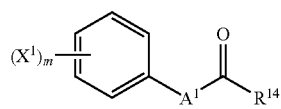

or of the general formula (IIb)

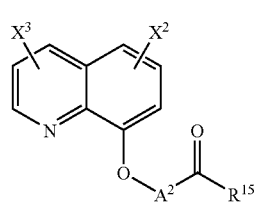

or of the formula (IIc)

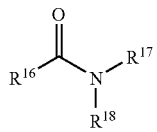

where
m represents a number 0, 1, 2, 3, 4 or 5,
$A^1$ represents one of the divalent heterocyclic groupings shown below,

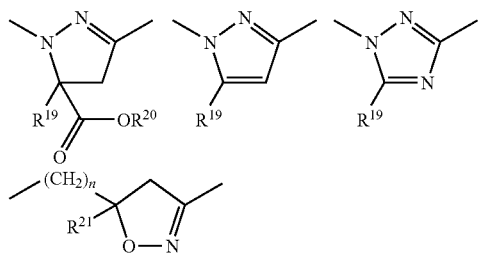

n represents a number 0, 1, 2, 3, 4 or 5,
$A^2$ represents optionally $C_1$-$C_4$-alkyl- and/or $C_1$-$C_4$-alkoxycarbonyl- and/or $C_1$-$C_4$-alkenyloxy-carbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$R^{20}$ represents hydrogen, in each case optionally hydroxyl, cyano, halogen- or $C_1$-$C_4$-alkoxy-substituted $C_1$-$C_6$-alkyl, $C_3$-$C_6$-cycloalkyl or tri-($C_1$-$C_4$-alkyl)-silyl,
$R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

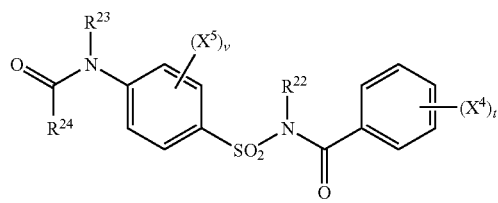

or of the general formula (IIe)

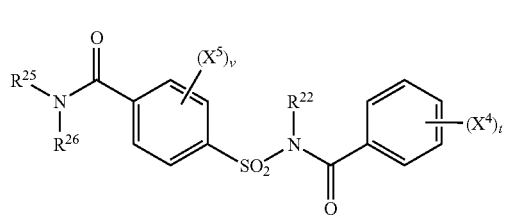

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano, halogen- or $C_1$-$C_4$-alkyl-substituted $C_3$-$C_6$-Cycloalkyl, $C_3$-$C_6$-cycloalkyloxy, $C_3$-$C_6$-Cycloalkylthio or $C_3$-$C_6$-cycloalkylamino, $R^{25}$ represents hydrogen, optionally cyano, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano, halogen- or $C_1$-$C_4$-alkyl-substituted $C_3$-$C_6$-cycloalkyl, $R^{26}$ represents hydrogen, optionally cyano, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro, cyano-, halogen, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

W preferably represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X preferably represents hydrogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y preferably represents hydrogen, halogen, $C_1$-$C_6$-alkyl, $C_1$-$C_6$-alkoxy, cyano, $C_1$-$C_4$-haloalkyl, haloalkoxy, represents $V^1$- and $V^2$-substituted phenyl or pyridyl, $V^1$ preferably represents halogen, $C_1$-$C_{12}$-alkyl, $C_1$-$C_6$-alkoxy, $C_1$-$C_4$-haloalkyl, $C_1$-$C_4$-haloalkoxy, cyano or nitro, $V^2$ preferably represents hydrogen, halogen, $C_1$-$C_6$-alkyl, $C_1$-$C_6$-alkoxy or $C_1$-$C_4$-haloalkyl, $V^1$ and $V^2$ together preferably represent $C_3$-$C_4$-alkanediyl which may optionally be substituted by halogen and/or $C_1$-$C_2$-alkyl and which may optionally be interrupted by one or two oxygen atoms, Z preferably represents hydrogen, halogen, $C_1$-$C_6$-alkyl, $C_1$-$C_4$-haloalkyl, cyano, $C_1$-$C_6$-alkoxy or $C_1$-$C_4$-haloalkoxy, A preferably represents hydrogen or in each case optionally halogen-substituted $C_1$-$C_8$-alkyl, $C_3$-$C_8$-alkenyl, $C_3$-$C_8$-alkynyl, $C_1$-$C_6$-alkoxy-$C_1$-$C_6$-alkyl, $C_1$-$C_6$-alkylthio-$C_1$-$C_6$-alkyl, optionally halogen, $C_1$-$C_6$-alkyl- or $C_1$-$C_6$-alkoxy-substituted $C_3$-$C_8$-cycloalkyl-$C_1$-$C_4$-alkyl in which optionally one or two not directly adjacent ring members are replaced by oxygen and/or sulphur or represents in each case optionally halogen, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 to 6 ring atoms (for example pyridyl, pyrimidyl or thiazolyl), phenyl-$C_1$-$C_4$-alkyl or hetaryl-$C_1$-$C_4$-alkyl having 5 to 6 ring atoms (for example furanyl, pyridyl, pyrazolyl, pyrimidyl, thiazolyl, thienyl), B preferably represents hydrogen, $C_1$-$C_4$-alkyl or $C_1$-$C_4$-alkoxy, D preferably represents NH or oxygen, $Q^1$, $Q^2$, $Q^3$ and $Q^4$ independently of one another preferably represent hydrogen or $C_1$-$C_2$-alkyl, or A and $Q^1$ together with the atoms to which they are attached preferably represent a saturated 5- to 6-membered ring which is interrupted by at least one heteroatom and may optionally be substituted by $C_1$-$C_4$-alkyl, $C_1$-$C_4$-alkoxy, $C_1$-$C_4$-alkoxy-$C_1$-$C_2$-alkyl or $C_1$-$C_4$-haloalkyl, m preferably represents the number 0, 1 or 2, n preferably represents the number 0 or 1, G preferably represents hydrogen (a) or represents one of the groups

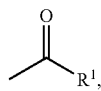

(b)

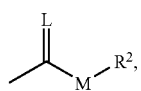

(c)

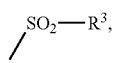

(d)

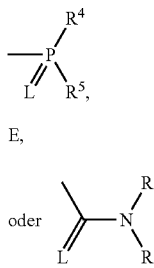
(e)

E, (f)

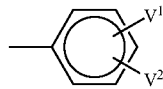 oder (g)

in which
E represents a metal ion or an ammonium ion,
L represents oxygen or sulphur and
M represents oxygen or sulphur,
$R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur,
preferably represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl,
preferably represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
preferably represents optionally halogen- or $C_1$-$C_6$-alkyl-substituted 5- or 6-membered hetaryl having one or two heteroatoms from the group consisting of oxygen, sulphur and nitrogen,
preferably represents optionally halogen- or $C_1$-$C_6$-alkyl-substituted phenoxy-$C_1$-$C_6$-alkyl or
preferably represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen,
$R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
preferably represents optionally halogen-, $C_1$-$C_6$-alkyl- or $C_1$-$C_6$-alkoxy-substituted $C_3$-$C_8$-cycloalkyl or
preferably represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl,
$R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl,
$R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio, $C_1$-$C_4$-haloalkylthio, $C_1$-$C_4$-alkyl- or $C_1$-$C_4$-haloalkyl-substituted phenyl, phenoxy or phenylthio,
$R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, fluorine, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position particularly preferably represents hydrogen, fluorine, chlorine, bromine, iodine, methoxy, ethoxy, cyano, trifluoromethyl, difluoromethoxy or trifluoromethoxy, Z particularly preferably represents hydrogen.

W also particularly preferably represents hydrogen, fluorine, chlorine, bromine or $C_1$-$C_4$-alkyl, X also particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y also in the 4-position particularly preferably represents the radical

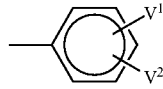

Z also particularly preferably represents hydrogen, $V^1$ also particularly preferably represents fluorine, chlorine, $C_1$-$C_4$-alkyl, $C_1$-$C_4$-alkoxy, $C_1$-$C_2$-haloalkyl, $C_1$-$C_2$-haloalkoxy, cyano or nitro, $V^2$ also particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together also particularly preferably represent —O—$CH_2$—O— or —O—$CF_2$—O—.

W likewise particularly preferably represents hydrogen, fluorine, chlorine, bromine or $C_1$-$C_4$-alkyl, X likewise particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y likewise in the 5-position particularly preferably represents the radical Z likewise in the 4-position particularly preferably represents hydrogen, $V^1$ likewise particularly preferably represents fluorine, chlorine, $C_1$-$C_4$-alkyl, $C_1$-$C_4$-alkoxy, $C_1$-$C_2$-haloalkyl, $C_1$-$C_2$-haloalkoxy, cyano or nitro, $V^2$ likewise particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together likewise particularly preferably represent —O—CH$_2$—O— or —O—CF$_2$—O—.

W moreover particularly preferably represents hydrogen, $C_1$-$C_4$-alkyl, $C_2$-$C_4$-alkenyl, $C_2$-$C_4$-alkynyl, $C_1$-$C_4$-alkoxy, fluorine, chlorine, bromine or trifluoromethyl, X moreover particularly preferably represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y moreover in the 4-position particularly preferably represents $C_1$-$C_4$-alkyl, Z moreover particularly preferably represents hydrogen.

W furthermore particularly preferably represents hydrogen, fluorine, chlorine, bromine, $C_1$-$C_4$-alkyl or $C_1$-$C_4$-alkoxy, X furthermore particularly preferably represents chlorine, bromine, iodine, $C_1$-$C_4$-alkyl, $C_1$-$C_4$-alkoxy, $C_1$-$C_2$-haloalkyl, $C_1$-$C_2$-haloalkoxy or cyano, Y moreover in the 4-position particularly preferably represents hydrogen,

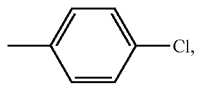

chlorine, bromine, iodine, $C_1$-$C_4$-alkyl, $C_1$-$C_2$-haloalkyl or $C_1$-$C_2$-haloalkoxy, Z furthermore in the 3- or 5-position particularly preferably represents fluorine, chlorine, bromine, iodine, $C_1$-$C_4$-alkyl, $C_1$-$C_2$-haloalkyl, $C_1$-$C_4$-alkoxy or $C_1$-$C_2$-haloalkoxy, A particularly preferably represents hydrogen, represents $C_1$-$C_6$-alkyl, $C_3$-$C_6$-alkenyl, $C_3$-$C_6$-alkynyl, $C_1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$-alkoxy, B particularly preferably represents hydrogen, $C_1$-$C_2$-alkyl or $C_1$-$C_2$-alkoxy, D particularly preferably represents NH or oxygen, $Q^1$, $Q^2$, $Q^3$ and $Q^4$ independently of one another particularly preferably represent hydrogen or methyl, or A and $Q^1$ together with the atoms to which they are attached particularly preferably represent a saturated 5- to 6-membered ring which is interrupted by at least one oxygen atom and which may optionally be substituted by methyl, ethyl, methoxy, ethoxy, methoxymethyl, ethoxymethyl or trifluoromethyl, m particularly preferably represents the number 0 or 1, n particularly preferably represents the number 1, G particularly preferably represents hydrogen (a) or represents one of the groups (b)

(c)

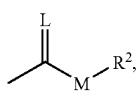

-continued (d)

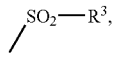

(e)

(f)

E, (g)

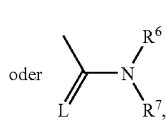

in which

E represents a metal ion or an ammonium ion,

L represents oxygen or sulphur and

M represents oxygen or sulphur.

$R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur, particularly preferably represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, particularly preferably represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, particularly preferably represents pyrazolyl, thiazolyl, pyridyl, pyrimidyl, furanyl or thienyl, each of which is optionally mono- to disubstituted by fluorine, chlorine, bromine or $C_1$-$C_4$-alkyl, particularly preferably represents phenoxy-$C_1$-$C_5$-alkyl which is optionally mono- to disubstituted by fluorine, chlorine, bromine or $C_1$-$C_4$-alkyl or particularly preferably represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, particularly preferably represents $C_3$-$C_7$-cycloalkyl which is optionally mono- to disubstituted by fluorine, chlorine, $C_1$-$C_4$-alkyl or $C_1$-$C_4$-alkoxy or particularly preferably represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, methoxy, ethoxy or trifluoromethyl, X very particularly preferably represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position very particularly preferably represents hydrogen, chlorine, bromine, iodine, methoxy, trifluoromethyl or trifluoromethoxy, Z very particularly preferably represents hydrogen.

W also very particularly preferably represents hydrogen, chlorine, bromine, methyl or ethyl, X also very particularly preferably represents chlorine, bromine, methyl, ethyl, propyl, methoxy, trifluoromethyl, difluoromethoxy, trifluoromethoxy or cyano, Y also in the 4-position very particularly preferably represents the radical

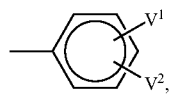

Z also very particularly preferably represents hydrogen, $V^1$ also very particularly preferably represents fluorine, chlorine, methyl, methoxy, trifluoromethyl, trifluoromethoxy or cyano, $V^2$ also very particularly preferably represents hydrogen, fluorine, chlorine, methyl, methoxy or trifluoromethyl.

W likewise very particularly preferably represents hydrogen, chlorine or methyl, X likewise very particularly preferably represents chlorine, methyl, trifluoromethyl, methoxy, difluoromethoxy, trifluoromethoxy or cyano, Y likewise in the 5-position very particularly preferably represents the radical

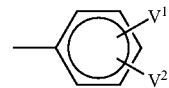

Z likewise in the 4-position very particularly preferably represents hydrogen, $V^1$ likewise very particularly preferably represents fluorine, chlorine, methyl, methoxy, trifluoromethyl, trifluoromethoxy or cyano, $V^2$ likewise very particularly preferably represents hydrogen, fluorine, chlorine, methyl, methoxy or trifluoromethyl.

W moreover very particularly preferably represents hydrogen, methyl, ethyl, methoxy, ethoxy, chlorine or bromine, X moreover very particularly preferably represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y moreover in the 4-position very particularly preferably represents methyl or ethyl, Z moreover very particularly preferably represents hydrogen.

W furthermore very particularly preferably represents hydrogen, chlorine, bromine, methyl or ethyl, X furthermore very particularly preferably represents chlorine, bromine, iodine, methyl, ethyl, methoxy, trifluoromethyl, difluoromethoxy or trifluoromethoxy, Y furthermore in the 4-position very particularly preferably represents hydrogen,

chlorine, bromine, methyl or ethyl,

Z furthermore in the 3- or 5-position very particularly preferably represents fluorine, chlorine, bromine, iodine, methyl, ethyl, trifluoromethyl or trifluoromethoxy, A very particularly preferably represents hydrogen, very particularly preferably represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine, represents cyclopropylmethyl, cyclopentylmethyl or cyclohexylmethyl, B very particularly preferably represents hydrogen, D very particularly preferably represents NH or oxygen, $Q^1$, $Q^2$, $Q^3$ and $Q^4$ very particularly preferably represent hydrogen, or A and $Q^1$ together with the atoms to which they are attached very particularly preferably represent a saturated 5- to 6-membered ring which is interrupted by at least one oxygen atom and may optionally be substituted by methyl or ethyl, m very particularly preferably represents the number 0 or 1, n very particularly preferably represents the number 1, G very particularly preferably represents hydrogen (a) or represents one of the groups

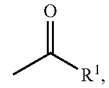

(b)

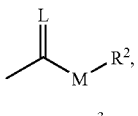
(c)

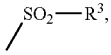
(d)

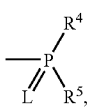
(e)

E or (f)

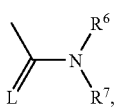
(g)

in which
E represents a metal ion or an ammonium ion,
L represents oxygen or sulphur and
M represents oxygen or sulphur.
$R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
very particularly preferably represents phenyl which is optionally mono- to disubstituted by fluorine, chlorine, bromine, cyano, nitro, methyl, ethyl, n-propyl, isopropyl, methoxy, ethoxy, trifluoromethyl or trifluoromethoxy,
very particularly preferably represents furanyl, thienyl or pyridyl, each of which is optionally monosubstituted by chlorine, bromine or methyl,
$R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
very particularly preferably represents cyclopentyl or cyclohexyl
or very particularly preferably represents phenyl or benzyl, each of which is optionally mono- to disubstituted by fluorine, chlorine, cyano, nitro, methyl, ethyl, methoxy, trifluoromethyl or trifluoromethoxy,
$R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro,
$R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy,
$R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- to disubstituted by fluorine, chlorine, bromine, methyl, methoxy or trifluoromethyl, or together represent a $C_5$-$C_6$-alkylene radical in which optionally one methylene group is replaced by oxygen or sulphur.
W especially preferably represents chlorine, methyl or ethyl,
X especially preferably represents chlorine, methyl, ethyl, methoxy or ethoxy,
Y in the 4-position especially preferably represents chlorine, bromine, iodine or methoxy,
Z especially preferably represents hydrogen.
W likewise especially preferably represents hydrogen or methyl,
X likewise especially preferably represents chlorine or methyl,
Y likewise in the 5-position especially preferably represents

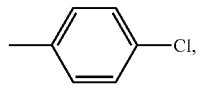

Z likewise in the 4-position especially preferably represents hydrogen.
W moreover especially preferably represents methyl, ethyl or methoxy,
X moreover especially preferably represents chlorine, bromine, methyl, ethyl or methoxy,
Y moreover in the 4-position especially preferably represents methyl,
Z moreover especially preferably represents hydrogen.
W furthermore especially preferably represents hydrogen or methyl,
X furthermore especially preferably represents bromine, methyl or methoxy,
Y furthermore in the 4-position especially preferably represents

hydrogen, chlorine or methyl,
Z furthermore in the 3- or 5-position especially preferably represents methyl,
A especially preferably represents $C_1$-$C_4$-alkyl,
B especially preferably represents hydrogen,
D especially preferably represents NH or oxygen,
$Q^1$, $Q^2$, $Q^3$ and $Q^4$ especially preferably represent hydrogen,
m especially preferably represents the number 0 or 1,
n especially preferably represents the number 1,
G especially preferably represents hydrogen (a) or represents one of the groups

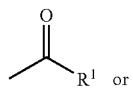
(b)

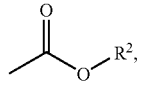
(c)

in which
$R^1$ especially preferably represents $C_1$-$C_{10}$-alkyl, $C_1$-$C_4$-alkoxy-$C_1$-$C_2$-alkyl or cyclopropyl, $R^2$ especially preferably represents $C_1$-$C_{10}$-alkyl or benzyl.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

With emphasis,

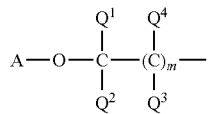

is located in the 4' position.

Likewise with emphasis,

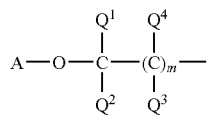

is located in the 3' position.

In addition to the compounds mentioned in the Preparation Examples, the following compounds of the formula (I-1-a) may be specifically mentioned:

TABLE 1

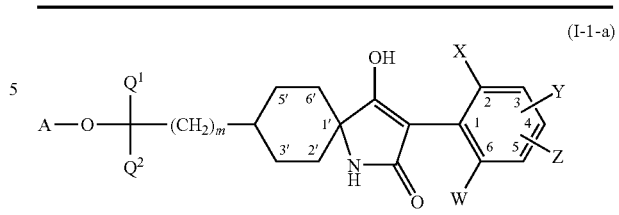

(I-1-a)

| A | $Q^1$ | $Q^2$ | m | X | W | Y | Z |
|---|---|---|---|---|---|---|---|
| $CH_3$ | H | H | 0 | $CH_3$ | H | H | H |
| $CH_3$ | H | H | 0 | Br | H | H | H |

TABLE 1-continued

| A | $Q^1$ | $Q^2$ | m | X | W | Y | Z |
|---|---|---|---|---|---|---|---|
| $CH_3$ | H | H | 0 | Cl | H | H | H |
| $CH_3$ | H | H | 0 | $CF_3$ | H | H | H |
| $CH_3$ | H | H | 0 | $OCH_3$ | H | H | H |
| $CH_3$ | H | H | 0 | Br | H | 4-Cl | H |
| $CH_3$ | H | H | 0 | Cl | H | 4-Br | H |
| $CH_3$ | H | H | 0 | Cl | H | 4-Cl | H |
| $CH_3$ | H | H | 0 | Cl | H | 4-$CH_3$ | H |
| $CH_3$ | H | H | 0 | $CH_3$ | H | 4-Cl | H |
| $CH_3$ | H | H | 0 | $CH_3$ | H | 4-$CH_3$ | H |
| $CH_3$ | H | H | 0 | Cl | Cl | H | H |
| $CH_3$ | H | H | 0 | Cl | $OCH_3$ | H | H |
| $CH_3$ | H | H | 0 | Cl | $CH_3$ | H | H |
| $CH_3$ | H | H | 0 | Cl | $OC_2H_5$ | H | H |
| $CH_3$ | H | H | 0 | $OCH_3$ | $OCH_3$ | H | H |
| $CH_3$ | H | H | 0 | $CH_3$ | $CH_3$ | H | H |
| $CH_3$ | H | H | 0 | Br | $CH_3$ | 4-Br | H |
| $CH_3$ | H | H | 0 | Cl | Cl | 4-$CH_3$ | H |
| $CH_3$ | H | H | 0 | $CH_3$ | Br | 4-$CH_3$ | H |
| $CH_3$ | H | H | 0 | $CH_3$ | Cl | 4-$CH_3$ | H |
| $CH_3$ | H | H | 0 | $OCH_3$ | $CH3$ | 4-$CH_3$ | H |
| $CH_3$ | H | H | 0 | $OC_2H_5$ | $CH_3$ | 4-$CH_3$ | H |
| $CH_3$ | H | H | 0 | $OC_3H_7$ | $CH_3$ | 4-$CH_3$ | H |
| $CH_3$ | H | H | 0 | $CH_3$ | $CH_3$ | 4-$CH_3$ | H |
| $CH_3$ | H | H | 0 | Br | Br | 4-$CH_3$ | H |
| $CH_3$ | H | H | 0 | $CH_3$ | $CH_3$ | 4-Br | H |
| $CH_3$ | H | H | 0 | $C_2H_5$ | $CH_3$ | H | H |
| $CH_3$ | H | H | 0 | $C_2H_5$ | $C_2H_5$ | H | H |
| $CH_3$ | H | H | 0 | $OCH_3$ | $C_2H_5$ | 4-$CH_3$ | H |
| $CH_3$ | H | H | 0 | $CH_3$ | $CH_3$ | 4-$OCH_3$ | H |
| $CH_3$ | H | H | 0 | Br | Cl | 4-$CH_3$ | H |
| $CH_3$ | H | H | 0 | Br | $CH_3$ | 4-Cl | H |
| $CH_3$ | H | H | 0 | Cl | $CH_3$ | 4-Br | H |
| $CH_3$ | H | H | 0 | $CH_3$ | $CH_3$ | 4-Cl | H |
| $CH_3$ | H | H | 0 | $C_2H_5$ | $CH_3$ | 4-$CH_3$ | H |
| $CH_3$ | H | H | 0 | $C_2H_5$ | $CH_3$ | 4-$C_2H_5$ | H |
| $CH_3$ | H | H | 0 | $C_2H_5$ | $C_2H_5$ | 4-$CH_3$ | H |
| $CH_3$ | H | H | 0 | $C_2H_5$ | $C_2H_5$ | 4-$C_2H_5$ | H |
| $CH_3$ | H | H | 0 | $C_2H_5$ | $CH_3$ | 4-Cl | H |
| $CH_3$ | H | H | 0 | $C_2H_5$ | $C_2H_5$ | 4-Cl | H |
| $CH_3$ | H | H | 0 | $C_2H_5$ | $CH_3$ | 4-Br | H |
| $CH_3$ | H | H | 0 | $C_2H_5$ | $C_2H_5$ | 4-Br | H |
| $CH_3$ | H | H | 0 | $C_2H_5$ | Cl | 4-$CH_3$ | H |
| $CH_3$ | H | H | 0 | $C_2H_5$ | Br | 4-$CH_3$ | H |
| $CH_3$ | H | H | 0 | $C_2H_5$ | Cl | 4-Cl | H |
| $CH_3$ | H | H | 0 | $C_2H_5$ | Br | 4-Br | H |
| $CH_3$ | H | H | 0 | $C_2H_5$ | Cl | 4-Br | H |
| $CH_3$ | H | H | 0 | $C_2H_5$ | Br | 4-Cl | H |
| $CH_3$ | H | H | 0 | $OCH_3$ | $CH_3$ | 4-Cl | H |
| $CH_3$ | H | H | 0 | $OCH_3$ | $C_2H_5$ | 4-Cl | H |
| $CH_3$ | H | H | 0 | $OC_2H_5$ | $CH_3$ | 4-Cl | H |
| $CH_3$ | H | H | 0 | $OC_2H_5$ | $C_2H_5$ | 4-Cl | H |
| $CH_3$ | H | H | 0 | Cl | $OCH_3$ | 4-$CH_3$ | H |
| $CH_3$ | H | H | 0 | Cl | $OC_2H_5$ | 4-$CH_3$ | H |
| $CH_3$ | H | H | 0 | Cl | Cl | 4-Cl | H |
| $CH_3$ | H | H | 0 | Cl | H | 4-Cl | 5-Cl |
| $CH_3$ | H | H | 0 | $CH_3$ | H | 4-$CH_3$ | 5-$CH_3$ |
| $CH_3$ | H | H | 0 | $CH_3$ | H | 4-Cl | 5-$CH_3$ |
| $CH_3$ | H | H | 0 | Br | H | 4-Cl | 5-$CH_3$ |
| $CH_3$ | H | H | 0 | Br | H | 4-$CH_3$ | 5-$CH_3$ |
| $CH_3$ | H | H | 0 | Cl | H | 4-Br | 5-$CH_3$ |
| $CH_3$ | H | H | 0 | Cl | H | 4-Cl | 5-$CH_3$ |
| $CH_3$ | H | H | 0 | $CH_3$ | H | 4-Br | 5-$CH_3$ |
| $CH_3$ | H | H | 0 | Cl | H | 4-$CH_3$ | 5-Cl |
| $CH_3$ | H | H | 0 | $CH_3$ | H | H | 5-$CH_3$ |
| $CH_3$ | H | H | 0 | Cl | H | H | 5-$CH_3$ |
| $CH_3$ | H | H | 0 | Br | H | H | 5-$CH_3$ |
| $CH_3$ | H | H | 0 | $CH_3$ | H | H | 5-Cl |
| $CH_3$ | H | H | 0 | $CH_3$ | H | H | 5-Br |

TABLE 1-continued

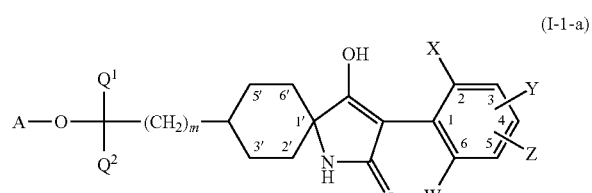

(I-1-a)

| A | Q¹ | Q² | m | X | W | Y | Z |
|---|----|----|---|---|---|---|---|
| CH$_3$ | H | H | 0 | CH$_3$ | CH$_3$ | 4-CH$_3$ | 5-CH$_3$ |
| CH$_3$ | H | H | 0 | CH$_3$ | CH$_3$ | 4-CH$_3$ | 5-Cl |
| CH$_3$ | H | H | 0 | CH$_3$ | CH$_3$ | 4-CH$_3$ | 5-Br |
| CH$_3$ | H | H | 0 | CH$_3$ | CH$_3$ | H | 3-Cl |
| CH$_3$ | H | H | 0 | CH$_3$ | CH$_3$ | H | 3-Br |
| CH$_3$ | H | H | 0 | Cl | Cl | H | 3-Br |
| CH$_3$ | H | H | 0 | CH$_3$ | CH$_3$ | 4-(4-Cl—C$_6$H$_4$) | H |
| CH$_3$ | H | H | 0 | C$_2$H$_5$ | CH$_3$ | 4-(4-Cl—C$_6$H$_4$) | H |
| CH$_3$ | H | H | 0 | C$_2$H$_5$ | C$_2$H$_5$ | 4-(4-Cl—C$_6$H$_4$) | H |
| CH$_3$ | H | H | 0 | Cl | CH$_3$ | 4-(4-Cl—C$_6$H$_4$) | H |
| CH$_3$ | H | H | 0 | Cl | C$_2$H$_5$ | 4-(4-Cl—C$_6$H$_4$) | H |
| CH$_3$ | H | H | 0 | CH$_3$ | H | 5-(4-Cl—C$_6$H$_4$) | H |
| CH$_3$ | H | H | 0 | CH$_3$ | CH$_3$ | 5-(4-Cl—C$_6$H$_4$) | H |
| CH$_3$ | H | H | 0 | CH$_3$ | H | 5-(4-Cl—C$_6$H$_4$) | 4-CH$_3$ |
| CH$_3$ | H | H | 0 | CH$_3$ | CH$_3$ | 5-(4-Cl—C$_6$H$_4$) | 4-CH$_3$ |
| CH$_3$ | H | H | 0 | Cl | H | 5-(4-Cl—C$_6$H$_4$) | H |
| CH$_3$ | H | H | 0 | I | H | H | H |
| CH$_3$ | H | H | 0 | I | H | 4-CH$_3$ | H |
| CH$_3$ | H | H | 0 | I | CH$_3$ | H | H |
| CH$_3$ | H | H | 0 | I | C$_2$H$_5$ | H | H |
| CH$_3$ | H | H | 0 | CH$_3$ | H | H | 5-I |
| CH$_3$ | H | H | 0 | CH$_3$ | H | 4-CH$_3$ | 5-I |
| CH$_3$ | H | H | 0 | I | CH$_3$ | 4-CH$_3$ | H |
| CH$_3$ | H | H | 0 | I | C$_2$H$_5$ | 4-CH$_3$ | H |
| CH$_3$ | H | H | 0 | I | CH$_3$ | 4-Cl | H |
| CH$_3$ | H | H | 0 | I | C$_2$H$_5$ | 4-Cl | H |
| CH$_3$ | H | H | 0 | I | Cl | 4-CH$_3$ | H |
| CH$_3$ | H | H | 0 | I | H | 4-CH$_3$ | 5-CH$_3$ |
| CH$_3$ | H | H | 0 | CH$_3$ | H | 4-I | H |
| CH$_3$ | H | H | 0 | C$_2$H$_5$ | H | 4-I | H |
| CH$_3$ | H | H | 0 | CH$_3$ | CH$_3$ | 4-I | H |
| CH$_3$ | H | H | 0 | C$_2$H$_5$ | CH$_3$ | 4-I | H |
| CH$_3$ | H | H | 0 | C$_2$H$_5$ | C$_2$H$_5$ | 4-I | H |
| CH$_3$ | H | H | 0 | Cl | CH$_3$ | 4-I | H |
| CH$_3$ | H | H | 0 | Cl | C$_2$H$_5$ | 4-I | H |
| CH$_3$ | H | H | 0 | CH$_3$ | H | 4-I | 5-CH$_3$ |
| CH$_3$ | H | H | 0 | CH$_3$ | CH$_3$ | H | 3-I |
| CH$_3$ | H | H | 0 | I | H | H | 5-CH$_3$ |
| CH$_3$ | H | H | 0 | C$_2$H$_5$ | H | H | H |
| CH$_3$ | H | H | 0 | C$_2$H$_5$ | H | 4-Cl | H |
| CH$_3$ | H | H | 0 | C$_2$H$_5$ | H | 4-Br | H |
| CH$_3$ | H | H | 0 | C$_2$H$_5$ | H | 4-CH$_3$ | H |

TABLE 2

A, m, Q¹, Q², W, X, Y and Z as stated in Table 1 where

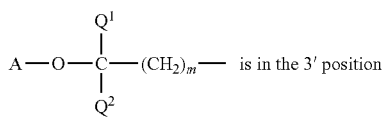

is in the 3′ position

Table 3: m, Q¹, Q², W, X, Y and Z as stated in Table 1
A=C$_2$H$_5$

TABLE 4

A, m, Q¹, Q², W, X, Y and Z as stated in Table 3

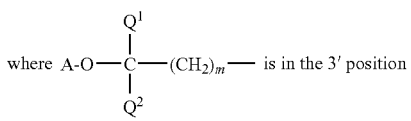

is in the 3′ position

Table 5: m, Q¹, Q², W, X, Y and Z as stated in Table 1
A=n-C$_3$H$_7$

TABLE 6

A, m, Q¹, Q², W, X, Y and Z as stated in Table 5

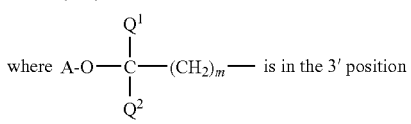

is in the 3′ position

Table 7: A, Q¹, Q², W, X, Y and Z as stated in Table 1
where m=1

TABLE 8

A, Q¹, Q², W, X, Y and Z as stated in Table 1

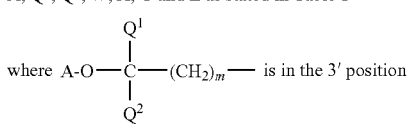

is in the 3′ position and m=1
Table 9: Q¹, Q², W, X, Y and Z as stated in Table 1
where m=1 and A=C$_2$H$_5$

TABLE 10

Q¹, Q², W, X, Y and Z as stated in Table 1 where

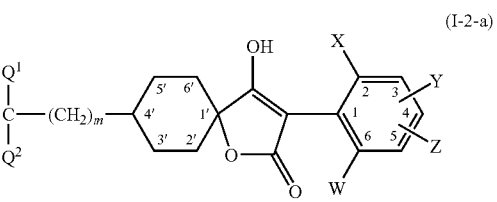

is in the 3′ position where m = 1 and A = C$_2$H$_5$

In addition to the compounds mentioned in the Preparation Examples, the following compounds of the formula (I-2-a) may be specifically mentioned:

TABLE 11

(I-2-a)

| A | Q¹ | Q² | m | X | W | Y | Z |
|---|----|----|---|---|---|---|---|
| CH$_3$ | H | H | 0 | CH$_3$ | H | H | H |
| CH$_3$ | H | H | 0 | C$_2$H$_5$ | H | H | H |
| CH$_3$ | H | H | 0 | Br | H | H | H |

TABLE 11-continued (I-2-a)

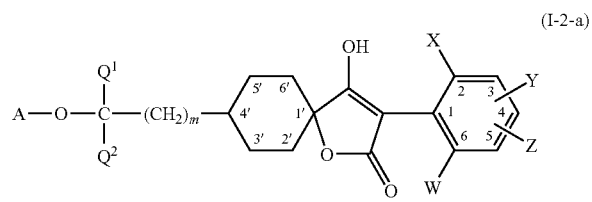

| A | Q¹ | Q² | m | X | W | Y | Z |
|---|---|---|---|---|---|---|---|
| CH₃ | H | H | 0 | Cl | H | H | H |
| CH₃ | H | H | 0 | CF₃ | H | H | H |
| CH₃ | H | H | 0 | OCH₃ | H | H | H |
| CH₃ | H | H | 0 | Br | H | 4-Cl | H |
| CH₃ | H | H | 0 | Cl | H | 4-Br | H |
| CH₃ | H | H | 0 | Cl | H | 4-Cl | H |
| CH₃ | H | H | 0 | Cl | H | 4-CH₃ | H |
| CH₃ | H | H | 0 | CH₃ | H | 4-Cl | H |
| CH₃ | H | H | 0 | CH₃ | H | 4-Br | H |
| CH₃ | H | H | 0 | C₂H₅ | H | 4-CH₃ | H |
| CH₃ | H | H | 0 | C₂H₅ | H | Cl | H |
| CH₃ | H | H | 0 | C₂H₅ | H | Br | H |
| CH₃ | H | H | 0 | Cl | Cl | H | H |
| CH₃ | H | H | 0 | Cl | OCH₃ | H | H |
| CH₃ | H | H | 0 | Cl | CH₃ | H | H |
| CH₃ | H | H | 0 | Cl | OC₂H₅ | H | H |
| CH₃ | H | H | 0 | OCH₃ | OCH₃ | H | H |
| CH₃ | H | H | 0 | CH₃ | CH₃ | H | H |
| CH₃ | H | H | 0 | C₂H₅ | CH₃ | H | H |
| CH₃ | H | H | 0 | C₂H₅ | C₂H₅ | H | H |
| CH₃ | H | H | 0 | Br | CH₃ | 4-Br | H |
| CH₃ | H | H | 0 | Cl | Cl | 4-CH₃ | H |
| CH₃ | H | H | 0 | Cl | Br | 4-CH₃ | H |
| CH₃ | H | H | 0 | CH₃ | Cl | 4-CH₃ | H |
| CH₃ | H | H | 0 | OCH₃ | CH₃ | 4-CH₃ | H |
| CH₃ | H | H | 0 | OCH₃ | C₂H₅ | 4-CH₃ | H |
| CH₃ | H | H | 0 | OC₂H₅ | CH₃ | 4-CH₃ | H |
| CH₃ | H | H | 0 | OC₃H₇ | CH₃ | 4-CH₃ | H |
| CH₃ | H | H | 0 | CH₃ | CH₃ | 4-CH₃ | H |
| CH₃ | H | H | 0 | Br | Br | 4-CH₃ | H |
| CH₃ | H | H | 0 | Cl | Cl | 4-CH₃ | H |
| CH₃ | H | H | 0 | CH₃ | CH₃ | 4-Br | H |
| CH₃ | H | H | 0 | CH₃ | CH₃ | 4-OCH₃ | H |
| CH₃ | H | H | 0 | Br | Cl | 4-CH₃ | H |
| CH₃ | H | H | 0 | Br | CH₃ | 4-Cl | H |
| CH₃ | H | H | 0 | Cl | CH₃ | 4-Br | H |
| CH₃ | H | H | 0 | CH₃ | CH₃ | 4-Cl | H |
| CH₃ | H | H | 0 | C₂H₅ | CH₃ | 4-CH₃ | H |
| CH₃ | H | H | 0 | C₂H₅ | CH₃ | 4-CH₃ | H |
| CH₃ | H | H | 0 | C₂H₅ | CH₃ | 4-C₂H₅ | H |
| CH₃ | H | H | 0 | C₂H₅ | C₂H₅ | 4-C₂H₅ | H |
| CH₃ | H | H | 0 | C₂H₅ | CH3 | 4-Cl | H |
| CH₃ | H | H | 0 | C₂H₅ | C₂H₅ | 4-Cl | H |
| CH₃ | H | H | 0 | C₂H₅ | CH₃ | 4-Br | H |
| CH₃ | H | H | 0 | C₂H₅ | C₂H₅ | 4-Br | H |
| CH₃ | H | H | 0 | C₂H₅ | Cl | 4-CH₃ | H |
| CH₃ | H | H | 0 | C₂H₅ | Br | 4-CH₃ | H |
| CH₃ | H | H | 0 | C₂H₅ | Cl | 4-Cl | H |
| CH₃ | H | H | 0 | C₂H₅ | Br | 4-Br | H |
| CH₃ | H | H | 0 | C₂H₅ | Cl | 4-Br | H |
| CH₃ | H | H | 0 | C₂H₅ | Br | 4-Cl | H |
| CH₃ | H | H | 0 | OCH₃ | CH₃ | 4-Cl | H |
| CH₃ | H | H | 0 | OCH₃ | C₂H₅ | 4-Cl | H |
| CH₃ | H | H | 0 | OC₂H₅ | CH₃ | 4-Cl | H |
| CH₃ | H | H | 0 | OC₂H₅ | C₂H₅ | 4-Cl | H |
| CH₃ | H | H | 0 | Cl | OCH₃ | 4-CH₃ | H |
| CH₃ | H | H | 0 | Cl | OC₂H₅ | 4-CH₃ | H |
| CH₃ | H | H | 0 | CH₃ | CH₃ | 4-Cl | H |
| CH₃ | H | H | 0 | Cl | H | 4-Cl | 5-Cl |
| CH₃ | H | H | 0 | CH₃ | H | 4-CH₃ | 5-CH₃ |
| CH₃ | H | H | 0 | CH₃ | H | 4-Cl | 5-CH₃ |
| CH₃ | H | H | 0 | Br | H | 4-Cl | 5-CH₃ |
| CH₃ | H | H | 0 | Br | H | 4-CH₃ | 5-CH₃ |
| CH₃ | H | H | 0 | CH₃ | H | 4-Br | 5-CH₃ |
| CH₃ | H | H | 0 | Cl | H | 4-Cl | 5-CH₃ |
| CH₃ | H | H | 0 | CH₃ | H | 4-Br | 5-CH3 |
| CH₃ | H | H | 0 | Cl | H | 4-CH₃ | 5-Cl |
| CH₃ | H | H | 0 | CH₃ | H | H | 5-CH₃ |

TABLE 11-continued (I-2-a)

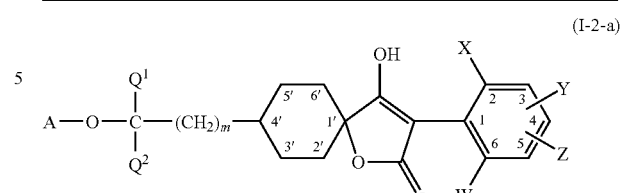

| A | Q¹ | Q² | m | X | W | Y | Z |
|---|---|---|---|---|---|---|---|
| CH₃ | H | H | 0 | Cl | H | H | 5-CH₃ |
| CH₃ | H | H | 0 | Br | H | H | 5-CH₃ |
| CH₃ | H | H | 0 | CH₃ | H | H | 5-Cl |
| CH₃ | H | H | 0 | CH₃ | H | H | 5-Br |
| CH₃ | H | H | 0 | CH₃ | CH₃ | 4-CH₃ | 5-CH₃ |
| CH₃ | H | H | 0 | CH₃ | CH₃ | 4-CH₃ | 5-Cl |
| CH₃ | H | H | 0 | CH₃ | CH₃ | 4-CH₃ | 5-Br |
| CH₃ | H | H | 0 | CH₃ | CH₃ | H | 3-Cl |
| CH₃ | H | H | 0 | CH₃ | CH₃ | H | 3-Br |
| CH₃ | H | H | 0 | Cl | Cl | H | 3-Br |
| CH₃ | H | H | 0 | CH₃ | CH₃ | 4-(4-Cl—C₆H₄) | H |
| CH₃ | H | H | 0 | C₂H₅ | CH₃ | 4-(4-Cl—C₆H₄) | H |
| CH₃ | H | H | 0 | C₂H₅ | C₂H₅ | 4-(4-Cl—C₆H₄) | H |
| CH₃ | H | H | 0 | Cl | CH₃ | 4-(4-Cl—C₆H₄) | H |
| CH₃ | H | H | 0 | Cl | C₂H₅ | 4-(4-Cl—C₆H₄) | H |
| CH₃ | H | H | 0 | CH₃ | H | 5-(4-Cl—C₆H₄) | H |
| CH₃ | H | H | 0 | CH₃ | CH₃ | 5-(4-Cl—C₆H₄) | H |
| CH₃ | H | H | 0 | CH₃ | H | 5-(4-Cl—C₆H₄) | 4-CH₃ |
| CH₃ | H | H | 0 | CH₃ | CH₃ | 5-(4-Cl—C₆H₄) | 4-CH₃ |
| CH₃ | H | H | 0 | Cl | H | 5-(4-Cl—C₆H₄) | H |
| CH₃ | H | H | 0 | I | H | H | H |
| CH₃ | H | H | 0 | I | H | 4-CH₃ | H |
| CH₃ | H | H | 0 | I | CH₃ | H | H |
| CH₃ | H | H | 0 | I | C₂H₅ | H | H |
| CH₃ | H | H | 0 | CH₃ | H | H | 5-I |
| CH₃ | H | H | 0 | CH₃ | H | 4-CH₃ | 5-I |
| CH₃ | H | H | 0 | I | CH₃ | 4-CH₃ | H |
| CH₃ | H | H | 0 | I | C₂H₅ | 4-CH₃ | H |
| CH₃ | H | H | 0 | I | CH₃ | 4-Cl | H |
| CH₃ | H | H | 0 | I | C₂H₅ | 4-Cl | H |
| CH₃ | H | H | 0 | I | Cl | 4-CH₃ | H |
| CH₃ | H | H | 0 | I | H | 4-CH₃ | 5-CH₃ |
| CH₃ | H | H | 0 | CH₃ | H | 4-I | H |
| CH₃ | H | H | 0 | C₂H₅ | H | 4-I | H |
| CH₃ | H | H | 0 | CH₃ | CH₃ | 4-I | H |
| CH₃ | H | H | 0 | C₂H₅ | CH₃ | 4-I | H |
| CH₃ | H | H | 0 | C₂H₅ | C₂H₅ | 4-I | H |
| CH₃ | H | H | 0 | Cl | CH₃ | 4-I | H |
| CH₃ | H | H | 0 | Cl | C₂H₅ | 4-I | H |
| CH₃ | H | H | 0 | CH₃ | H | 4-I | 5-CH₃ |
| CH₃ | H | H | 0 | CH₃ | CH₃ | H | 3-I |
| CH₃ | H | H | 0 | I | H | H | 5-CH₃ |

TABLE 12

A, m, Q¹, Q², W, X, Y and Z as stated in Table 11 where A—O—C(Q¹)(Q²)—(CH₂)ₘ— is in the 3' position

Table 13: m, Q¹, Q², W, X, Y and Z as stated in Table 11

A=C₂H₅

TABLE 14

A, m, $Q^1$, $Q^2$, W, X, Y and Z as stated in Table 13

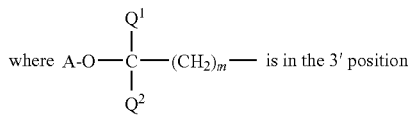 where A—O—$\overset{Q^1}{\underset{Q^2}{C}}$—$(CH_2)_m$— is in the 3' position Table 15: m, $Q^1$, $Q^2$, $Q^1$, $Q^2$, W, X, Y and Z as stated in Table 11
A=n-$C_3H_7$

TABLE 16

A, m, $Q^1$, $Q^2$, W, X, Y and Z as stated in Table 15

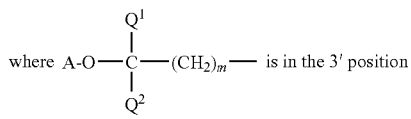 where A—O—$\overset{Q^1}{\underset{Q^2}{C}}$—$(CH_2)_m$— is in the 3' position Table 17: A, $Q^1$, $Q^2$, W, X, Y and Z as stated in Table 11 where m=1

TABLE 18

A, $Q^1$, $Q^2$, W, X, Y and Z as stated in Table 11

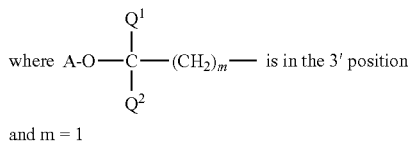 where A—O—$\overset{Q^1}{\underset{Q^2}{C}}$—$(CH_2)_m$— is in the 3' position
and m = 1

Table 19: $Q^1$, $Q^2$, W, X, Y and Z as stated in Table 11 where m=1 and A=$C_2H_5$

TABLE 20

$Q^1$, $Q^2$, W, X, Y and Z as stated in Table 11

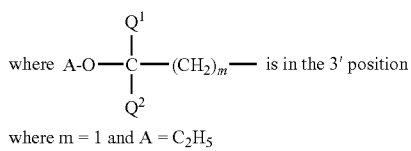 where A—O—$\overset{Q^1}{\underset{Q^2}{C}}$—$(CH_2)_m$— is in the 3' position where m = 1 and A = $C_2H_5$ Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

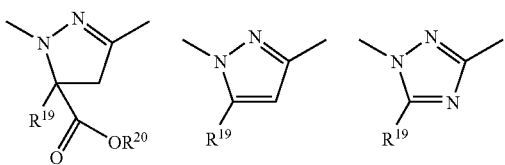

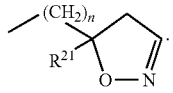

n preferably represents the numbers 0, 1, 2, 3 or 4.

$A^2$ preferably represents in each case optionally methyl-, ethyl-, methoxycarbonyl-, ethoxycarbonyl- or allyloxycarbonyl-substituted methylene or ethylene.

$R^{14}$ preferably represents hydroxyl, mercapto, amino, methoxy, ethoxy, n- or i-propoxy, n, i, s- or t-butoxy, methylthio, ethylthio, n- or i-propylthio, n, i, s- or t-butylthio, methylamino, ethylamino, n- or i-propylamino, n, i, s- or t-butylamino, dimethylamino or diethylamino.

$R^{15}$ preferably represents hydroxyl, mercapto, amino, methoxy, ethoxy, n- or i-propoxy, n, i, s- or t-butoxy, 1-methylhexyloxy, allyloxy, 1-allyloxymethylethoxy, methylthio, ethylthio, n- or i-propylthio, n, i, s- or t-butylthio, methylamino, ethylamino, n- or i-propylamino, n, i, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n, i, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n, i, s- or t-butyl-substituted phenyl.

$R^{18}$ preferably represents hydrogen, in each case optionally fluorine- and/or chlorine-substituted methyl, ethyl, n- or i-propyl, n, i, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n, i, s- or t-butyl-substituted phenyl, or together with $R^{17}$ represents one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{20}$ preferably represents hydrogen, in each case optionally hydroxyl-, cyano-, fluorine-, chlorine-, methoxy-, ethoxy-, n- or i-propoxy-substituted methyl, ethyl, n- or i-propyl, n, i, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n, i, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n, i, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n, i, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n, i, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n, i, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

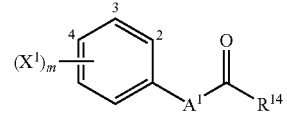

(IIa)

| Example No. | (Positions) $(X^1)_m$ | $A^1$ | $R^{14}$ |
|---|---|---|---|
| IIa-1 | (2) Cl, (4) Cl | pyrazoline with H₃C, C(O)OCH₃ | OCH₃ |
| IIa-2 | (2) Cl, (4) Cl | pyrazoline with H₃C, C(O)OC₂H₅ | OCH₃ |
| IIa-3 | (2) Cl, (4) Cl | pyrazoline with H₃C, C(O)OCH₃ | OC₂H₅ |
| IIa-4 | (2) Cl, (4) Cl | pyrazoline with H₃C, C(O)OC₂H₅ | OC₂H₅ |
| IIa-5 | (2) Cl | pyrazole with phenyl | OCH₃ |
| IIa-6 | (2) Cl, (4) Cl | pyrazole with phenyl | OCH₃ |
| IIa-7 | (2) F | pyrazole with phenyl | OCH₃ |

TABLE-continued

Examples of the compounds of the formula (IIa)

(IIa)

| Example No. | (Positions) $(X^1)_m$ | $A^1$ | $R^{14}$ |
|---|---|---|---|
| IIa-8 | (2) F | 1-methyl-3-methyl-5-(2-chlorophenyl)pyrazole | $OCH_3$ |
| IIa-9 | (2) Cl, (4) Cl | 1-methyl-3-methyl-5-trichloromethyl-1,2,4-triazole | $OC_2H_5$ |
| IIa-10 | (2) Cl, (4) $CF_3$ | 1-methyl-3-methyl-5-phenyl-1,2,4-triazole | $OCH_3$ |
| IIa-11 | (2) Cl | 1-methyl-3-methyl-5-(2-fluorophenyl)pyrazole | $OCH_3$ |
| IIa-12 | — | 3-methyl-5-methyl-5-phenyl-4,5-dihydroisoxazole | $OC_2H_5$ |
| IIa-13 | (2) Cl, (4) Cl | 1-methyl-5-methylpyrazole | $OC_2H_5$ |
| IIa-14 | (2) Cl, (4) Cl | 1-methyl-3-methyl-5-isopropylpyrazole | $OC_2H_5$ |
| IIa-15 | (2) Cl, (4) Cl | 1-methyl-3-methyl-5-tert-butylpyrazole | $OC_2H_5$ |
| IIa-16 | (2) Cl, (4) Cl | 3-methyl-5-ethyl-4,5-dihydroisoxazole | $OC_2H_5$ |
| IIa-17 | (2) Cl, (4) Cl | 3,5-dimethyl-4,5-dihydroisoxazole | $OC_2H_5$ |
| IIa-18 | — | 3-methyl-5-methyl-5-phenyl-4,5-dihydroisoxazole | OH |

Examples of the compounds of the formula (IIb) which are very particularly preferred as herbicide safeners according to the invention are listed in the table below.

TABLE

Examples of the compounds of the formula (IIb)

(IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |

TABLE-continued

Examples of the compounds of the formula (IIb)

(IIb)

| Example No. | X² (Position) | X³ (Position) | A² | R¹⁵ |
|---|---|---|---|---|
| IIb-11 | (5) Cl | — | CH₂ | OC₄H₉-i |
| IIb-12 | (5) Cl | — | CH₂ | OCH(CH₃)OCH₂CH(OCH₂)CH=CH₂ |
| IIb-13 | (5) Cl | — | CH(CH₂OCH₂CH=CH₂)CH₂ | OC(=O)CH(CH₃)H |
| IIb-14 | (5) Cl | — | C₂H₅ | OC₂H₅ |
| IIb-15 | (5) Cl | — | CH₃ | OCH₃ |

Examples of the compounds of the formula (IIc) which are very particularly preferred as herbicide safeners according to the invention are listed in the table below.

TABLE (IIc)

Examples of the compounds of the formula (IIc)

| Example No. | R¹⁶ | N(R¹⁷,R¹⁸) |
|---|---|---|
| IIc-1 | CHCl₂ | N(CH₂CH=CH₂)₂ |
| IIc-2 | CHCl₂ | 3-methyl-2,2-dimethyl-oxazolidine |
| IIc-3 | CHCl₂ | 3-methyl-2,2-dimethyl-5-methyl-oxazolidine |
| IIc-4 | CHCl₂ | 1-methyl-1-oxa-4-azaspiro[4.5]decane |
| IIc-5 | CHCl₂ | 3-methyl-2,2-dimethyl-5-phenyl-oxazolidine |
| IIc-6 | CHCl₂ | 4-methyl-3-methyl-3,4-dihydro-2H-benzo[1,4]oxazine |
| IIc-7 | CHCl₂ | 3-methyl-2,2-dimethyl-5-(furan-2-yl)-oxazolidine |

Examples of the compounds of the formula (IId) which are very particularly preferred as herbicide safeners according to the invention are listed in the table below.

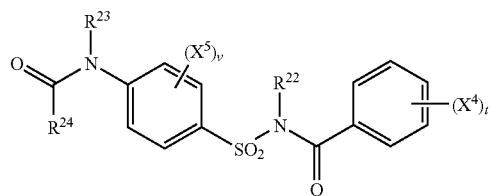

Examples of the compounds of the formula (IId)

| Example No. | R²² | R²³ | R²⁴ | (Positions) (X⁴)_t | (Positions) (X⁵)_y |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |
| IId-8 | H | H | C₃H₇-n | (2) OCH₃ (5) CH₃ | — |
| IId-9 | H | H | C₃H₇-i | (2) OCH₃ (5) CH₃ | — |
| IId-10 | H | H | cyclopropyl | (2) OCH₃ (5) CH₃ | — |
| IId-11 | H | H | OCH₃ | (2) OCH₃ (5) CH₃ | — |
| IId-12 | H | H | OC₂H₅ | (2) OCH₃ (5) CH₃ | — |
| IId-13 | H | H | OC₃H₇-i | (2) OCH₃ (5) CH₃ | — |
| IId-14 | H | H | SCH₃ | (2) OCH₃ (5) CH₃ | — |
| IId-15 | H | H | SC₂H₅ | (2) OCH₃ (5) CH₃ | — |
| IId-16 | H | H | SC₃H₇-i | (2) OCH₃ (5) CH₃ | — |
| IId-17 | H | H | NHCH₃ | (2) OCH₃ (5) CH₃ | — |
| IId-18 | H | H | NHC₂H₅ | (2) OCH₃ (5) CH₃ | — |
| IId-19 | H | H | NHC₃H₇-i | (2) OCH₃ (5) CH₃ | — |
| IId-20 | H | H | NH-cyclopropyl | (2) OCH₃ (5) CH₃ | — |
| IId-21 | H | H | NHCH₃ | (2) OCH₃ | — |
| IId-22 | H | H | NHC₃H₇-i | (2) OCH₃ | — |
| IId-23 | H | H | N(CH₃)₂ | (2) OCH₃ | — |
| IId-24 | H | H | N(CH₃)₂ | (3) CH₃ (4) CH₃ | — |
| IId-25 | H | H | CH₂—O—CH₃ | (2) OCH₃ | — |

Examples of the compounds of the formula (IIe) which are very particularly preferred as herbicide safeners according to the invention are listed in the table below.

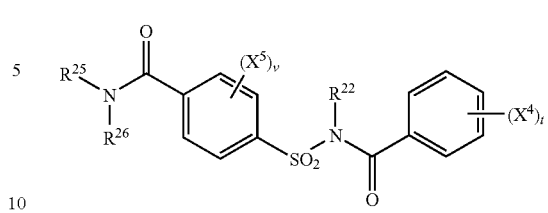

Examples of the compounds of the formula (IIe)

| Example No. | R²² | R²⁵ | R²⁶ | (Positions) (X⁴)_t | (Positions) (X⁵)_y |
|---|---|---|---|---|---|
| IIe-1 | H | H | CH₃ | (2) OCH₃ | — |
| IIe-2 | H | H | C₂H₅ | (2) OCH₃ | — |
| IIe-3 | H | H | C₃H₇-n | (2) OCH₃ | — |
| IIe-4 | H | H | C₃H₇-i | (2) OCH₃ | — |
| IIe-5 | H | H | cyclopropyl | (2) OCH₃ | — |
| IIe-6 | H | CH₃ | CH₃ | (2) OCH₃ | — |
| IIe-7 | H | H | CH₃ | (2) OCH₃ (5) CH₃ | — |
| IIe-8 | H | H | C₂H₅ | (2) OCH₃ (5) CH₃ | — |
| IIe-9 | H | H | C₃H₇-n | (2) OCH₃ (5)CH₃ | — |
| IIe-10 | H | H | C₃H₇-i | (2) OCH₃ (5) CH₃ | — |
| IIe-11 | H | H | cyclopropyl | (2) OCH₃ (5) CH₃ | — |
| IIe-12 | H | CH₃ | CH₃ | (2) OCH₃ (5) CH₃ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and II-11, and particular emphasis is given to cloquintocet-mexyl and mefenpyr-diethyl, and also isoxadifen-ethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in the table below.

TABLE

Examples of combinations according to the invention

| Active compounds of the formula (I) | Safener |
| --- | --- |
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |
| I-1-g | IIe-5 |
| I-1-g | IIe-11 |

TABLE

Examples of combinations according to the invention

| Active compounds of the formula (I) | Safener |
| --- | --- |
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-11 |
| I-2-a | IIe-5 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-11 |
| I-2-b | IIe-5 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-11 |
| I-2-d | IIe-5 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |

TABLE-continued

Examples of combinations according to the invention

| Active compounds of the formula (I) | Safener |
|---|---|
| I-2-f | cumyluron |
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

Surprisingly, it has now been found that the active compound combinations, defined above, of substituted cyclic ketoenols of the general formula (I) and safeners (antidotes) from group (b') listed above, whilst being very well tolerated by useful plants, have a particularly high herbicidal activity and can be used in various crops, in particular in cereals (especially wheat), but also in soya beans, potatoes, maize and rice, for the selective control of weeds.

Here, it has to be considered surprising that, from a large number of known safeners or antidotes capable of antagonizing the harmful effect of a herbicide on crop plants, those suitable are in particular the compounds of group (b') listed above which eliminate the harmful effect of substituted cyclic ketoenols on the crop plants virtually completely without having a major adverse effect on the herbicidal activity against the weeds.

Emphasis may be given here to the particularly advantageous effect of the particularly and most preferred combination partners from group (b'), in particular with respect to sparing cereal plants, such as, for example, wheat, barley and rye, but also maize and rice, as crop plants.

Using, for example, according to process (A) ethyl N-[(4-chloro-2,6-dimethyl)phenylacetyl]-1-amino-3-methoxymethylcyclohexanecarboxylate as starting material, the course of the process according to the invention can be represented by the reaction scheme below:

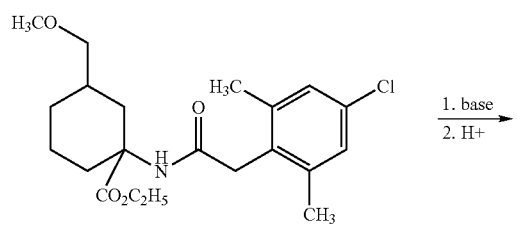

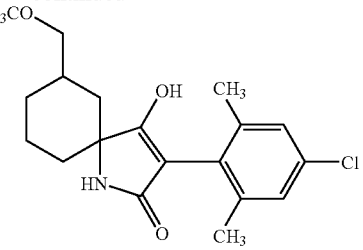

Using, for example, according to process (B) ethyl O-[(2-chloro-6-methyl)phenylacetyl]-1-hydroxy-3-methoxymethylcyclohexanecarboxylate, the course of the process according to the invention can be represented by the reaction scheme below:

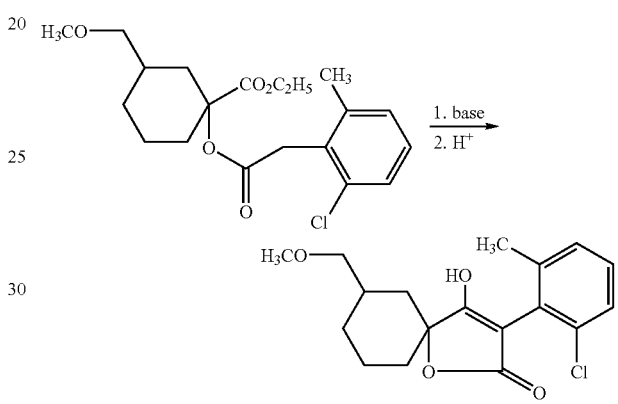

Using, for example, according to process (Cα) 8-methoxymethyl-3-[(4-chloro-2,6-dimethyl)phenyl]-1-azaspiro[4,5]decane-2,4-dione and pivaloyl chloride as starting materials, the course of the process according to the invention can be represented by the reaction scheme below:

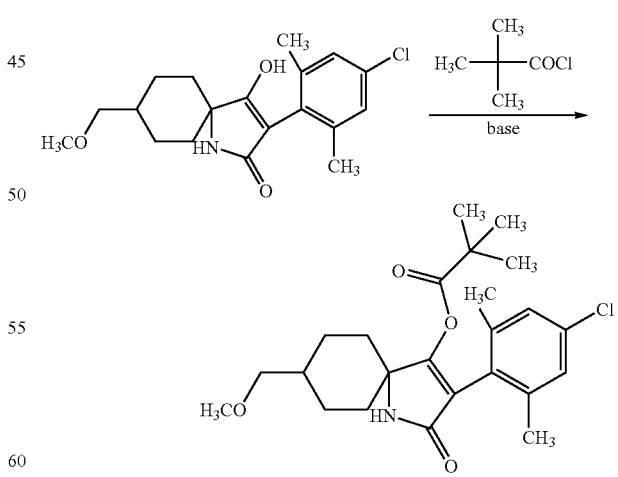

Using, for example, according to process (C) (variant β) 8-methoxymethyl-3-[(2,4-dichloro)phenyl]-1-oxaspiro[4,5]decane-2,4-dione and acetic anhydride as starting materials, the course of the process according to the invention can be represented by the reaction scheme below:

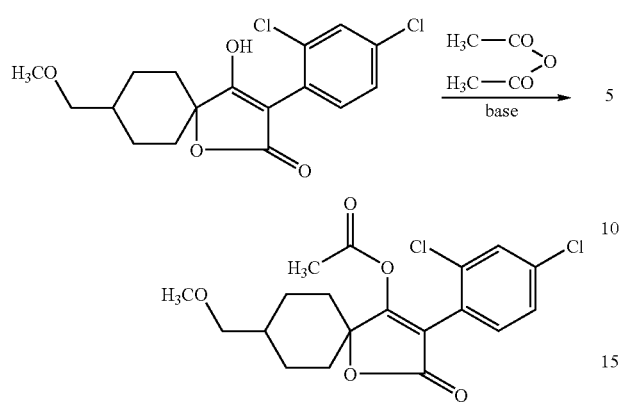

Using, for example, according to process (D) 7-methoxymethyl-3-[(2,4-dichloro-6-methyl)phenyl]-1-azaspiro[4,5]decane-2,4-dione and ethyl chloroformate as starting compounds, the course of the process according to the invention can be represented by the reaction scheme below:

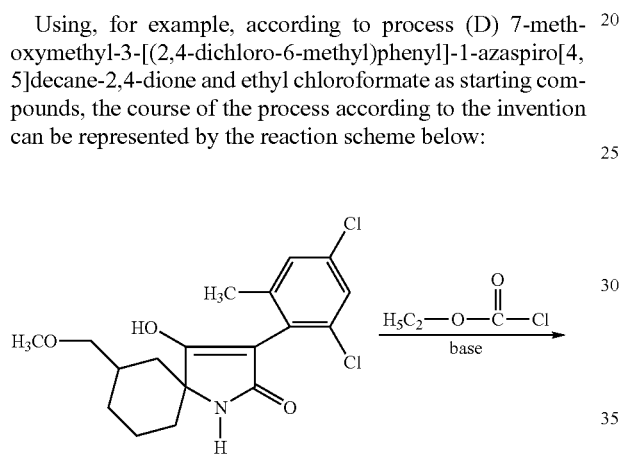

Using, for example, according to process (E) 7-methoxymethyl-3-[(2,4,6-trimethyl)phenyl]-1-oxaspiro[4,5]decane-2,4-dione and methyl chloromonothioformate as starting materials, the course of the reaction can be represented as follows:

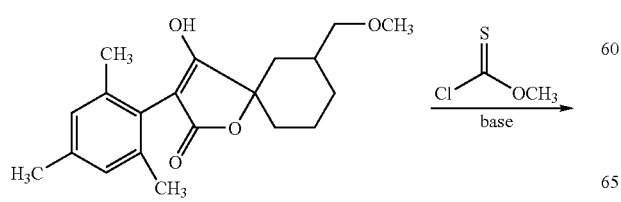

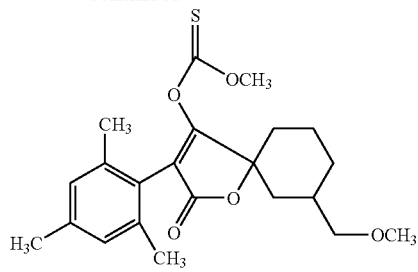

Using, for example, according to process (F) 8-methoxymethyl-3-[(2,4,6-trimethyl)phenyl]-1-azaspiro[4,5]decane-2,4-dione and methanesulphonyl chloride as starting materials, the course of the reaction can be represented by the reaction scheme below:

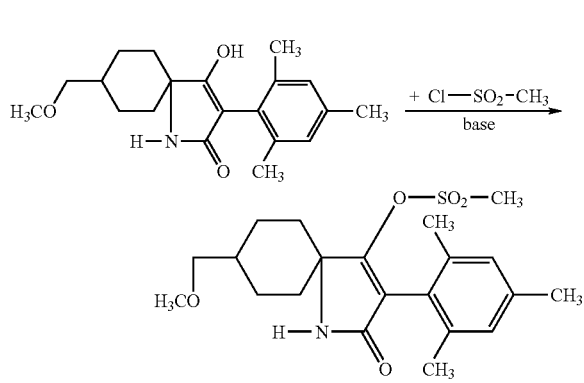

Using, for example, according to process (G) 7-methoxymethyl-3-[(2,4-dichloro-6-methyl)phenyl]-1-oxaspiro[4,5]decane-2,4-dione and 2,2,2-trifluoroethyl methanethiophosphonyl chloride as starting materials, the course of the reaction can be represented by the reaction scheme below:

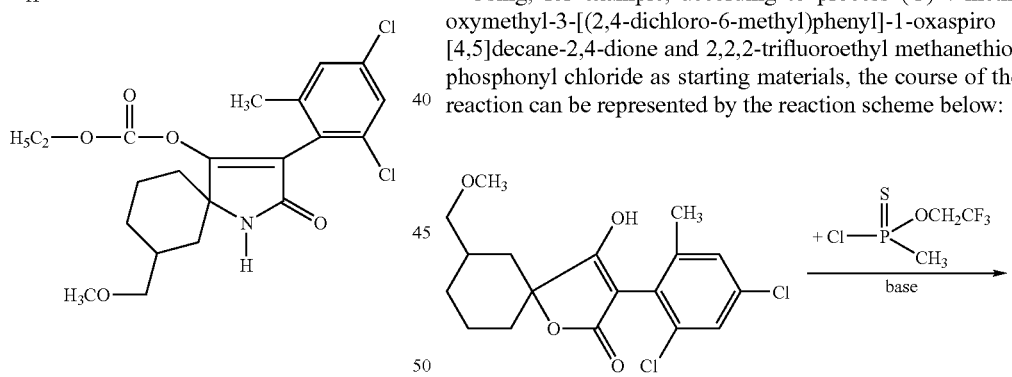

Using, for example, according to process (H) 7-methoxymethyl-3-[(2,3,4,6-tetramethylphenyl]-1-azaspiro[4,5]decane-2,4-dione and NaOH as components, the course of the process according to the invention can be represented by the reaction scheme below:

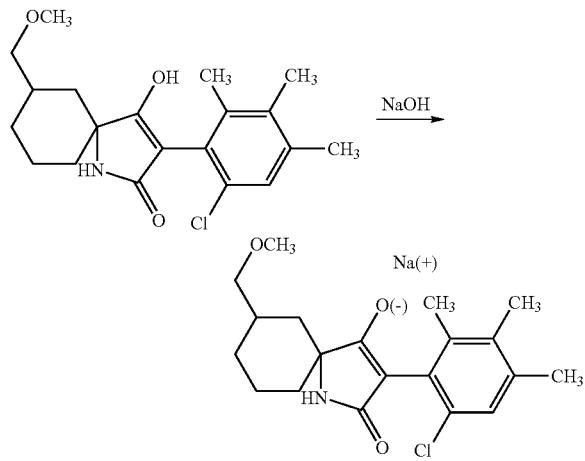

Using, for example, according to process (I) (variant α) 7-methoxymethyl-3-[(2,4,5-trimethyl)phenyl]-1-oxaspiro[4,5]decane-2,4-dione and ethyl isocyanate as starting materials, the course of the reaction can be represented by the reaction scheme below:

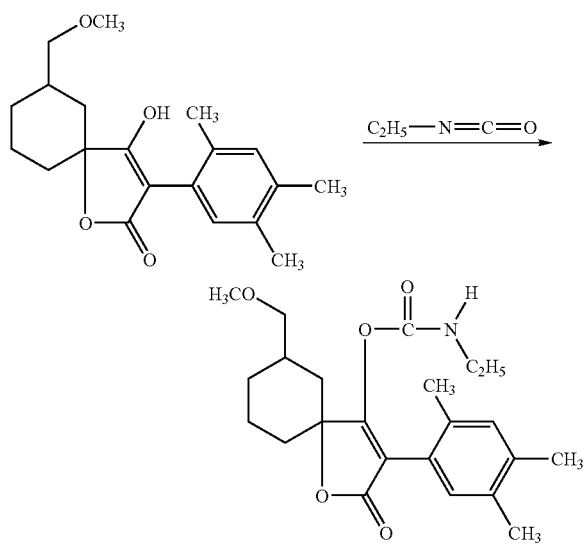

Using, for example, according to process (I) (variant β) 7-propoxymethyl-3-[(2,4,6-trimethyl)phenyl]-1-azaspiro[4,5]decane-2,4-dione and dimethylcarbamoyl chloride as starting materials, the course of the reaction can be represented by the reaction scheme below:

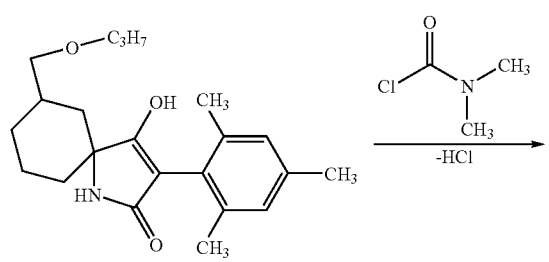

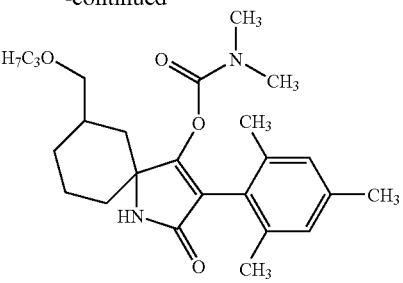

The compounds, required as starting materials in the process (A) according to the invention, of the formula (II)

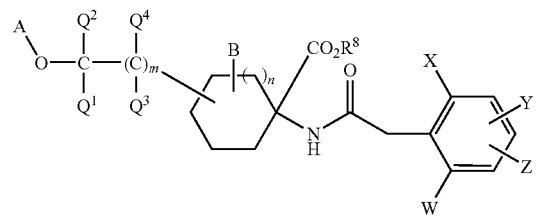

(II)

in which

A, B, m, n, $Q^1$, $Q^2$, $Q^3$, $Q^4$, W, X, Y, Z and $R^8$ are as defined above, are novel.

The acylamino acid esters of the formula (II) are obtained, for example, when amino acid derivatives of the formula (XIV)

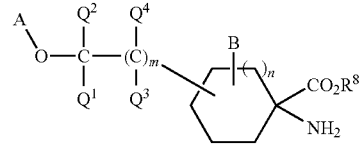

(XIV)

in which

A, B, m, n, $Q^1$, $Q^2$, $Q^3$, $Q^4$, W, X, Y, Z and $R^8$ are as defined above, are acylated with substituted phenylacetic acid derivatives of the formula (XV)

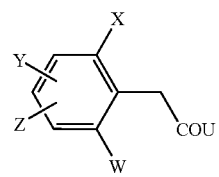

(XV)

in which

W, X, Y and Z are as defined above and

U represents a leaving group introduced by reagents for activating carboxylic acids, such as carbonyldiimidazole, carbodiimides (such as, for example, dicyclohexylcarbodiimide), phosphorylating reagents (such as, for example, $POCl_3$, BOP-Cl), halogenating agents, such as, for example, thionyl chloride, oxalyl chloride, phosgene or chloroformic esters, (Chem. Reviews 52, 237-416 (1953); Bhattacharya, Indian J. Chem. 6, 341-5, 1968)

or when acylamino acids of the formula (XVI)

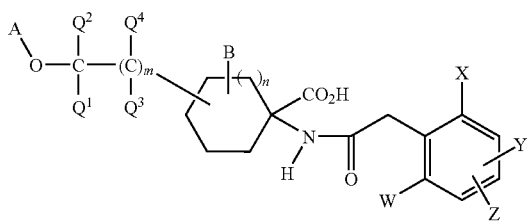
(XVI)

in which

A, B, m, n, $Q^1$, $Q^2$, $Q^3$, $Q^4$, W, X, Y and Z are as defined above, are esterified (Chem. Ind. (London) 1568 (1968)).

The compounds of the formula (XVI)

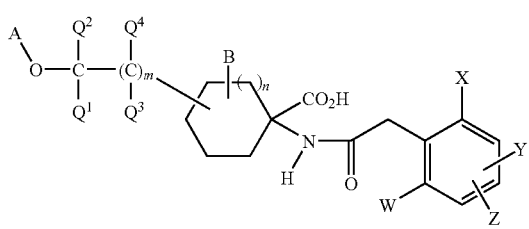
(XVI)

in which

A, B, m, n, $Q^1$, $Q^2$, $Q^3$, $Q^4$, W, X, Y and Z are as defined above, are novel.

The compounds of the formula (XVI) are obtained, for example, when 1-aminocyclohexanecarboxylic acids of the formula (XVII)

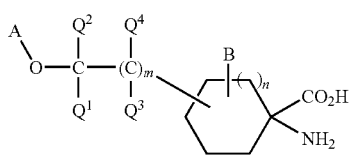
(XVII)

in which

A, B, m, n, $Q^1$, $Q^2$, $Q^3$ and $Q^4$ are as defined above are acylated according to Schotten-Baumann (Organikum, VEB Deutscher Verlag der Wissen-schaften, Berlin 1977, p. 505) with substituted phenylacetic acid derivatives of the formula (XV)

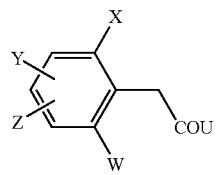
(XV)

in which

U, W, X, Y and Z are as defined above.

Some of the compounds of the formula (XV) are known, and/or they can be prepared by the known processes of the published specifications cited at the outset.

The compounds of the formulae (XIV) and (XVII) are novel and can be prepared by known processes (see, for example, Compagnon, Ann. Chim. (Paris) [14] 5, pp. 11-22, 23-27 (1970), L. Munday, J. Chem. Soc. 4372 (1961); J. T. Eward, C. Jitrangeri, Can. J. Chem. 53, 3339 (1975)).

The novel 1-aminocyclohexanecarboxylic acids (XVII) can generally be obtained by the Bucherer-Bergs synthesis or by the Strecker synthesis, where they are in each case obtained in different isomeric forms. For the sake of simplicity, hereinbelow the isomers in which the 3-substituent or 4-substituent and the amino group are in equatorial/axial or axial/equatorial positions are referred to as β. For the sake of simplicity, hereinbelow the isomers in which the amino group and the 3-substituent are in equatorial/equatorial or axial/axial positions are referred to as α.

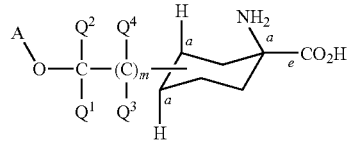

Example: β isomer (L. Munday, *J. Chem. Soc.* 4372 (1961)1

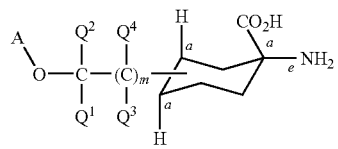

Example: α isomer

Furthermore, the starting materials, used in the above process (A), of the formula (II)

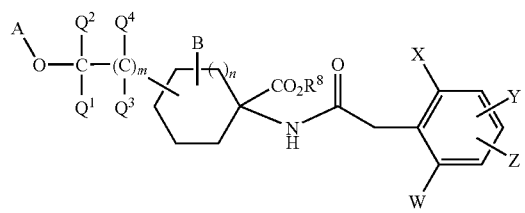
(II)

in which

A, B, m, n, $Q^1$, $Q^2$, $Q^3$, $Q^4$, W, X, Y, Z and $R^8$ are as defined above can be prepared by reacting 1-aminocyclohexanecarbonitriles of the formula (XVIII)

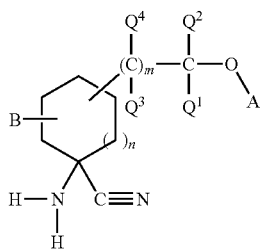
(XVIII)

in which

A, B, m, n, $Q^1$, $Q^2$, $Q^3$ and $Q^4$ are as defined above, with substituted phenylacetic acid derivatives of the formula (XV)

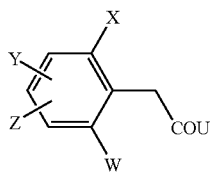
(XV)

in which

U, W, X, Y and Z are as defined above to give compounds of the formula (XIX)

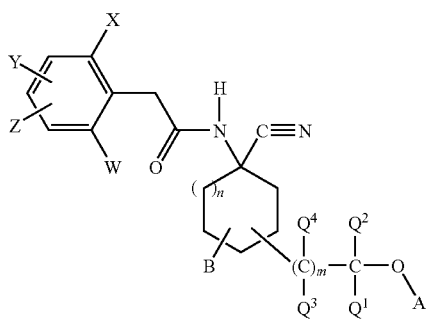
(XIX)

in which

A, B, m, n, $Q^1$, $Q^2$, $Q^3$, $Q^4$, W, X, Y and Z are as defined above and subjecting these subsequently to an acidic alcoholysis.

The compounds of the formula (XIX) are likewise novel. The compounds of the formula (XVIII) are likewise novel and can be prepared as described, for example, in EP-A-595 130.

The compounds, required as starting materials in the process (B) according to the invention, of the formula (III)

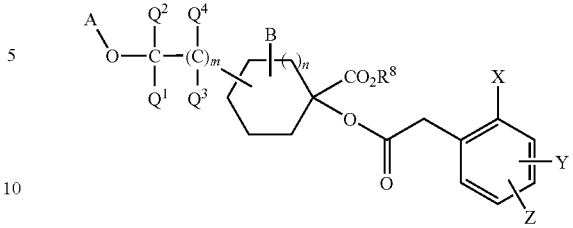
(III)

in which

A, B, m, n, $Q^1$, $Q^2$, $Q^3$, $Q^4$, W, X, Y, Z and $R^8$ are as defined above are novel.

They can be prepared in a simple manner by methods known in principle.

The compounds of the formula (III) are obtained, for example, when 1-hydroxycyclohexanecarboxylic esters of the formula (XX)

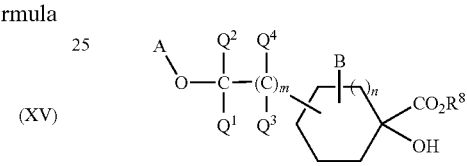
(XX)

in which

A, B, m, n, $Q^1$, $Q^2$, $Q^3$, $Q^4$ and $R^8$ are as defined above are acylated with substituted phenylacetic acid derivatives of the formula (XV)

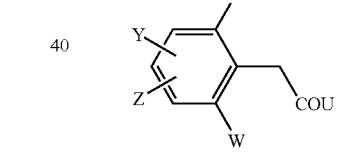
(XV)

in which

U, W, X, Y and Z are as defined above (Chem. Reviews 52, 237-416 (1953)).

The 1-hydroxy-3-alkoxycyclohexylcarboxylic esters of the formula (XX) are novel. They are obtained, for example, by reacting substituted 1-hydroxy-3-alkoxycyclohexanecarbonitriles in the presence of acids, for example according to Pinner, with alcohols. The cyanohydrin is obtained, for example, by reacting substituted 3-alkoxycyclohexan-1-ones with hydrocyanic acid.

The acid halides of the formula (IV), carboxylic anhydrides of the formula (V), chloroformic esters or chloroformic thioesters of the formula (VI), chloromonothioformic esters or chlorodithio-formic esters of the formula (VII), sulphonyl chlorides of the formula (VIII), phosphorus compounds of the formula (IX) and metal hydroxides, metal alkoxides or amines of the formulae (X) and (XI), respectively, and isocyanates of the formula (XII) and carbamoyl chlorides of the formula (XIII) furthermore required as starting materials for carrying out the processes (C), (D), (E), (F), (G), (H) and (I) according to the invention are generally known compounds of organic or inorganic chemistry.

In addition, the compounds of the formula (XV) are known from the patent applications cited at the outset and/or can be prepared by the methods given therein.

The process (A) is characterized in that compounds of the formula (II) in which A, B, m, n, $Q^1$, $Q^2$, $Q^3$, $Q^4$, W, X, Y, Z and $R^8$ are as defined above are subjected to an intramolecular condensation in the presence of a diluent and in the presence of a base.

Suitable diluents for use in the process (A) according to the invention are all organic solvents inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperature may be varied within a relatively wide range. In general, the process is carried out at temperatures between −75® C. and 200° C., preferably between −50° C. and 150° C.

The process (A) is generally carried out under atmospheric pressure.

When carrying out the process (A) according to the invention, the reaction component of the formula (II) and the deprotonating base are generally employed in equimolar to about doubly equimolar amounts. However, it is also possible to use a relatively large excess (up to 3 mol) of one component or the other.

The process (B) is characterized in that compounds of the formula (III), in which A, B, m, n, $Q^1$, $Q^2$, $Q^3$, $Q^4$, W, X, Y, Z and $R^8$ are as defined above are condensed intramolecularly in the presence of a diluent and in the presence of a base.

Suitable diluents for use in the process (B) according to the invention are all organic solvents inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, use may be made of alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperature may be varied within a relatively wide range. In general, the process is carried out at temperatures between −75® C. and 200° C., preferably between −50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for use in the process ($C_\alpha$) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. If the acid halide is sufficiently stable to hydrolysis, the reaction can also be carried out in the presence of water.

Suitable acid binders for the reaction according to process ($C_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process ($C_\alpha$) according to the invention can be varied within a relatively wide range. In general, the process is carried out at temperatures between −20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of the carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Suitable diluents for use in the process ($C_\beta$) according to the invention are, preferably, the diluents which are also preferred when using acid halides. Besides, excess carboxylic anhydride may simultaneously act as diluent.

Suitable acid binders, which are added, if appropriate, for process ($C_\beta$) are, preferably, the acid binders which are also preferred when using acid halides.

The reaction temperature in the process ($C_\beta$) according to the invention may be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable binders for the process (D) according to the invention are all customary acid acceptors.

Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (D) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulphoxide and sulpholane.

When carrying out the process (D) according to the invention, the reaction temperature can be varied within a relatively wide range. In general, the temperature is between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In preparation process (E), about 1 mol of chloromonothioformic ester or chlorodithioformic ester of the formula (VII) is employed per mole of the starting material of the formulae (I-1-a) to (I-2-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by addition of strong deprotonating agents, such as, for example, sodium hydride or potassium tert-butoxide, the further addition of acid binders may be dispensed with.

Suitable bases for use in the process (E) are all customary proton acceptors. Preference is given to using alkali metal hydrides, alkali metal alkoxides, alkali metal or alkaline earth metal carbonates or bicarbonates or nitrogen bases. Sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU) may be mentioned by way of example.

The reaction may be carried out at atmospheric pressure or under elevated pressure and is preferably carried out at atmospheric pressure. Work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In preparation process (F), about 1 mol of sulphonyl chloride of the formula (VIII) is reacted per mole of the starting material of the formula (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethylformamide, ethyl acetate, methylene chloride.

If, in a preferred embodiment, the enolate salt of the compounds (I-1-a) to (I-2-a) is prepared by addition of strongly deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In preparation process (G), to obtain compounds of the formulae (I-1-e) to (I-2-e), from 1 to 2, preferably from 1 to 1.3, mol of the phosphorus compound of the formula (IX) are reacted per mole of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Suitable diluents for use in the process (H) according to the invention are, preferably, ethers, such as tetrahydrofuran, dioxane, diethyl ether, or else alcohols, such as methanol, ethanol, isopropanol, and also water. The process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In preparation process (Iα), about 1 mol of isocyanate of the formula (XII) is reacted per mole of starting material of the formulae (I-1-a) to (I-2-a), at from 0 to 100° C., preferably from 20 to 50° C.

The process (Iα) is preferably carried out in the presence of a diluent.

Suitable diluents are all inert organic solvents, such as aromatic hydrocarbons, halogenated hydrocarbons, ethers, amides, nitrites, sulphones or sulphoxides.

If appropriate, catalysts may be added to accelerate the reaction. Suitable for use as catalysts are, very advantageously, organotin compounds, such as, for example, dibutyltin dilaurate.

The reaction is preferably carried out at atmospheric pressure.

In preparation process (Iβ), about 1 mol of carbamoyl chloride of the formula (XIII) is reacted per mole of starting compound of the formulae (I-1-a) to (I-2-a), at from 0 to 150° C., preferably at from 20 to 70° C.

Suitable diluents which are added, if appropriate, are all inert polar organic solvents, such as ethers, carboxylic esters, nitrites, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhi-* noceros, *Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila,* *Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:

Inhibitors of Nucleic Acid Synthesis
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division
  benomyl, carbendazim, diethofencarb, fuberidazole, pencycuron, thiabendazole, thiophanatmethyl, zoxamide Inhibitors of Respiratory Chain Complex I
  diflumetorim Inhibitors of Respiratory Chain Complex II
  boscalid, carboxin, fenfuram, flutolanil, furametpyr, mepronil, oxycarboxin, penthiopyrad, thifluzamide Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin Decouplers
  dinocap, fluazinam Inhibitors of ATP Production
  fentin acetate, fentin chloride, fentin hydroxide, silthiofam Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil Inhibitors of Signal Transduction
  fenpiclonil, fludioxonil, quinoxyfen Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine,
  naftifine, pyributicarb, terbinafine Inhibitors of Cell Wall Synthesis
  benthiavalicarb, bialaphos, dimethomorph, flumorph, iprovalicarb, polyoxins, polyoxorim, validamycin A Inhibitors of Melanin Biosynthesis
  capropamid, diclocymet, fenoxanil, phthalid, pyroquilon, tricyclazole Resistance Inductors
  acibenzolar-S-methyl, probenazole, tiadinil Multisite
  captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
  amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl] pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino] oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alphapropynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl) amino]butanamide, 5-chloro-7-(4-methylpiperidin-1-yl)-6-(2,4,6-trifluorophenyl)[1,2,4]-triazolo[1,5-a] pyrimidine, 5-chloro-6-(2,4,6-trifluorophenyl)-N-[(1R)-1,2,2-trimethylpropyl]-[1,2,4]triazolo[1,5-a] pyrimidin-7-amine, 5-chloro-N-[(1R)-1,2-dimethylpropyl]-6-(2,4,6-trifluorophenyl)[1,2,4] triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-

(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphabenzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl) cyclopropanecarboxamide, 1-[(4-methoxyphenoxy) methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
   carbamates,
     for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
   organophosphates,
     for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
   pyrethroids,
     for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)

DDT
oxadiazines,
   for example indoxacarb
semicarbazones,
   for example metaflumizone (BAS3201)

Acetylcholine Receptor Agonists/Antagonists
   chloronicotinyls,
     for example acetamiprid, clothianidin, dinotefuran, imidacloprid, nitenpyram, nithiazine, thiacloprid, thiamethoxam
   nicotine, bensultap, cartap Acetylcholine Receptor Modulators
   spinosyns,
     for example spinosad GABA-Controlled Chloride Channel Antagonists
   organochlorines,
     for example camphechlor, chlordane, endosulphan, gamma-HCH, HCH, heptachlor, lindane, methoxychlor
   fiprols,
     for example acetoprole, ethiprole, fipronil, pyrafluprole, pyriprole, vaniliprole Chloride Channel Activators
   mectins,
     for example abamectin, emamectin, emamectin-benzoate, ivermectin, lepimectin, milbemycin Juvenile Hormone Mimetics,
     for example diofenolan, epofenonane, fenoxycarb, hydroprene, kinoprene, methoprene, pyriproxifen, triprene Ecdysone Agonists/Disruptors
   diacylhydrazines,
     for example chromafenozide, halofenozide, methoxyfenozide, tebufenozide Chitin Biosynthesis Inhibitors
   benzoylureas,
     for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
   buprofezin
   cyromazine Oxidative Phosphorylation Inhibitors, ATP Disruptors
   diafenthiuron
   organotin compounds,
     for example azocyclotin, cyhexatin, fenbutatin-oxide Oxidative Phosphorylation Decouplers Acting by Interrupting the H-Proton Gradient
   pyrroles,
     for example chlorfenapyr
   dinitrophenols,
     for example binapacryl, dinobuton, dinocap, DNOC, meptyldinocap Site-I Electron Transport Inhibitors
   METI's,
     for example fenazaquin, fenpyroximate, pyrimidifen, pyridaben, tebufenpyrad, tolfenpyrad hydramethylnon
dicofol
Site-II Electron Transport Inhibitors
    rotenone
Site-III Electron Transport Inhibitors
    acequinocyl, fluacrypyrim
Microbial Disruptors of the Insect Gut Membrane
    *Bacillus thuringiensis* strains
Lipid Synthesis Inhibitors
    tetronic acids,
    for example spirodiclofen, spiromesifen,
    tetramic acids,
    for example spirotetramat, cis-3-(2,5-dimethylphenyl)-4-hydroxy-8-methoxy-1-azaspiro[4.5]dec-3-en-2-one
    carboxamides,
    for example flonicamid
    octopaminergic agonists,
    for example amitraz
Inhibitors of Magnesium-Stimulated ATPase,
    propargite
    nereistoxin analogues,
    for example thiocyclam hydrogen oxalate, thiosultap-sodium
Agonists of the Ryanodine Receptor,
    benzodicarboxamides,
    for example flubendiamide
    anthranilamides,
    for example rynaxypyr (3-bromo-N-{4-chloro-2-methyl-6-[(methylamino)carbonyl]-phenyl}-1-(3-chloropyridin-2-yl)-1H-pyrazole-5-carboxamide)
Biologicals, Hormones or Pheromones
    azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
    fumigants,
    for example aluminium phosphide, methyl bromide, sulphuryl fluoride
    antifeedants,
    for example cryolite, flonicamid, pymetrozine
Mite growth inhibitors,
    for example clofentezine, etoxazole, hexythiazox
    amidoflumet, benclothiaz, benzoximate, bifenazate, bromopropylate, buprofezin, chinomethionat, chlordimeform, chlorobenzilate, chloropicrin, clothiazoben, cyclopene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecti-* cornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec. Tryptodendron spec. Apate monachus, Bostrychus capucins, Heterobostrychus brunneus, Sinoxylon spec. Dinoderus minutus;

Hymenopterons, such as Sirex juvencus, Urocerus gigas, Urocerus gigas taignus, Urocerus augur;

Termites, such as Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;

Bristletails, such as Lepisma saccharina.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, Buthus occitanus.

From the order of the Acarina, for example, Argas persicus, Argas reflexus, Bryobia spp., Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.

From the order of the Araneae, for example, Aviculariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, Blaniulus guttulatus, Polydesmus spp.

From the order of the Chilopoda, for example, Geophilus spp.

From the order of the Zygentoma, for example, Ctenolepisma spp., Lepisma saccharina, Lepismodes inquilinus.

From the order of the Blattaria, for example, Blatta orientalies, Blattella germanica, Blattella asahinai, Leucophaea maderae, Panchlora spp., Parcoblatta spp., Periplaneta austalasiae, Periplaneta americana, Periplaneta brunnea, Periplaneta fuliginosa, Supella longipalpa.

From the order of the Saltatoria, for example, Acheta domesticus.

From the order of the Dermaptera, for example, Forficula auricularia.

From the order of the Isoptera, for example, Kalotermes spp., Reticulitermes spp.

From the order of the Psocoptera, for example, Lepinatus spp., Liposcelis spp.

From the order of the Coleoptera, for example, Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

From the order of the Diptera, for example, Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

From the order of the Lepidoptera, for example, Achroia grisella, Galleria mellonella, Plodia interpunctella, Tinea cloacella, Tinea pellionella, Tineola bisselliella.

From the order of the Siphonaptera, for example, Ctenocephalides canis, Ctenocephalides felis, Pulex irritans, Tunga penetrans, Xenopsylla cheopis.

From the order of the Hymenoptera, for example, Camponotus herculeanus, Lasius fuliginosus, Lasius niger, Lasius umbratus, Monomorium pharaonis, Paravespula spp., Tetramorium caespitum.

From the order of the Anoplura, for example, Pediculus humanus capitis, Pediculus humanus corporis, Pemphigus spp., Phylloera vastatrix, Phthirus pubis.

From the order of the Heteroptera, for example, Cimex hemipterus, Cimex lectularius, Rhodinus prolixus, Triatoma infestans.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver,

*Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The active compounds according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), pyroxasulfone, quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

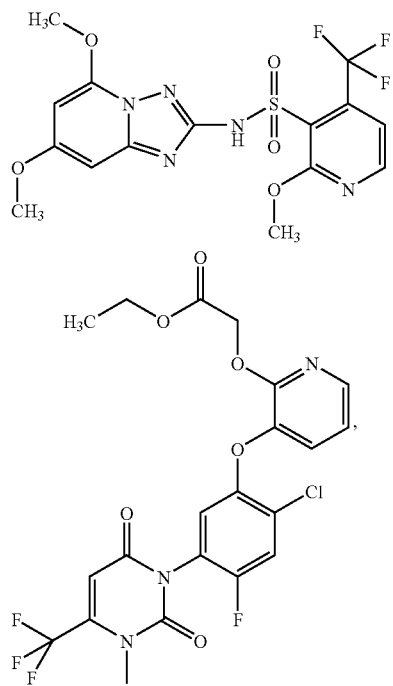

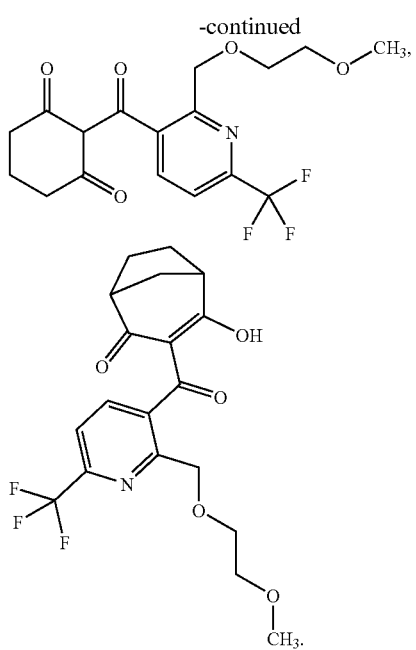

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soybeans, potatoes, cotton, oilseed rape, beet, sugar cane and also fruit plants (with the fruits apples, pears, citrus fruits and grapevines), greater emphasis being given to maize, soybeans, potatoes, cotton and oilseed rape.

The compounds/active compound combinations according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:
Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or
Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae;
Pseudocercosporella species, such as, for example, Pseudocercosporella herpotrichoides.

The active compounds/active compound combinations according to the invention also have very good fortifying action in plants. Accordingly, they are suitable for mobilizing the defences of the plant against attack by unwanted microorganisms.

In the present context, plant-fortifying (resistance-inducing) substances are to be understood as meaning those substances which are capable of stimulating the defence system of plants such that, when the treated plants are subsequently inoculated with unwanted microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds/active compound combinations are well tolerated by plants at the concentrations required for controlling plant diseases permits the treatment of above-ground parts of plants, of propagation stock and seeds, and of the soil.

The active compounds/active compound combinations according to the invention are also suitable for increasing the yield of crops. In addition, they show reduced toxicity and are well tolerated by plants.

At certain concentrations and application rates, the active compounds/active compound combinations according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds/active compound combinations can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds/active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide.

Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds/active compound combinations according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing partners are, for example, the substances mentioned above (fungicides, bactericides, insecticides/acaricides/nematicides).

A mixture with other known active compounds, such as herbicides, or with fertilizers and growth regulators is also possible.

In addition, the compounds of the formula (I)/active compound combinations according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of fungi does by no means limit the mycotic spectrum which can be covered, but is only for illustration.

The active compounds/active compound combinations can be used as such, in the form of their formulations or the use forms prepared therefrom, such as ready-to-use solutions, suspensions, wettable powders, pastes, soluble powders, dusts and granules. Application is carried out in a customary manner, for example by pouring, spraying, atomizing, broadcasting, dusting, forming, spreading, etc. It is furthermore possible to apply the active compounds by the ultra-low volume method, or to inject the active compound preparation or the active compound itself into the soil. It is also possible to treat the seeds of plants.

When using the active compounds/active compound combinations according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The term "active compounds" always also includes the active compound combinations mentioned here. Preparation and use of the active compounds according to the invention is illustrated by the examples below.

EXAMPLES

Example I-1-a-1

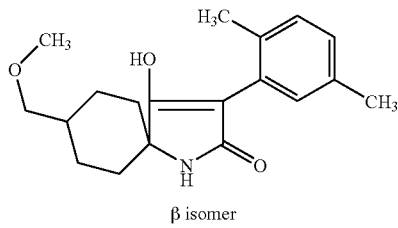

β isomer

Under argon, 2.2 eq=2.5 g of potassium tert-butoxide, 95% pure (25.6 mmol) are initially charged in 10 ml of dimethylacetamide. At 80 to 100° C., 4.2 g of the compound of Example II-1 (12.1 mmol) in 5 ml of dimethylacetamide are added dropwise. The mixture is stirred at 100° C. for 1 hour. After the reaction has ended (monitored by thin-layer chromatography), the reaction mixture is poured into 200 ml of ice-water, the pH is adjusted to 2 using conc. HCl and the precipitate is filtered off with suction and recrystallized from methyl tert-butyl ether/hexane.

Yield: 3.8 g (96% of theory), m.p. 177° C.

Analogously to Example (I-1-a-1) and in accordance with the general statements on the preparation, the following compounds of the formula (I-1-a) where

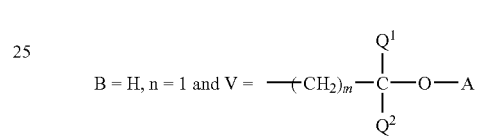

are obtained (I-1-a)

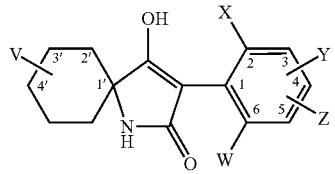

| Ex. No. | W | X | Y | Z | V | m | $Q^1$ | $Q^2$ | A | m.p. °C. | Isomer |
|---|---|---|---|---|---|---|---|---|---|---|---|
| I-1-a-2 | $CH_3$ | $CH_3$ | 4-$CH_3$ | H | 4' | 0 | H | H | $CH_3$ | 249 | β |
| I-1-a-3 | $C_2H_5$ | Br | 4-$CH_3$ | H | 4' | 0 | H | H | $CH_3$ | 212 | β |
| I-1-a-4 | $C_2H_5$ | O—$CH_3$ | 4-Cl | H | 4' | 0 | H | H | $CH_3$ | 193 | β |
| I-1-a-5 | H | $CH_3$ | 5-(4-Cl—Ph) | H | 4' | 0 | H | H | $CH_3$ | 256 | β |
| I-1-a-6 | H | $CH_3$ | H | 5-$CH_3$ | 3' | 0 | H | H | $CH_3$ | 143 | β |
| I-1-a-7 | $CH_3$ | $CH_3$ | 4-$CH_3$ | H | 3' | 0 | H | H | $CH_3$ | 96 | β |
| I-1-a-8 | $C_2H_5$ | Br | 4-$CH_3$ | H | 3' | 0 | H | H | $CH_3$ | 161 | β |
| I-1-a-9 | $C_2H_5$ | O—$CH_3$ | 4-Cl | H | 3' | 0 | H | H | $CH_3$ | 200 | β |
| I-1-a-10 | H | $CH_3$ | H | 5-$CH_3$ | 3' | 0 | H | H | $C_3H_7$ | 96 | β |
| I-1-a-11 | $CH_3$ | $CH_3$ | 4-$CH_3$ | H | 3' | 0 | H | H | $C_3H_7$ | 215 | β |
| I-1-a-12 | $C_2H_5$ | Br | 4-$CH_3$ | H | 3' | 0 | H | H | $C_3H_7$ | 182 | β |
| I-1-a-13 | $C_2H_5$ | $CH_3$ | 4-Br | H | 3' | 0 | H | H | $C_3H_7$ | 110 | β |
| I-1-a-14 | $CH_3$ | $CH_3$ | 5-(4-Cl—Ph) | H | 3' | 0 | H | H | $CH_3$ | 251 | β |
| I-1-a-15 | $CH_3$ | Cl | 4-Cl | H | 3' | 0 | H | H | $CH_3$ | 223 | β |
| I-1-a-16 | H | $CH_3$ | 4-$CH_3$ | 5-$CH_3$ | 3' | 0 | H | H | $CH_3$ | 212 | β |
| I-1-a-17 | $CH_3$ | $CH_3$ | 4-$CH_3$ | 5-$CH_3$ | 3' | 0 | H | H | $CH_3$ | 252 | β |
| I-1-a-18 | $CH_3$ | $CH_3$ | 4-Br | H | 3' | 0 | H | H | $CH_3$ | 192 | β |
| I-1-a-19 | Cl | Cl | 4-Cl | H | 3' | 0 | H | H | $CH_3$ | 208 | β |
| I-1-a-20 | H | $CH_3$ | 5-(4-Cl—Ph) | H | 3' | 0 | H | H | $CH_3$ | 196 | β |
| I-1-a-21 | H | $CH_3$ | 4-Cl | 5-$CH_3$ | 3' | 0 | H | H | $CH_3$ | 203 | β |
| I-1-a-22 | H | Br | H | 5-$CH_3$ | 3' | 0 | H | H | $CH_3$ | 106 | β |
| I-1-a-23 | $CH_3$ | $CH_3$ | 4-I | H | 3' | 0 | H | H | $CH_3$ | 107 | β |
| I-1-a-24 | H | Cl | 5-(4-Cl—Ph) | H | 3' | 0 | H | H | $CH_3$ | 229 | β |
| I-1-a-25 | $CH_3$ | $CH_3$ | 4-Cl | H | 3' | 0 | H | H | $CH_3$ | 196 | β |
| I-1-a-26 | $CH_3$ | $C_2H_5$ | 4-Br | H | 3' | 0 | H | H | $CH_3$ | 119 | β |

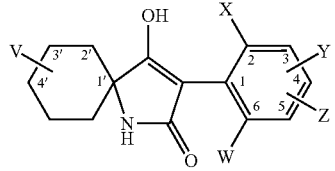

(I-1-a)

| Ex. No. | W | X | Y | Z | V | m | Q¹ | Q² | A | m.p. ° C. | Isomer |
|---|---|---|---|---|---|---|---|---|---|---|---|
| I-1-a-27 | $CH_3$ | $C_2H_5$ | 4-$CH_3$ | H | 3' | 0 | H | H | $CH_3$ | *3.30 (m, 3 H, $CH_2$—O$CH_3$) 6.9 (s, 2 H, Ar—H) | β |
| I-1-a-28 | $CH_3$ | $CH_3$ | 5-(4-Cl—Ph) | H | 4' | 0 | H | H | $CH_3$ | decomp. | β |
| I-1-a-29 | H | $CH_3$ | 4-$CH_3$ | 5-$CH_3$ | 4' | 0 | H | H | $CH_3$ | 61 | β |
| I-1-a-30 | $CH_3$ | $CH_3$ | 4-$CH_3$ | 5-$CH_3$ | 4' | 0 | H | H | $CH_3$ | wax | β |
| I-1-a-31 | $CH_3$ | $CH_3$ | 4-Br | H | 4' | 0 | H | H | $CH_3$ | 242 | β |
| I-1-a-32 | $CH_3$ | $CH_3$ | 4-Cl | H | 4' | 0 | H | H | $CH_3$ | 212 | β |
| I-1-a-33 | H | Br | H | 5-$CH_3$ | 4' | 0 | H | H | $CH_3$ | 230 | β |
| I-1-a-34 | H | Cl | 5-(4-Cl—Ph) | H | 4' | 0 | H | H | $CH_3$ | 242 | β |
| I-1-a-35 | $CH_3$ | Cl | 4-Cl | H | 4' | 0 | H | H | $CH_3$ | 255 | β |
| I-1-a-36 | $CH_3$ | $OCH_3$ | 4-$CH_3$ | H | 4' | 0 | H | H | $CH_3$ | 187 | β |
| I-1-a-37 | H | $CH_3$ | 4-Cl | 5-$CH_3$ | 4' | 0 | H | H | $CH_3$ | 102 | β |
| I-1-a-38 | Cl | Cl | 4-Cl | H | 4' | 0 | H | H | $CH_3$ | 265 | β |
| I-1-a-39 | $CH_3$ | $CH_3$ | 4-$CH_3$ | H | 3' | 1 | H | H | $CH_3$ | 74 | β |
| I-1-a-40 | $CH_3$ | $CH_3$ | 4-Cl | H | 3' | 1 | H | H | $CH_3$ | 198 | β |
| I-1-a-41 | $CH_3$ | $CH_3$ | 4-Br | H | 3' | 1 | H | H | $CH_3$ | 74 | β |
| I-1-a-42 | $CH_3$ | $CH_3$ | 5-(4-Cl—Ph) | H | 3' | 1 | H | H | $CH_3$ | 81 | β |
| I-1-a-43 | H | $CH_3$ | H | 5-$CH_3$ | 3' | 1 | H | H | $CH_3$ | 83 | β |
| I-1-a-44 | $C_2H_5$ | Br | 4-$CH_3$ | H | 3' | 1 | H | H | $CH_3$ | 100 | β |
| I-1-a-45 | $C_2H_5$ | $OCH_3$ | 4-Cl | H | 3' | 1 | H | H | $CH_3$ | 100 | β |
| I-1-a-46 | $OCH_3$ | Cl | 4-$CH_3$ | H | 3' | 1 | H | H | $CH_3$ | 163-164 | β |
| I-1-a-47 | $C_2H_5$ | $OC_2H_5$ | 4-Cl | H | 3' | 1 | H | H | $CH_3$ | **2.63 (m, 2 H, Ar—$CH_2$), 3.41 (m, 2 H, $CH_2$O) | β |
| I-1-a-48 | $C_2H_5$ | Br | 4-$CH_3$ | H | 4' | 1 | H | H | $CH_3$ | 180-183 | β |
| I-1-a-49 | $C_2H_5$ | $OC_2H_5$ | 4-Cl | H | 4' | 1 | H | H | $CH_3$ | 152-154 | β |
| I-1-a-50 | $C_2H_5$ | $OCH_3$ | 4-Cl | H | 4' | 1 | H | H | $CH_3$ | 185-188 | β |
| I-1-a-51 | $OCH_3$ | Cl | 4-$CH_3$ | H | 4' | 1 | H | H | $CH_3$ | 175-188 | β |
| I-1-a-52 | H | $CH_3$ | 5-(4-Cl—Ph) | H | 4' | 1 | H | H | $CH_3$ | 93 | β |
| I-1-a-53 | $CH_3$ | $CH_3$ | 5-(4-Cl—Ph) | H | 4' | 1 | H | H | $CH_3$ | 258 | β |
| I-1-a-54 | $CH_3$ | $CH_3$ | 4-Cl | H | 4' | 1 | H | H | $CH_3$ | 153 | β |
| I-1-a-55 | $CH_3$ | $CH_3$ | 4-$CH_3$ | H | 4' | 1 | H | H | $CH_3$ | 201 | β |
| I-1-a-56 | $CH_3$ | $CH_3$ | 4-Br | H | 4' | 1 | H | H | $CH_3$ | 163 | β |
| I-1-a-57 | $CH_3$ | $CH_3$ | 4-I | H | 4' | 1 | H | H | $CH_3$ | 148 | β |
| I-1-a-58 | H | $CH_3$ | H | 5-$CH_3$ | 4' | 1 | H | H | $CH_3$ | 161 | β |
| I-1-a-59 | H | $CH_3$ | 4-Cl | 5-$CH_3$ | 4' | 1 | H | H | $CH_3$ | 280 | β |
| I-1-a-60 | $CH_3$ | $OCH_3$ | 4-$CH_3$ | H | 3' | 0 | H | H | $CH_3$ | 217 | β |

*¹H-NMR (400 MHz, $CDCl_3$): shift δ in ppm.
**¹H-NMR (400 MHz, $d_6$-DMSO): shift δ in ppm.

Example I-1-b-1

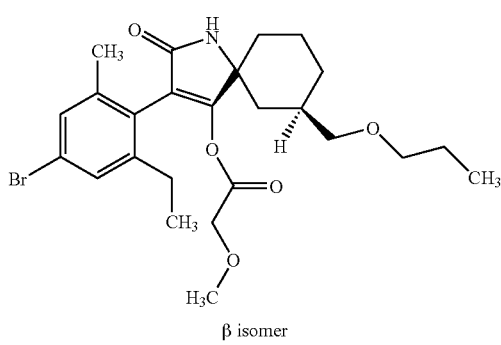

β isomer 0.218 g, 0.5 mmol, of the compound of Example I-1-a-13 is dissolved in 8 ml of ethyl acetate, and 1.5 eq of triethylamine (0.75 mmol, 0.1 ml) are added. 1.1 eq of methoxyacetyl chloride are dissolved in 2 ml of ethyl acetate and, at reflux, added dropwise in 5 portions over a period of 30 min. After 6 h at reflux, the mixture is stirred at room temperature overnight, saturated NaCl solution is added and the organic phase is dried, concentrated and purified by column chromatography using a gradient of n-heptane/ethyl acetate (90:10 to 0:100).

Yield: 175 mg (65% of theory), m.p. 138° C.

Analogously to Example (I-1-b-1) and in accordance with the general statements on the preparation, the following compounds of the formula (I-1-b) where

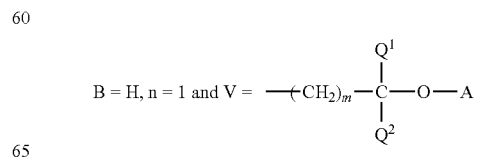

are obtained (I-1-b)

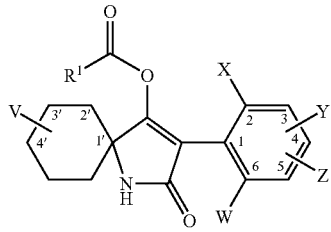

| Ex. No. | W | X | Y | Z | V | m | Q¹ | Q² | A | R¹ | m.p. °C. | Isomer |
|---|---|---|---|---|---|---|---|---|---|---|---|---|
| I-1-b-2 | C$_2$H$_5$ | Br | 4-CH$_3$ | H | 4' | 0 | H | H | CH$_3$ | H$_3$C—O—CH$_2$— | *3.23 (d, 2 H, CH$_2$O—) 4.08 (d, 2 H, CH$_2$O—) | β |
| I-1-b-3 | C$_2$H$_5$ | OCH$_3$ | 4-Cl | H | 4' | 0 | H | H | CH$_3$ | H$_3$C—O—CH$_2$— | *3.21 (d, 2 H, CH$_2$O—) 4.01 (d, 2 H, CH$_2$O—) | β |
| I-1-b-4 | C$_2$H$_5$ | OCH$_3$ | 4-Cl | H | 4' | 0 | H | H | CH$_3$ | i-C$_3$H$_7$ | oil | β |
| I-1-b-5 | C$_2$H$_5$ | Br | 4-CH$_3$ | H | 4' | 0 | H | H | CH$_3$ | i-C$_3$H$_7$ | 217-220 | β |
| I-1-b-6 | C$_2$H$_5$ | OCH$_3$ | 4-Cl | H | 3' | 0 | H | H | CH$_3$ | H$_3$C—O—CH$_2$— | **3.29 (d, 2 H, CH$_2$—O—CH$_2$-cyc) 4.00 (s, 2 H, CO—CH$_2$—CH$_3$) 6.84 (s, 2 H, Ar—H) | β |
| I-1-b-7 | CH$_3$ | CH$_3$ | 4-CH$_3$ | H | 3' | 0 | H | H | C$_3$H$_7$ | H$_3$C—O—CH$_2$— | **3.30 (m, 3 H, CH$_2$—O—CH$_3$) 4.02 (d, 2 H, CO—CH$_2$—OCH$_3$) 6.71 and 6.87 (each m, 1 H, Ar—H) | β |
| I-1-b-8 | C$_2$H$_5$ | OCH$_3$ | 4-Cl | H | 3' | 0 | H | H | CH$_3$ | i-C$_3$H$_7$ | **2.55 (m, 3 H, Ar—CH$_2$ and (CH$_3$)$_2$CH) 3.32 (d, 3 H, CH$_2$—OCH$_3$) 6.70 and 6.86 (each m, 1 H, Ar—H) | β |
| I-1-b-9 | CH$_3$ | OCH$_3$ | 4-CH$_3$ | H | 3' | 0 | H | H | CH$_3$ | i-C$_3$H$_7$ | **2.56 (m, 1 H, (CH$_3$)$_2$CH) 3.32 (d, 3 H, CH$_2$—OCH$_3$) 6.49 and 6.63 (each s, 1 H, Ar—H) | β |
| I-1-b-10 | C$_2$H$_5$ | OC$_2$H$_5$ | 4-Cl | H | 3' | 0 | H | H | CH$_3$ | i-C$_3$H$_7$ | **2.60 (m, 3 H, (CH$_3$)$_2$CH and Ar—CH$_2$) 3.30 (m, 3 H, CH$_2$—OCH$_3$) 6.65 and 6.85 (each m, 1 H, Ar—H) | β |
| I-1-b-11 | CH$_3$ | Cl | 4-Cl | H | 3' | 0 | H | H | CH$_3$ | i-C$_3$H$_7$ | 185 | β |
| I-1-b-12 | CH$_3$ | CH$_3$ | 4-Br | H | 4' | 0 | H | H | CH$_3$ | i-C$_3$H$_7$ | 215 | β |
| I-1-b-13 | CH$_3$ | CH$_3$ | 4-Cl | H | 4' | 0 | H | H | CH$_3$ | i-C$_3$H$_7$ | 197 | β |
| I-1-b-14 | CH$_3$ | CH$_3$ | 4-CH$_3$ | H | 4' | 0 | H | H | CH$_3$ | i-C$_3$H$_7$ | 195 | β |
| I-1-b-15 | H | CH$_3$ | 4-CH$_3$ | 5-CH$_3$ | 4' | 0 | H | H | CH$_3$ | i-C$_3$H$_7$ | 186 | β |
| I-1-b-16 | H | CH$_3$ | H | 5-CH$_3$ | 4' | 0 | H | H | CH$_3$ | i-C$_3$H$_7$ | **1.01 (d, 6 H, CH(CH$_3$)$_2$) 2.16, 2.25 (2s, 6 H, Ar—CH$_3$) 3.23 (d, 2 H, O—CH$_2$) 3.29 (s, 3 H, OCH$_3$) | β |
| I-1-b-17 | C$_2$H$_5$ | Br | 4-CH$_3$ | H | 3' | 1 | H | H | CH$_3$ | i-C$_3$H$_7$ | **2.60 (m, 3 H, Ar—CH$_2$ and (CH$_3$)$_2$CH) 3.33 (s, 3 H, CH$_2$—OCH$_3$) 7.01 and 7.25 (each, 1 H, Ar—H) | β |
| I-1-b-18 | C$_2$H$_5$ | OC$_2$H$_5$ | 4-Cl | H | 3' | 1 | H | H | CH$_3$ | i-C$_3$H$_7$ | **2.58 (m, 3 H, Ar—CH$_2$ and (CH$_3$)$_2$CH) 3.32 (s, 3 H, CH$_2$—OCH$_3$) 6.66 and 6.86 (each s, 1 H, Ar—H) | β |
| I-1-b-19 | C$_2$H$_5$ | Br | 4-CH$_3$ | H | 4' | 1 | H | H | CH$_3$ | i-C$_3$H$_7$ | **2.59 (m, 3 H, Ar—CH$_2$ and (CH$_3$)$_2$CH) 3.33 (s, 3 H, CH$_2$—OCH$_3$) 7.01 and 7.23 (each s, 1 H, Ar—H) | β |
| I-1-b-20 | C$_2$H$_5$ | OCH$_3$ | 4-Cl | H | 4' | 1 | H | H | CH$_3$ | i-C$_3$H$_7$ | **2.54 (m, 3 H, Ar—CH$_2$ and (CH$_3$)$_2$CH) 3.33 (s, 3 H, CH$_2$—OCH$_3$) 6.71 and 6.86 (each s, 1 H, Ar—H) | β |
| I-1-b-21 | OCH$_3$ | Cl | 4-CH$_3$ | H | 4' | 1 | H | H | CH$_3$ | i-C$_3$H$_7$ | **2.62 (h, 2 H, (CH$_3$)$_2$CH) 3.33 (d, 3 H, CH$_2$—OCH$_3$) 6.61 and 6.82 (each s, 1 H, Ar-H) | β |
| I-1-b-22 | C$_2$H$_5$ | OC$_2$H$_5$ | 4-Cl | H | 4' | 1 | H | H | CH$_3$ | i-C$_3$H$_7$ | **2.58 (m, 3 H, Ar—CH$_2$ and (CH$_3$)$_2$CH) 3.34 (s, 3 H, CH$_2$—OCH$_3$) 6.64 and 6.86 (each s, 1 H, Ar—H) | β |
| I-1-b-23 | H | Br | H | 5-CH$_3$ | 4' | 0 | H | H | CH$_3$ | △ | wax **0.83-0.94 (m, 4 H, cyclopropyl-H) 2.28 (s, 3 H, Ar—CH$_3$) | β |

*$^1$H-NMR (300 MHz, CDCN): shift δ in ppm.
**$^1$H-NMR (400 MHz, CDCl$_3$): shift δ in ppm.

Example I-1-c-1

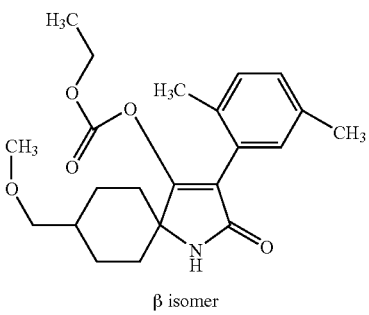

β isomer

Under argon, 0.9 g of the compound of Example I-1-a-1 (0.00285 mol) is initially charged in 20 ml of anhydrous methylene chloride and 0.3 g of triethylamine (0.42 ml), and 20 mg of Steglich base are added; at 20° C., 0.27 ml of ethyl chloroformate (0.00285 mol) in 3 ml of anhydrous methylene chloride are added dropwise. The mixture is stirred at 20° C. for 4 hours. The reaction is monitored by thin-layer chromatography.

The reaction mixture is purified by column chromatography (silica gel, dichloromethane:ethyl acetate=10:1).
Yield: 0.45 g (36% of theory), m.p. 128° C.

Analogously to Example (I-1-c-1) and in accordance with the general statements on the preparation, the following compounds of the formula (I-1-c) where

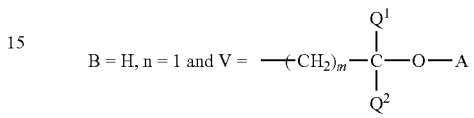

$B = H$, $n = 1$ and $V = -(CH_2)_m-C(Q^1)(Q^2)-O-A$ are obtained (I-1-c)

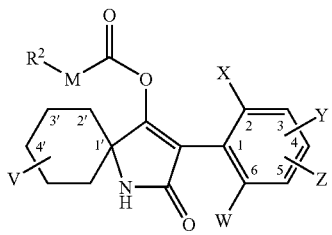

| Ex. No. | W | X | Y | Z | V | m | $Q^1$ | $Q^2$ | A | M | $R^2$ | m.p. ° C. | Isomer |
|---|---|---|---|---|---|---|---|---|---|---|---|---|---|
| I-1-c-2 | H | $CH_3$ | H | 5-$CH_3$ | 3' | 0 | H | H | $CH_3$ | O | $C_2H_5$ | *3.28 (s, 3 H, O$CH_3$) 4.02 (q, 2 H, O$CH_2$$CH_3$) | β |
| I-1-c-3 | $C_2H_5$ | $OCH_3$ | 4-Cl | H | 3' | 0 | H | H | $CH_3$ | O | $C_2H_5$ | 163 | β |
| I-1-c-4 | $CH_3$ | $CH_3$ | 4-$CH_3$ | H | 3' | 0 | H | H | $C_3H_7$ | O | $C_2H_5$ | 195-197 | β |
| I-1-c-5 | $C_2H_5$ | $CH_3$ | 4-$CH_3$ | H | 3' | 0 | H | H | $C_3H_7$ | O | $C_2H_5$ | 173 | β |
| I-1-c-6 | $C_2H_5$ | Br | 4-$CH_3$ | H | 4' | 0 | H | H | $CH_3$ | O | $C_2H_5$ | 170-173 | β |
| I-1-c-7 | $C_2H_5$ | $OCH_3$ | 4-Cl | H | 4' | 0 | H | H | $CH_3$ | O | $C_2H_5$ | *3.20 (d, 2 H, $CH_2$O) 4.03 (q, 2 H, O—$CH_2$$CH_3$) | β |
| I-1-c-8 | H | $CH_3$ | 5-(4-Cl—Ph) | H | 4' | 0 | H | H | $CH_3$ | O | $C_2H_5$ | 156 | β |
| I-1-c-9 | $CH_3$ | $CH_3$ | 4-$CH_3$ | H | 3' | 0 | H | H | $CH_3$ | O | $C_2H_5$ | 183 | β |
| I-1-c-10 | $CH_3$ | Cl | 4-Cl | H | 3' | 0 | H | H | $CH_3$ | O | $C_2H_5$ | 168 | β |
| I-1-c-11 | $C_2H_5$ | $CH_3$ | 4-Br | H | 3' | 0 | H | H | $CH_3$ | O | $C_2H_5$ | 87 | β |
| I-1-c-12 | $C_2H_5$ | Cl | 4-Cl | H | 3' | 0 | H | H | $CH_3$ | O | $C_2H_5$ | **4.05 (q, 2 H, COO$CH_2$) 3.30 (d, 3 H, $CH_2$—O$CH_3$) 7.15 and 7.25 (each m, 1 H, Ar—$H$) | β |
| I-1-c-13 | $C_2H_5$ | $CH_3$ | 4-$CH_3$ | H | 3' | 0 | H | H | $CH_3$ | O | $C_2H_5$ | 159 | β |
| I-1-c-14 | $CH_3$ | $OCH_3$ | 4-$CH_3$ | H | 3' | 0 | H | H | $CH_3$ | O | $C_2H_5$ | **3.32 (s, 3 H, $CH_2$—O$CH_3$) 3.99 (m, 2 H, COO$CH_2$) 6.52 and 6.64 (each s, 1 H, Ar—$H$) | β |
| I-1-c-15 | $CH_3$ | $C_2H_5$ | 4-Br | H | 4' | 0 | H | H | $CH_3$ | O | $C_2H_5$ | 150 | β |
| I-1-c-16 | $CH_3$ | $CH_3$ | 4-$CH_3$ | H | 4' | 0 | H | H | $CH_3$ | O | $C_2H_5$ | 170 | β |
| I-1-c-17 | $CH_3$ | $CH_3$ | 4-Br | H | 4' | 0 | H | H | $CH_3$ | O | $C_2H_5$ | 203 | β |
| I-1-c-18 | $CH_3$ | $OCH_3$ | 4-$CH_3$ | H | 4' | 0 | H | H | $CH_3$ | O | $C_2H_5$ | 146 | β |
| I-1-c-19 | $CH_3$ | $CH_3$ | 4-Cl | H | 4' | 0 | H | H | $CH_3$ | O | $C_2H_5$ | 195 | β |
| I-1-c-20 | $CH_3$ | Cl | 4-Cl | H | 4' | 0 | H | H | $CH_3$ | O | $C_2H_5$ | 178 | β |
| I-1-c-21 | H | Br | H | 5-$CH_3$ | 4' | 0 | H | H | $CH_3$ | O | $C_2H_5$ | 163 | β |
| I-1-c-22 | H | $CH_3$ | 4-Cl | 5-$CH_3$ | 4' | 0 | H | H | $CH_3$ | O | $C_2H_5$ | 163 | β |
| I-1-c-23 | H | $CH_3$ | 4-$CH_3$ | 5-$CH_3$ | 4' | 0 | H | H | $CH_3$ | O | $C_2H_5$ | 159 | β |
| I-1-c-24 | $C_2H_5$ | Br | 4-$CH_3$ | H | 3' | 1 | H | H | $CH_3$ | O | $C_2H_5$ | **3.32 (s, 3 H, O$CH_3$) 4.05 (q, 2 H, COO$CH_2$) 7.03 and 7.27 (each s, 1 H, Ar—$H$) | β |
| I-1-c-25 | $C_2H_5$ | $OC_2H_5$ | 4-Cl | H | 3' | 1 | H | H | $CH_3$ | O | $C_2H_5$ | **3.32 (s, 3 H, $CH_2$—O$CH_3$) 4.01 (m, 2 H, COO$CH_2$) 6.68 and 6.88 (each s, 1 H, Ar—$H$) | β |
| I-1-c-26 | $C_2H_5$ | $OCH_3$ | 4-Cl | H | 3' | 1 | H | H | $CH_3$ | O | $C_2H_5$ | **3.32 (s, 3 H, O$CH_3$) 4.03 (q, 2 H, COO$CH_2$) 6.72 u. 6.87 (each s, 1 H, Ar—$H$) | β |

-continued

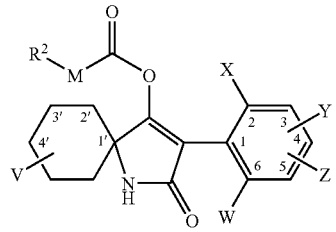

(I-1-c)

| Ex. No. | W | X | Y | Z | V | m | Q¹ | Q² | A | M | R² | m.p. °C. | Isomer |
|---|---|---|---|---|---|---|---|---|---|---|---|---|---|
| I-1-c-27 | OCH₃ | Cl | 4-CH₃ | H | 3' | 1 | H | H | CH₃ | O | C₂H₅ | **3.32 (s, 3 H, CH₂—O<u>CH₃</u>) 4.04 (q, 2 H, COOC<u>H₂</u>) 6.63 and 6.86 (each s, 1 H, Ar—<u>H</u>) | β |
| I-1-c-28 | C₂H₅ | Br | 4-CH₃ | H | 4' | 1 | H | H | CH₃ | O | C₂H₅ | 163-165 | β |
| I-1-c-29 | C₂H₅ | OC₂H₅ | 4-Cl | H | 4' | 1 | H | H | CH₃ | O | C₂H₅ | 207-210 | β |
| I-1-c-30 | C₂H₅ | O-CH₃ | 4-Cl | H | 4' | 1 | H | H | CH₃ | O | C₂H₅ | 165-166 | β |
| I-1-c-31 | OCH₃ | Cl | 4-CH₃ | H | 4' | 1 | H | H | CH₃ | O | C₂H₅ | 177-180 | β |
| I-1-c-32 | CH₃ | CH₃ | 4-Br | H | 4' | 1 | H | H | CH₃ | O | C₂H₅ | 165 | β |
| I-1-c-33 | CH₃ | CH₃ | 4-Cl | H | 4' | 1 | H | H | CH₃ | O | C₂H₅ | 144 | β |
| I-1-c-34 | CH₃ | CH₃ | 4-CH₃ | H | 4' | 1 | H | H | CH₃ | O | C₂H₅ | wax **3.38 (t, 2 H, O—C<u>H₂</u>—CH₂—) 6.83 (s, 2 H, Ar-H) 3.97 (q, 2 H, O—C<u>H₂</u>CH₃) | β |
| I-1-c-35 | CH₃ | C₂H₅ | 4-CH₃ | H | 4' | 0 | H | H | CH₃ | O | C₂H₅ | 150 | β |
| I-1-c-36 | H | Br | H | 5-CH₃ | 4' | 0 | H | H | CH₃ | O | C₆H₅—CH₂ | wax **2.24 (s, 3 H, Ar—C<u>H₃</u>) 3.23 (d, 2 H, C<u>H₂</u>—O—CH₃) 5.05 (s, 2 H, O—C<u>H₂</u>C₆H₅) | β |
| I-1-c-37 | C₂H₅ | OC₂H₅ | 4-Cl | H | 4' | 0 | H | H | CH₃ | O | C₂H₅ | 195 | β |
| I-1-c-38 | C₂H₅ | Cl | 4-Cl | H | 4' | 0 | H | H | CH₃ | O | C₂H₅ | wax | β |
| I-1-c-39 | CH₃ | C₂H₅ | 4-CH₃ | H | 4' | 0 | H | H | CH₃ | O | C₂H₅ | 143 | β |

*¹H-NMR (400 MHz, CD₃CN): shift δ in ppm
**¹H-NMR (400 MHz, CDCl₃): shift δ in ppm Example II-1

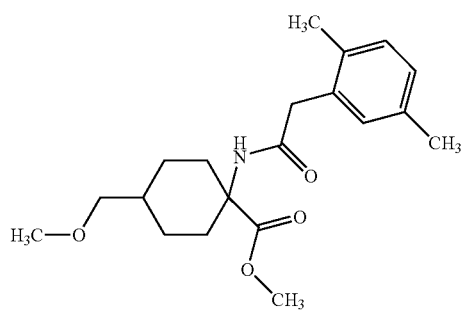

Under argon, 3.57 g of the compound of Example XIV-1 are initially charged in 50 ml of anhydrous tetrahydrofuran and 3 g of triethylamine (30 mmol)=4.2 ml, and 2.75 g (0.015 mol) of 2,5-dimethylphenylacetyl chloride in 5 ml of anhydrous tetrahydrofuran are added at 0 to 10° C.

The reaction is monitored by thin-layer chromatography. The solvent is removed using a rotary evaporator and the residue is purified by column chromatography (silica gel, hexane:ethyl acetate=8:2).

Yield: 4.3 g (81% of theory), m.p. 11 g° C.

Analogously to Example (II-1) and in accordance with the general statements of the preparation, the following compounds of the formula (II) where

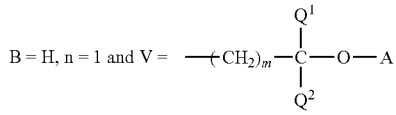

B = H, n = 1 and V = are obtained

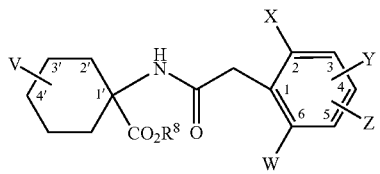

(II)

| Ex. No. | W | X | Y | Z | V | m | Q¹ | Q² | A | R⁸ | m.p. °C. | Isomer |
|---|---|---|---|---|---|---|---|---|---|---|---|---|
| II-2 | H | CH₃ | H | 5-CH₃ | 3' | 0 | H | H | CH₃ | CH₃ | 144 | β |
| II-3 | CH₃ | CH₃ | 4-CH₃ | H | 3' | 0 | H | H | CH₃ | CH₃ | 103 | β |

-continued

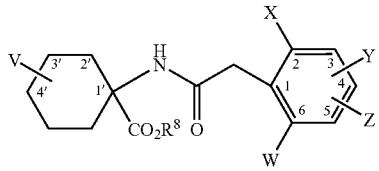

(II)

| Ex. No. | W | X | Y | Z | V | m | Q¹ | Q² | A | R⁸ | m.p. °C. | Isomer |
|---|---|---|---|---|---|---|---|---|---|---|---|---|
| II-4 | C₂H₅ | OCH₃ | 4-Cl | H | 3' | 0 | H | H | CH₃ | CH₃ | 84 | β |
| II-5 | C₂H₅ | Br | 4-CH₃ | H | 3' | 0 | H | H | CH₃ | CH₃ | 113 | β |
| II-6 | H | CH₃ | H | 5-CH₃ | 3' | 0 | H | H | C₃H₇ | CH₃ | 119 | β |
| II-7 | CH₃ | CH₃ | 4-CH₃ | H | 3' | 0 | H | H | C₃H₇ | CH₃ | 88 | β |
| II-8 | C₂H₅ | Br | 4-CH₃ | H | 3' | 0 | H | H | C₃H₇ | CH₃ | 85 | β |
| II-9 | C₂H₅ | CH₃ | Br | H | 3' | 0 | H | H | C₃H₇ | CH₃ | 95 | β |
| II-10 | CH₃ | CH₃ | 4-CH₃ | H | 4' | 0 | H | H | CH₃ | CH₃ | 138 | β |
| II-11 | C₂H₅ | OCH₃ | 4-Cl | H | 4' | 0 | H | H | CH₃ | CH₃ | 136 | β |
| II-12 | C₂H₅ | Br | 4-CH₃ | H | 4' | 0 | H | H | CH₃ | CH₃ | 124 | β |
| II-13 | H | CH₃ | 5-(4-Cl—Ph) | H | 4' | 0 | H | H | CH₃ | CH₃ | 110 | β |
| II-14 | CH₃ | CH₃ | 5-(4-Cl—Ph) | H | 3' | 0 | H | H | CH₃ | CH₃ | *2.20, 2.39 (2 s, 6 H, Ar-CH₃) 3.28, (s, 3 H, OCH₃) 3.63, (s, 3 H, CO₂CH₃) 3.72, (s, 2 H, CH₂CO) | β |
| II-15 | CH₃ | Cl | 4-Cl | H | 3' | 0 | H | H | CH₃ | CH₃ | 129 | β |
| II-16 | H | CH₃ | 4-CH₃ | 5-CH₃ | 3' | 0 | H | H | CH₃ | CH₃ | 121 | β |
| II-17 | CH₃ | CH₃ | 4-CH₃ | 5-CH₃ | 3' | 0 | H | H | CH₃ | CH₃ | 113 | β |
| II-18 | CH₃ | CH₃ | 4-Br | H | 3' | 0 | H | H | CH₃ | CH₃ | 125 | β |
| II-19 | Cl | Cl | 4-Cl | H | 3' | 0 | H | H | CH₃ | CH₃ | 127 | β |
| II-20 | H | CH₃ | 5-(4-Cl—Ph) | H | 3' | 0 | H | H | CH₃ | CH₃ | 157 | β |
| II-21 | H | CH₃ | 4-Cl | 5-CH₃ | 3' | 0 | H | H | CH₃ | CH₃ | 141 | β |
| II-22 | CH₃ | CH₃ | 4-I | H | 3' | 0 | H | H | CH₃ | CH₃ | 156 | β |
| II-23 | H | Br | H | 5-CH₃ | 3' | 0 | H | H | CH₃ | CH₃ | 137 | β |
| II-24 | H | Cl | 5-(4-Cl—Ph) | H | 3' | 0 | H | H | CH₃ | CH₃ | 156 | β |
| II-25 | CH₃ | OCH₃ | 4-CH₃ | H | 3' | 0 | H | H | CH₃ | CH₃ | *2.24, 2.27 (2 s, 6 H, Ar—CH₃) 3.21 (s, 3 H, OCH₃) 3.55 (s, 3 H, CO₂CH₃) 3.81 (s, 3 H, Ar—OCH₃) | β |
| II-26 | CH₃ | CH₃ | 4-Cl | H | 3' | 0 | H | H | CH₃ | CH₃ | 146 | β |
| II-27 | CH₃ | C₂H₅ | 4-Br | H | 3' | 0 | H | H | CH₃ | CH₃ | **3.25 (s, 3 H, CH₂—O—CH₃) 3.70 (s, 3 H, CO₂CH₃) 7.20 (m, 2 H, Ar—H) | β |
| II-28 | CH₃ | CH₃ | 5-(4-Cl—Ph) | H | 4' | 0 | H | H | CH₃ | CH₃ | *2.16, 2.35 (2 s, 6 H, Ar—CH₃) 3.24 (s, 3 H, OCH₃) 7.24-7.27 (m, AA', 2 H, Ar—H) 7.40-7.43 (m, BB', 2 H, Ar—H) | β |
| II-29 | CH₃ | CH₃ | 4-CH₃ | 5-CH₃ | 4' | 0 | H | H | CH₃ | CH₃ | 107 | β |
| II-30 | H | CH₃ | 4-CH₃ | 5-CH₃ | 4' | 0 | H | H | CH₃ | CH₃ | 133 | β |
| II-31 | CH₃ | CH₃ | 4-Cl | H | 4' | 0 | H | H | CH₃ | CH₃ | 172 | β |
| II-32 | CH₃ | CH₃ | 4-Br | H | 4' | 0 | H | H | CH₃ | CH₃ | 179 | β |
| II-33 | CH₃ | CH₃ | 4-I | H | 4' | 0 | H | H | CH₃ | CH₃ | 182 | β |
| II-34 | CH₃ | Cl | 4-Cl | H | 4' | 0 | H | H | CH₃ | CH₃ | 160 | β |
| II-35 | Cl | Cl | 4-Cl | H | 4' | 0 | H | H | CH₃ | CH₃ | 153 | β |
| II-36 | H | Br | H | 5-CH₃ | 4' | 0 | H | H | CH₃ | CH₃ | wax | β |
| II-37 | CH₃ | OCH₃ | H | H | 4' | 0 | H | H | CH₃ | CH₃ | 98 | β |
| II-38 | H | Cl | 5-(4-Cl—Ph) | H | 4' | 0 | H | H | CH₃ | CH₃ | wax | β |
| II-39 | H | CH₃ | 4-Cl | 5-CH₃ | 4' | 0 | H | H | CH₃ | CH₃ | 146 | β |
| II-40 | C₂H₅ | Br | 4-CH₃ | H | 4' | 1 | H | H | CH₃ | CH₃ | 103-107 | β |
| II-41 | C₂H₅ | OC₂H₅ | 4-Cl | H | 4' | 1 | H | H | CH₃ | CH₃ | 123-125 | β |
| II-42 | C₂H₅ | OCH₃ | 4-Cl | H | 4' | 1 | H | H | CH₃ | CH₃ | 124-127 | β |
| II-43 | OCH₃ | Cl | 4-CH₃ | H | 4' | 1 | H | H | CH₃ | CH₃ | 119-122 | β |
| II-44 | CH₃ | CH₃ | 4-Br | H | 4' | 1 | H | H | CH₃ | CH₃ | 141 | β |
| II-45 | H | CH₃ | 5-(4-Cl—Ph) | H | 4' | 1 | H | H | CH₃ | CH₃ | 125 | β |
| II-46 | CH₃ | CH₃ | 4-CH₃ | H | 4' | 1 | H | H | CH₃ | CH₃ | 111 | β |
| II-47 | H | CH₃ | H | 5-CH₃ | 4' | 1 | H | H | CH₃ | CH₃ | 84 | β |
| II-48 | CH₃ | CH₃ | 4-Cl | H | 4' | 1 | H | H | CH₃ | CH₃ | 124 | β |
| II-49 | CH₃ | CH₃ | 4-I | H | 4' | 1 | H | H | CH₃ | CH₃ | 152 | β |
| II-50 | H | CH₃ | 4-Cl | 5-CH₃ | 4' | 1 | H | H | CH₃ | CH₃ | 142 | β |
| II-51 | CH₃ | CH₃ | 5-(4-Cl—Ph) | H | 4' | 1 | H | H | CH₃ | CH₃ | 147 | β |
| II-52 | CH₃ | CH₃ | 4-CH₃ | H | 3' | 1 | H | H | CH₃ | CH₃ | 81 | β |
| II-53 | CH₃ | CH₃ | 4-Cl | H | 3' | 1 | H | H | CH₃ | CH₃ | 132 | β |
| II-54 | H | CH₃ | H | 5-CH₃ | 3' | 1 | H | H | CH₃ | CH₃ | oil | β |
| II-55 | CH₃ | CH₃ | 4-Br | H | 3' | 1 | H | H | CH₃ | CH₃ | 136 | β |
| II-56 | CH₃ | CH₃ | 5-(4-Cl—Ph) | H | 3' | 1 | H | H | CH₃ | CH₃ | *2.15, 2.34 (2 s, 6 H, Ar—CH₃) 3.20 (s, 3 H, OCH₃) 7.01 7.10 (2d, 2 H, Ar—H) | β |

-continued

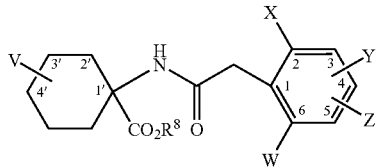

(II)

| Ex. No. | W | X | Y | Z | V | m | Q¹ | Q² | A | R⁸ | m.p. ° C. | Isomer |
|---|---|---|---|---|---|---|---|---|---|---|---|---|
| II-57 | $C_2H_5$ | Br | 4-$CH_3$ | H | 3' | 1 | H | H | $CH_3$ | $CH_3$ | **3.27 (s, 3 H, O$\underline{CH_3}$)<br>3.64 (s, 3 H, COO$\underline{CH_3}$)<br>7.01 7.31 (each s, 1 H, Ar—$\underline{H}$) | β |
| II-58 | $C_2H_5$ | $OC_2H_5$ | 4-Cl | H | 3' | 1 | H | H | $CH_3$ | $CH_3$ | ***3.27 (s, 3 H, O$\underline{CH_3}$)<br>3.63 (s, 3 H, COO$\underline{CH_3}$)<br>6.77, 6.89 (each s, 1 H, Ar—$\underline{H}$) | β |
| II-59 | $C_2H_5$ | $OCH_3$ | 4-Cl | H | 3' | 1 | H | H | $CH_3$ | $CH_3$ | ***3.29 (s, 3 H, $CH_2$—O$\underline{CH_3}$)<br>3.64 (s, 3 H, COO$\underline{CH_3}$)<br>6.78, 6.88 (each s, 1 H, Ar—$\underline{H}$) | β |
| II-60 | $OCH_3$ | Cl | 4-$CH_3$ | H | 3' | 1 | H | H | $CH_3$ | $CH_3$ | ***3.29 (s, 3 H, $CH_2$—O$\underline{CH_3}$)<br>3.65 (s, 3 H, COO$\underline{CH_3}$)<br>6.63, 6.86 (each s, 1 H, Ar—$\underline{H}$) | β |

*¹H-NMR (400 MHz, $CD_3CN$): shift δ in ppm
**¹H-NMR (400 MHz, $CDCl_3$): shift δ in ppm
***¹H-NMR (400 MHz, $d_6$-DMSO): shift δ in ppm Example I-2-a-1

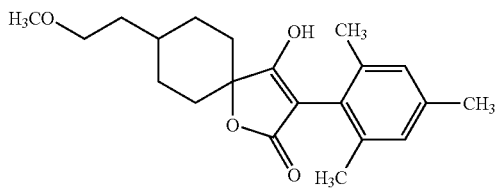

The crude product of Example III-1 is dissolved in 8 ml of DMF. At room temperature, 336 mg (3 mmol) of potassium tert-butoxide (as a 1M solution in DMF) are added dropwise, and the mixture is stirred at room temperature for another 6 h. The DMF is removed using a rotary evaporator and the residue is dissolved in water. The mixture is extracted with ethyl acetate, the aqueous phase is acidified with HCl and the product is filtered off with suction.

Yield: 680 mg (97% of theory), m.p. 143-145° C.

Analogously to Example (I-2-a-1) and in accordance with the general statements on the preparation, the following compounds of the formula (I-2-a) where

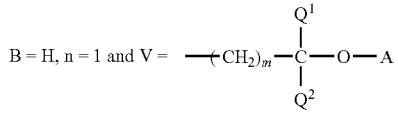

are obtained

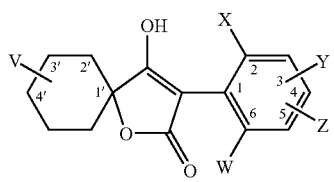

(I-2-a)

| Ex. No. | W | X | Y | Z | V | m | Q¹ | Q² | A | m.p. ° C./log P |
|---|---|---|---|---|---|---|---|---|---|---|
| I-2-a-2 | H | $CH_3$ | 5-(4-Cl-Ph) | H | 3' | 0 | H | H | $CH_3$ | oil/3.58 |
| I-2-a-3 | $CH_3$ | $CH_3$ | 4-Br | H | 3' | 0 | H | H | $CH_3$ | 238 |
| I-2-a-4 | $CH_3$ | $CH_3$ | 4-Cl | H | 3' | 0 | H | H | $CH_3$ | 88-100 |
| 1-2-a-5 | H | $CH_3$ | 4-$CH_3$ | 5-$CH_3$ | 3' | 0 | H | H | $CH_3$ | oil/2.78 |
| I-2-a-6 | $CH_3$ | $CH_3$ | 4-$CH_3$ | H | 3' | 0 | H | H | $CH_3$ | 210 |
| I-2-a-7 | $C_2H_5$ | $C_2H_5$ | 4-Br | H | 3' | 0 | H | H | $CH_3$ | oil/3.44 |
| I-2-a-8 | H | $CH_3$ | 5-(4-Cl-Ph) | H | 4' | 0 | H | H | $CH_3$ | 115-118 |
| I-2-a-9 | $CH_3$ | $CH_3$ | 4-Br | H | 4' | 0 | H | H | $CH_3$ | 198 |
| I-2-a-10 | $CH_3$ | $CH_3$ | 4-Cl | H | 4' | 0 | H | H | $CH_3$ | 200 |
| I-2-a-11 | H | $CH_3$ | 4-$CH_3$ | 5-$CH_3$ | 4' | 0 | H | H | $CH_3$ | oil/2.72 |
| I-2-a-12 | $CH_3$ | $CH_3$ | 4-$CH_3$ | H | 4' | 0 | H | H | $CH_3$ | oil/2.69 |
| I-2-a-13 | $C_2H_5$ | $C_2H_5$ | 4-Br | H | 4' | 0 | H | H | $CH_3$ | oil/3.38 |
| I-2-a-14 | $C_2H_5$ | $C_2H_5$ | 4-$CH_3$ | H | 4' | 0 | H | H | $CH_3$ | oil/3.19 |
| I-2-a-15 | H | $CH_3$ | 4-(4-Cl-Ph) | 5-$CH_3$ | 4' | 0 | H | H | $CH_3$ | 187-190 |

-continued (I-2-a)

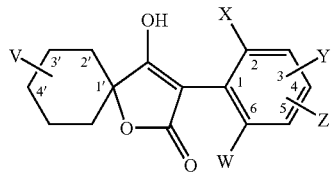

| Ex. No. | W | X | Y | Z | V | m | Q¹ | Q² | A | m.p. °C./log P |
|---|---|---|---|---|---|---|---|---|---|---|
| I-2-a-16 | H | Cl | 5-(4-Cl-Ph) | H | 4' | 0 | H | H | $CH_3$ | 118-120 |
| I-2-a-17 | $CH_3$ | $CH_3$ | 5-(4-Cl-Ph) | H | 4' | 0 | H | H | $CH_3$ | >260 |
| I-2-a-18 | H | $CH_3$ | 5-(4-Cl-Ph) | H | 3' | 1 | H | H | $CH_3$ | oil/3.75 |
| I-2-a-19 | $CH_3$ | $CH_3$ | 4-Br | H | 3' | 1 | H | H | $CH_3$ | oil/3.13 |
| I-2-a-20 | $CH_3$ | $CH_3$ | 4-Cl | H | 3' | 1 | H | H | $CH_3$ | oil/3.03 |
| I-2-a-21 | H | $CH_3$ | 4-$CH_3$ | 5-$CH_3$ | 3' | 1 | H | H | $CH_3$ | oil/2.96 |
| I-2-a-22 | $CH_3$ | $CH_3$ | 4-$CH_3$ | H | 3' | 1 | H | H | $CH_3$ | oil/2.94 |
| I-2-a-23 | $C_2H_5$ | $C_2H_5$ | 4-Br | H | 3' | 1 | H | H | $CH_3$ | oil/3.63 |
| I-2-a-24 | $C_2H_5$ | $C_2H_5$ | 4-$CH_3$ | H | 3' | 1 | H | H | $CH_3$ | oil/3.44 |
| I-2-a-25 | H | $CH_3$ | 4-(4-Cl-Ph) | 5-$CH_3$ | 3' | 1 | H | H | $CH_3$ | oil/4.03 |
| I-2-a-26 | H | Cl | 5-(4-Cl-Ph) | H | 3' | 1 | H | H | $CH_3$ | oil/3.68 |
| I-2-a-27 | $CH_3$ | $CH_3$ | 5-(4-Cl-Ph) | H | 3' | 1 | H | H | $CH_3$ | 225 |
| I-2-a-28 | H | $CH_3$ | 5-(4-Cl-Ph) | H | 4' | 1 | H | H | $CH_3$ | oil/3.71 |
| I-2-a-29 | $CH_3$ | $CH_3$ | 4-Br | H | 4' | 1 | H | H | $CH_3$ | oil/3.10 |
| I-2-a-30 | $CH_3$ | $CH_3$ | 4-Cl | H | 4' | 1 | H | H | $CH_3$ | oil/3.00 |
| I-2-a-31 | H | $CH_3$ | 4-$CH_3$ | 5-$CH_3$ | 4' | 1 | H | H | $CH_3$ | oil/2.92 |
| I-2-a-32 | $C_2H_5$ | $C_2H_5$ | 4-Br | H | 4' | 1 | H | H | $CH_3$ | oil/3.59 |
| I-2-a-33 | $C_2H_5$ | $C_2H_5$ | 4-$CH_3$ | H | 4' | 1 | H | H | $CH_3$ | oil/3.40 |
| I-2-a-34 | H | $CH_3$ | 4-(4-Cl-Ph) | 5-$CH_3$ | 4' | 1 | H | H | $CH_3$ | 105-107 |
| I-2-a-35 | H | Cl | 5-(4-Cl-Ph) | H | 4' | 1 | H | H | $CH_3$ | oil/3.67 |

Example (I-2-b-1)

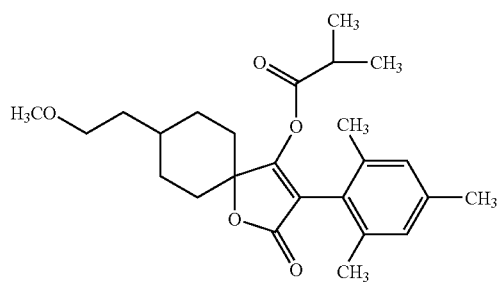

100 mg (0.290 mmol) of the compound of Example (I-2-a-1) are initially charged in 5 ml of dichloromethane, 35 mg (0.348 mmol) of triethylamine are added and 0.35 ml (0.348 mmol) of isobutyryl chloride (1M solution in dichloromethane) is added dropwise. The mixture is stirred at room temperature for 12 h and then concentrated using a rotary evaporator, and the crude product is purified by preparative HPLC (RP column, acetonitrile/water/formic acid).

Yield: 20 mg (17% of theory)

log P 4.79

Example (I-2-b-2) having a log P of 5.43 if obtained analogously

Example (I-2-c-1)

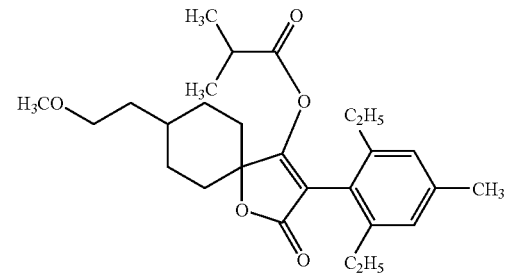

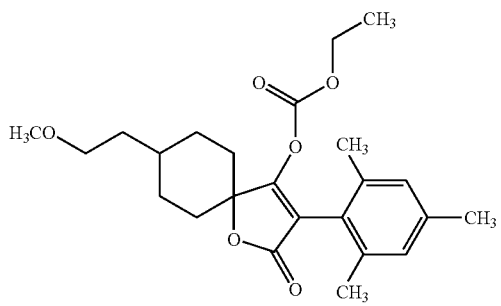

100 mg (0.290 mmol) of the compound of Example (I-2-a-1) are initially charged in 5 ml of dichloromethane, 35 mg (0.348 mmol) of triethylamine are added and 0.35 ml (0.348 mmol) of ethyl chloroformate (1M solution in dichloromethane) is added dropwise. The mixture is stirred at room temperature for 12 h and then concentrated using a rotary evaporator, and the crude product is purified by preparative HPLC (RP column, acetonitrile/water/formic acid).

Yield: 20 mg (17% of theory)

Analogously to Example (I-2-c-1) and in accordance with the general statements on the preparation, the following compounds of the formula (I-2-c) where

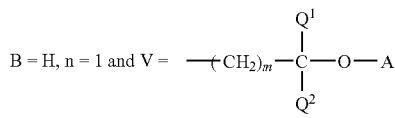

are obtained

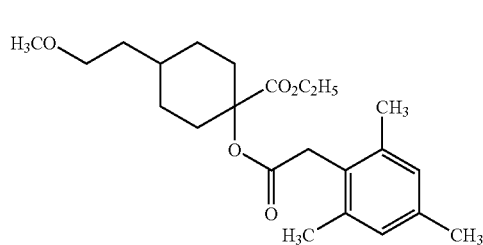

(I-2-c)

| Ex. No. | W | X | Y | Z | V | m | $Q^1$ | $Q^2$ | A | M | $R^2$ | log P |
|---|---|---|---|---|---|---|---|---|---|---|---|---|
| I-2-c-2 | H | $CH_3$ | 5-(4-Cl-Ph) | H | 4' | 0 | H | H | $CH_3$ | O | $C_2H_5$ | 4.95 |
| I-2-c-3 | $C_2H_5$ | $C_2H_5$ | 4-$CH_3$ | H | 3' | 1 | H | H | $CH_3$ | O | $C_2H_5$ | 4.97 |

Example III-1

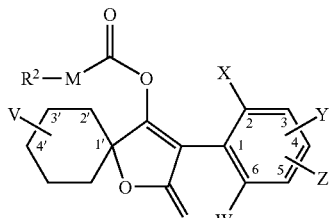

460 mg (2 mmol) of hydroxyester and 392 mg (2 mmol) of mesitylacetyl chloride are stirred at 120° C. for 6 h. After cooling, the mixture is degassed under oil pump vacuum and used for the second step.

Yield: quant.

log P: 5.01/5.13 cis/trans isomer mixture

Analogously to Example (III-1) and in accordance with the general statements on the preparation, the following compounds of the formula (III) where

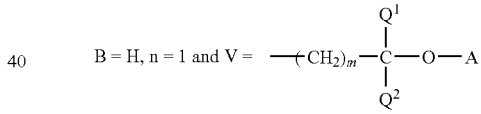

are obtained

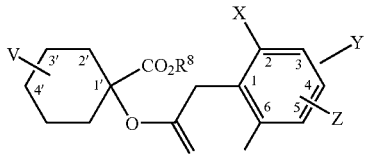

(III)

| Ex. No. | W | X | Y | Z | V | m | $Q^1$ | $Q^2$ | A | $R^8$ | log P |
|---|---|---|---|---|---|---|---|---|---|---|---|
| III-2 | H | $CH_3$ | 5-(4-Cl-Ph) | H | 3' | 0 | H | H | $CH_3$ | $C_2H_5$ | 5.50/5.58 |
| III-3 | $CH_3$ | $CH_3$ | 4-Br | H | 3' | 0 | H | H | $CH_3$ | $C_2H_5$ | 4.94/5.05 |
| III-4 | $CH_3$ | $CH_3$ | 4-Cl | H | 3' | 0 | H | H | $CH_3$ | $C_2H_5$ | 4.82/4.93 |
| III-5 | H | $CH_3$ | 4-$CH_3$ | 5-$CH_3$ | 3' | 0 | H | H | $CH_3$ | $C_2H_5$ | 4.85/4.93 |
| III-6 | $CH_3$ | $CH_3$ | 4-$CH_3$ | H | 3' | 0 | H | H | $CH_3$ | $C_2H_5$ | 4.85/4.94 |
| III-7 | $C_2H_5$ | $C_2H_5$ | 4-Br | H | 3' | 0 | H | H | $CH_3$ | $C_2H_5$ | 5.52/5.62 |
| III-8 | H | $CH_3$ | 5-(4-Cl-Ph) | H | 4' | 0 | H | H | $CH_3$ | $C_2H_5$ | 5.36/5.49 |

-continued (III)

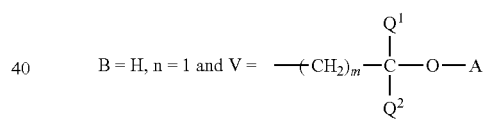

| Ex. No. | W | X | Y | Z | V | m | Q$^1$ | Q$^2$ | A | R$^8$ | log P |
|---|---|---|---|---|---|---|---|---|---|---|---|
| III-9 | CH$_3$ | CH$_3$ | 4-Br | H | 4' | 0 | H | H | CH$_3$ | C$_2$H$_5$ | 4.88/5.01 |
| III-10 | CH$_3$ | CH$_3$ | 4-Cl | H | 4' | 0 | H | H | CH$_3$ | C$_2$H$_5$ | 4.76/4.90 |
| III-11 | H | CH$_3$ | 4-CH$_3$ | 5-CH$_3$ | 4' | 0 | H | H | CH$_3$ | C$_2$H$_5$ | 4.74/4.85 |
| III-12 | CH$_3$ | CH$_3$ | 4-CH$_3$ | H | 4' | 0 | H | H | CH$_3$ | C$_2$H$_5$ | 4.76/4.88 |
| III-13 | C$_2$H$_5$ | C$_2$H$_5$ | 4-Br | H | 4' | 0 | H | H | CH$_3$ | C$_2$H$_5$ | 5.52/5.65 |
| III-14 | C$_2$H$_5$ | C$_2$H$_5$ | 4-CH$_3$ | H | 4' | 0 | H | H | CH$_3$ | C$_2$H$_5$ | 5.39/5.51 |
| III-15 | H | CH$_3$ | 4-(4-Cl-Ph) | 5-CH$_3$ | 4' | 0 | H | H | CH$_3$ | C$_2$H$_5$ | 5.90/5.98 |
| III-16 | H | Cl | 5-(4-Cl-Ph) | H | 4' | 0 | H | H | CH$_3$ | C$_2$H$_5$ | 5.52/5.67 |
| III-17 | CH$_3$ | CH$_3$ | 5-(4-Cl-Ph) | H | 4' | 0 | H | H | CH$_3$ | C$_2$H$_5$ | 5.86/5.96 |
| III-18 | H | CH$_3$ | 5-(4-Cl-Ph) | H | 3' | 1 | H | H | CH$_3$ | C$_2$H$_5$ | 5.68/5.80 |
| III-19 | CH$_3$ | CH$_3$ | 4-Br | H | 3' | 1 | H | H | CH$_3$ | C$_2$H$_5$ | 5.13/5.26 |
| III-20 | CH$_3$ | CH$_3$ | 4-Cl | H | 3' | 1 | H | H | CH$_3$ | C$_2$H$_5$ | 5.00/5.11 |
| III-21 | H | CH$_3$ | 4-CH$_3$ | 5-CH$_3$ | 3' | 1 | H | H | CH$_3$ | C$_2$H$_5$ | 4.94/5.05 |
| III-22 | CH$_3$ | CH$_3$ | 4-CH$_3$ | H | 3' | 1 | H | H | CH$_3$ | C$_2$H$_5$ | 4.94/5.05 |
| III-23 | C$_2$H$_5$ | C$_2$H$_5$ | 4-Br | H | 3' | 1 | H | H | CH$_3$ | C$_2$H$_5$ | 5.69/5.81 |
| III-24 | C$_2$H$_5$ | C$_2$H$_5$ | 4-CH$_3$ | H | 3' | 1 | H | H | CH$_3$ | C$_2$H$_5$ | 5.56/5.66 |
| III-25 | H | CH$_3$ | 4-(4-Cl-Ph) | 5-CH$_3$ | 3' | 1 | H | H | CH$_3$ | C$_2$H$_5$ | 6.03/6.12 |
| III-26 | H | Cl | 5-(4-Cl-Ph) | H | 3' | 1 | H | H | CH$_3$ | C$_2$H$_5$ | 5.67/5.82 |
| III-27 | CH$_3$ | CH$_3$ | 5-(4-Cl-Ph) | H | 3' | 1 | H | H | CH$_3$ | C$_2$H$_5$ | 6.02/6.09 |
| III-28 | H | CH$_3$ | 5-(4-Cl-Ph) | H | 4' | 1 | H | H | CH$_3$ | C$_2$H$_5$ | 5.69/5.81 |
| III-29 | CH$_3$ | CH$_3$ | 4-Br | H | 4' | 1 | H | H | CH$_3$ | C$_2$H$_5$ | 5.13/5.29 |
| III-30 | CH$_3$ | CH$_3$ | 4-Cl | H | 4' | 1 | H | H | CH$_3$ | C$_2$H$_5$ | 5.00/5.15 |
| III-31 | H | CH$_3$ | 4-CH$_3$ | 5-CH$_3$ | 4' | 1 | H | H | CH$_3$ | C$_2$H$_5$ | 5.00/5.09 |
| III-32 | C$_2$H$_5$ | C$_2$H$_5$ | 4-Br | H | 4' | 1 | H | H | CH$_3$ | C$_2$H$_5$ | 5.75/5.90 |
| III-33 | C$_2$H$_5$ | C$_2$H$_5$ | 4-CH$_3$ | H | 4' | 1 | H | H | CH$_3$ | C$_2$H$_5$ | 5.64/5.75 |
| III-34 | H | CH$_3$ | 4-(4-Cl-Ph) | 5-CH$_3$ | 4' | 1 | H | H | CH$_3$ | C$_2$H$_5$ | 6.14/6.19 |
| III-35 | H | Cl | 5-(4-Cl-Ph) | H | 4' | 1 | H | H | CH$_3$ | C$_2$H$_5$ | 5.70/5.85 |

The compounds of the formula (III) are obtained as oils and converted without further purification into the compounds of the formula (I-2-a).

Example XIV-1

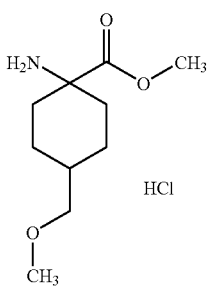

Under argon, 22 g of the compound of Example XVII-1 in 600 ml of methanol are initially charged at 0 to 5° C., and 8.5 ml of thionyl chloride are slowly added dropwise. The mixture is stirred at 0° C. for 30 minutes and at 40° C. for 1 day. The mixture is then cooled to 5° C., the precipitate is filtered off with suction and the filtrate is concentrated using a rotary evaporator. The residue is triturated with methyl tert-butyl ether and filtered off with suction. The filtrate is concentrated and the product is precipitated from dichloromethane/n-hexane.

Yield: 23 g (98% of theory)

$^1$H-NMR (400 MHz, d$_6$-DMSO): δ=3.18-3.19 (d, 2H, OCH$_2$), 3.23 (s, 3H, OCH$_3$), 3.75 (s, 3H, CO$_2$CH$_3$) ppm.

Analogously to Example (XIV-1), the following compounds of the formula (XIV) with B = H, n = 1 and V = $-(CH_2)_m-\underset{Q^2}{\overset{Q^1}{C}}-O-A$ are obtained as HCl salts

(XIV)

| Ex. No. | V | m | Q$^1$ | Q$^2$ | A | R$^8$ | m.p. ° C. | Isomer |
|---|---|---|---|---|---|---|---|---|
| XIV-2 | 3' | 0 | H | H | CH$_3$ | CH$_3$ | *3.22 (s, 3 H, OCH$_3$) 3.75 (s, 3 H, CO$_2$CH$_3$) | β |
| XIV-3 | 3' | 0 | H | H | C$_3$H$_7$ | CH$_3$ | *0.86 (t, 3 H, CH$_2$—CH$_3$) 3.75 (s, 3 H, CO$_2$CH$_3$) | β |
| XIV-4 | 3' | 1 | H | H | CH$_3$ | CH$_3$ | *3.22 (s, 3 H, OCH$_3$) 3.32-3.36 (m, 2 H, OCH$_2$) 3.75 (s 3 H, CO$_2$CH$_3$) | β |

-continued

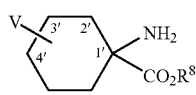

(XIV)

| Ex. No. | V | m | Q¹ | Q² | A | R⁸ | m.p. °C. | Isomer |
|---|---|---|---|---|---|---|---|---|
| XIV-5 | 4' | 1 | H | H | CH₃ | CH₃ | **3.32 (s, 3 H, OCH₃) 3.46 (t, 2 H, OCH₂) 3.84 (s, 3 H, CO₂CH₃) | β |

*¹H-NMR (400 MHz, d₆DMSO): shift δ in ppm
**¹H-NMR (400 MHz, CD₃OD): shift δ in ppm

Example XVII-1

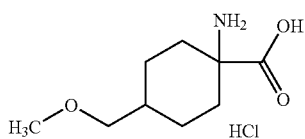

Under argon, 21 g of 8-methoxymethyl-1,3-diazaspiro[4.5]decane-2,4-dione (H-1) are suspended in 150 ml of 30% strength KOH. The mixture is stirred under reflux in an atmosphere of nitrogen.

The mixture is concentrated to about 25% of its volume and, at 0 to 10° C., the pH is adjusted to 4-5 using concentrated HCl. The solvent is distilled off and the precipitate is dried.

Without further purification and without illustration of the structure, the product is used for the reaction of Example XIV-1.

Analogously to Example (XVII-1), the following compounds of the formula (XVII) with $$B = H, n = 1 \text{ and } V = -(CH_2)_m-\underset{Q^2}{\overset{Q^1}{C}}-O-A$$

are obtained (XVII)

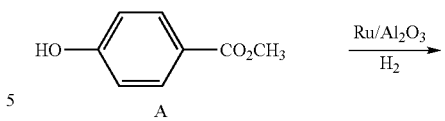

| Ex. No. | V | m | Q¹ | Q² | A | Isomer |
|---|---|---|---|---|---|---|
| XVII-2 | 3' | 0 | H | H | CH₃ | β |
| XVII-3 | 3' | 0 | H | H | C₃H₇ | β |
| XVII-4 | 3' | 1 | H | H | CH₃ | β |
| XVII-5 | 4' | 1 | H | H | CH₃ | β |

The hydantoins H and alkoxyalkylcyclohexanones G can be obtained, for example, via the following synthesis route:

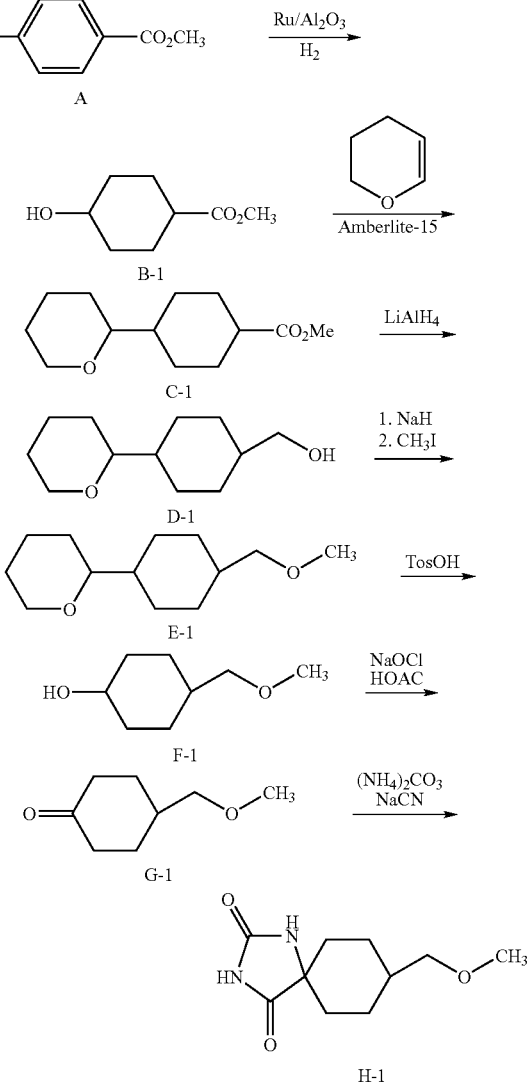

Example H-1

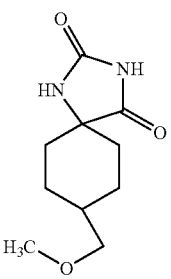

6.2 g of sodium cyanide and 48.7 g of ammonium carbonate are initially charged in 250 ml of water, 18 g of 4-methoxymethylcyclohexanone (Ex. G-1) are slowly added dropwise at room temperature and the mixture is stirred at 55 to 60° C. for about 12 to 15 hours. After cooling, n-hexane is added, the mixture is cooled to 5° C. and stirring is continued. After 3 hours, the liquid phases are discarded, and the solid is again stirred at 5° C. with n-hexane. After a number of hours, the mixture is filtered off through a suction filter and the residue is washed with n-hexane and dried.

Yield: 22.8 g (85% of theory)

$^1$H-NMR (400 MHz, DMSO-d$_6$): δ=10.47 (s, N—H); 8.32 (s, N—H); 7.89 (s, N—H); 3.26 (s, O—CH$_3$); 3.11 (d, —CH$_2$—O); 1.4-1.8 (bm, 7H); 1.1-1.25 (m, 2H) ppm.

Analogously to Example (H-1), the following examples of the formula (H) with

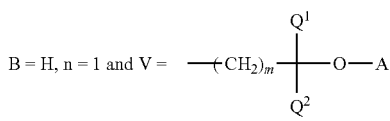

are obtained

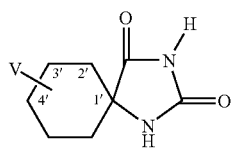

(H)

| Ex. No | V  | m | Q$^1$ | Q$^2$ | A |
|--------|----|---|-------|-------|----|
| H-2    | 3' | 0 | H     | H     | CH$_3$ |

$^1$H-NMR (400 MHz, DMSO-d$_6$): δ=10.50 (s, N—H); 8.36 (s, N—H); 7.72 (s, N—H); 3.21 (s, O—CH$_3$); 3.14 (d, —CH$_2$—O); 1.85 (m, 1H); 1.65 (m, 2H); 1.52 (m, 4H); 1.32 (m, 1H); 0.95 (m, 1H) ppm.

| Ex. No | V  | m | Q$^1$ | Q$^2$ | A |
|--------|----|---|-------|-------|----|
| H-3    | 3' | 0 | H     | H     | C$_3$H$_7$ |

$^1$H-NMR (400 MHz, DMSO-d$_6$): δ=10.50 (s, N—H); 8.35 (s, N—H); 7.72 (s, N—H); 3.29 (t, 2H); 3.17 (m, 2H); 1.84 (m, 1H); 1.66 (m, 2H); 1.51 (bm, 6H); 1.33 (m, 1H); 0.95 (m, 1H); 0.85 (t, 3H,) ppm.

| Ex. No | V  | m | Q$^1$ | Q$^2$ | A |
|--------|----|---|-------|-------|----|
| H-4    | 3' | 1 | H     | H     | CH$_3$ |

$^1$H-NMR (400 MHz, d$_6$-DMSO): δ=0.85 (m, 1H); 1.30 (t, 1H); 1.38-1.43 (m, 2H); 1.45-1.56 (m, 4H); 1.59-1.71 (m, 3H); 3.21 (s, 3H, OCH$_3$); 3.33 (t, 2H, O—CH$_2$); 8.18 (br, 1H, NHCO); 9.8-10.5 (vb, 1H, CO—NH—CO) ppm.

| Ex. No | V  | m | Q$^1$ | Q$^2$ | A |
|--------|----|---|-------|-------|----|
| H-5    | 4' | 1 | H     | H     | CH$_3$ |

$^1$H-NMR (400 MHz, d$_6$-DMSO): δ=1.18-1.29 (m, 2H); 1.31-1.52 (m, 5H); 1.59-1.66 (m, 4H); 3.22 (s, 3H, OCH$_3$); 3.36 (t, 2H, OCH$_2$); 7.73, 8.18 (2s, br, 1H, CONH); 9.9-10.6 (vb, 1H, CO—NH—CO) ppm.

Example G-1

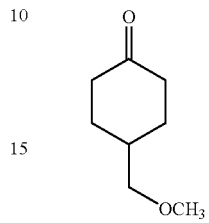

43.26 g of the compound of Example F-1 are initially charged in 300 ml of glacial acetic acid, and 343.5 g of sodium hypochloride are added dropwise at most 15° C. The mixture is stirred at 15° C. for 1 hour, residual chlorine is then flushed out with argon, the solution is stirred into 500 ml of ice-water, the mixture is extracted 3× with 200 ml of DCM and the organic phase is washed 3× with 150 ml of 1 M NaOH solution and then with in each case 150 ml of sat. NaHCO$_3$ solution and NaCl solution, dried and concentrated using a rotary evaporator.

Yield: 35 g (82% of theory)

$^1$H-NMR (400 MHz, DMSO-d$_6$): δ=3.30 (d, —CH$_2$—O); 3.26 (s, O—CH$_3$); 2.37 (m, 2H); 2.21 (m, 2H); 2.00 (m, 3H); 1.41 (m, 2H) ppm.

Analogously to Example (G-1), the following examples of the formula (G) with

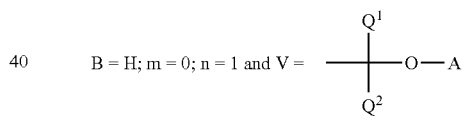

are obtained

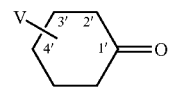

| Ex. No | V  | Q$^1$ | Q$^2$ | A |
|--------|----|-------|-------|----|
| G-2    | 3' | H     | H     | CH$_3$ |

$^1$H-NMR (400 MHz, DMSO-d$_6$): δ=10.50 (s, N—H); 8.36 (s, N—H); 7.72 (s, N—H); 3.21 (s, O—CH$_3$); 3.14 (d, —CH$_2$—O); 2.04-2.29 (bm, 4H); 1.97 (m, 2H); 1.78 (m, 1H); 1.59 (m, 1H); 1.41 (m, 1H) ppm.

| Ex. No | V  | Q$^1$ | Q$^2$ | A |
|--------|----|-------|-------|----|
| G-3    | 3' | H     | H     | C$_3$H$_7$ |

$^1$H-NMR (400 MHz, DMSO-$d_6$): δ=3.31 (t, 2H); 3.27 (m, 2H); 2.26 (m, 2H); 2.16 (m, 1H); 1.98 (m, 2H); 1.50 (bm, 5H); 0.86 (t, 3H) ppm.

Example F-1

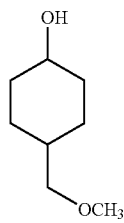

68.5 g of the compound of Example E-1 are dissolved in 300 ml of methanol, 3.1 g of 4-toluene-sulphonic acid dihydrate are added and the mixture is stirred at room temperature. Once all the starting material has been consumed, 1.5 g of NaHCO$_3$ in 50 ml of water are added for work-up, and the mixture is concentrated on a rotary evaporator almost to dryness. The residue is taken up in 100 ml of water and 200 ml of ethyl acetate and extracted 3× with 150 ml of ethyl acetate, and the extracts are dried over Na$_2$SO$_4$ and reconcentrated using a rotary evaporator.

Yield: 46 g

Example E-1

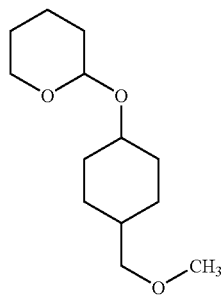

15.6 g of sodium hydride are initially charged in 450 ml of tetrahydrofuran; and 64 g of the compound of Example D-1, dissolved in 150 ml of tetrahydrofuran, are added dropwise at room temperature. The mixture is heated at 60° C. for 1 hour and then allowed to cool, and 85.2 g of methyl iodide are added at room temperature. The mixture is stirred at room temperature overnight.

For work-up, 300 ml of sat. ammonium chloride solution are added carefully, the phases are separated, the aqueous phase is extracted 3× with 200 ml of methyl tert-butyl ether, and the combined org. phases are washed with 200 ml of sat. NaCl solution and dried.

Yield: 71.2 g crude yield

Without further purification and characterization, the compound was used for preparing Example F-1.

Example D-1

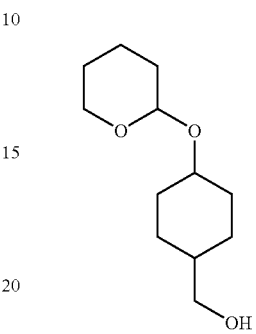

17 g of lithium aluminium hydride are initially charged in 600 ml of tetrahydrofuran and cooled to 0° C., and a solution of 72.6 g of the compound of Example C-1 in 300 ml of tetrahydrofuran is slowly added dropwise. The solution is stirred at 0° C. for 3 hours, and first 29 ml of ethyl acetate are slowly added dropwise, followed by 18 ml of water, 18 ml of 15% strength NaOH and another relatively large amount (54 ml) of water. The ice-bath is removed and the reaction is stirred for another hour. The precipitated solid is filtered off through a suction filter and washed with ether, and the organic phases are dried and concentrated using a rotary evaporator.

Yield: 69.5 g of crude material which were used without further purification for preparing Example E-1.

Example C-1

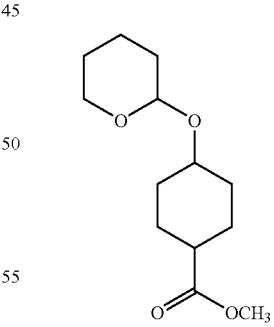

50 g of the compound of Example B-1 are dissolved in 23 ml of dihydropyran, 5 g of Amberlyst-15 are added and the mixture is stirred for 2 hours and diluted with 300 ml of dichloromethane. Once no more starting material is present, the Amberlyst is filtered off and the filtrate is evaporated to dryness using a rotary evaporator.

Yield: 78 g (69.5% of theory) of crude material which were used without further purification for preparing Example D-1.

Example B-1

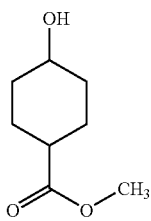

200 g of methyl 4-hydroxybenzoate in 1200 ml of methanol are hydrogenated using 20 g of 5% Ru on Al$_2$O$_3$ (Escat 44) at 120° C./120 bar of hydrogen until no more hydrogen is taken up.

For work-up, the mixture is filtered through Celite and concentrated using a rotary evaporator.

Yield: 200.6 g (96.5% of theory). Without further purification, the crude product was used for preparing Example C-1.

The methoxyethylcyclohexanones can be obtained, for example, via the following synthesis route:

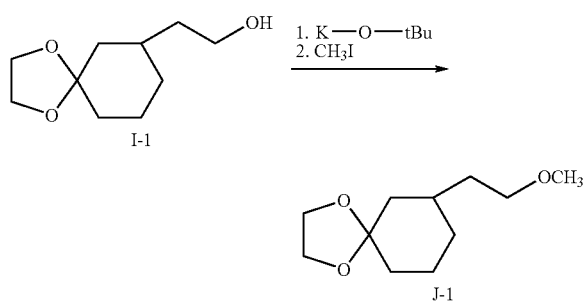

The compound I-1 is known, for example, from S. J. Etheredge J. Org. Chem. 31, 1990 ff. 1966

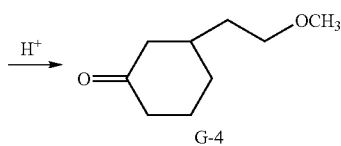

Analogously, G-5 is obtained from I-2

The compound I-2 is known, for example, from M. A. Cinfolini, N. E. Byrne, J.A.C.S. 113, 8016-8024, 1991

Example G-4

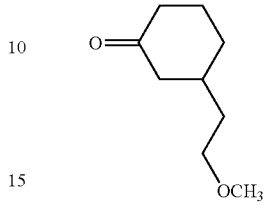

Under argon, 20 g of the compound J-1 in 50 ml of tetrahydrofuran and 50 ml of 10% strength trifluoroacetic acid are stirred at 60° C. for one day, the mixture is then extracted with dichloromethane and the extract is concentrated using a rotary evaporator.

Yield: 12.8 g (78% of theory)

$^1$H-NMR (400 MHz, CD$_3$CN): δ=1.36-1.48 (m, 2H); 1.50-1.63 (m, 3H); 2.22-2.34 (m, 3H); 3.25 (s, 3H, OCH$_3$); 3.38 (t, 2H, OCH$_2$) ppm.

Analogously to Example G-4, Example G-5 is obtained

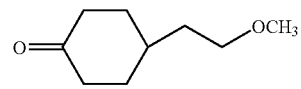

$^1$H-NMR (400 MHz, CD$_3$CN): δ=1.34-1.44 (m, 2H); 1.55 ("q", 2H); 1.83-1.89 (m, 1H); 2.21-2.37 (m, 4H); 3.27 (s, 3H, OCH$_3$); 3.42 (t, 2H, OCH$_2$) ppm.

Example J-1

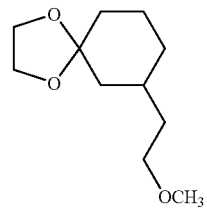

Under argon, 5.9 g of potassium tert-butoxide are initially charged in 50 ml of anhydrous tetrahydrofuran. At 20° C., 9.3 g of the compound I-1 in 10 ml of anhydrous tetrahydrofuran are added dropwise. The mixture is stirred for 5 minutes, 7.8 g of iodomethane are added dropwise and the mixture is stirred under reflux. The reaction is monitored by thin-layer chromatography. The product is purified by chromatography on silica gel (n-hexane/ethyl acetate 10:1 to 2:1).

Yield: 3.6 g (35% of theory)

$^1$H-NMR (400 MHz, CD$_3$CN): δ=0.86-0.93 (m, 1H); 1.13 ("t", 1H); 3.24 (s, 3H, OCH$_3$); 3.36 (t, 2H, OCH$_2$); 3.86 (s, 4H, —O—(CH$_2$)$_2$—O) ppm.

Analogously to Example J-1, Example J-2 is obtained

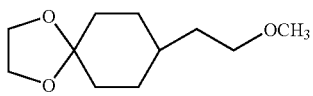

$^1$H-NMR (400 MHz, CD$_3$CN): δ=1.18-1.26 (m, 2H); 1.39-1.50 (m, 5H); 1.65-1.70 (m, 4H); 3.24 (s, 3H, OC$\underline{H}_3$); 3.37 (t, 2H, OC$\underline{H}_2$); 3.85 (s, 4H, —O—(C$\underline{H}_2$)$_2$—O) ppm.

The hydroxycarboxylic esters of the formula (XX) can be obtained from ketones G, G-1 for example, via the synthesis sequence below.

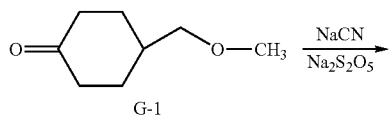

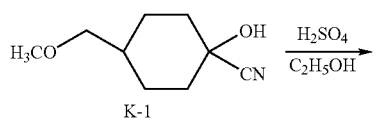

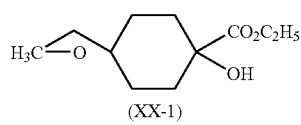

1-Hydroxy-4-methoxymethylcyclohexanecarbonitrile

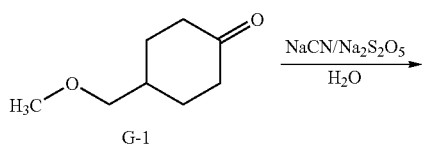

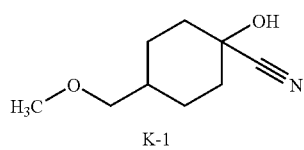

18.95 g of sodium cyanide are dissolved in 200 ml of water. At 20-28° C., 50 g of G-1 are then added dropwise over a period of 30 min, with slight cooling. The mixture is stirred at 25° C. for min, and sodium disulphite, dissolved in 150 ml of water, is then, at 25-30° C., added dropwise with cooling over a period of 30 min. The mixture is stirred at room temperature overnight. The aqueous phase is extracted 3× with in each case 150 ml of toluene. The organic phases are combined and concentrated under reduced pressure.

Yield: 54 g ($\hat{=}$91% of theory)

Ethyl 1-hydroxy-4-methoxymethylcyclohexane carboxylate

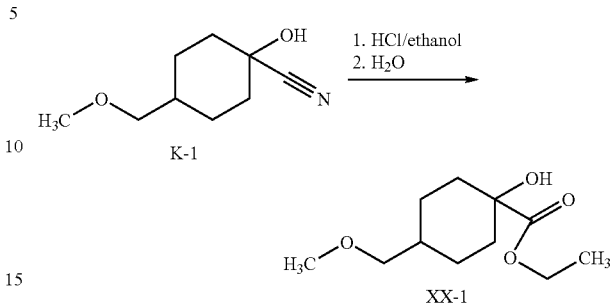

54 g of K-1 are dissolved in 200 ml of ethanol. At −20° C. (ice/sodium chloride cooling bath), HCl gas is introduced. The cooling bath is slowly thawed (ends at −5° C.). The HCl is introduced for about 5 h. The mixture is stirred without cooling overnight. The ethanol is distilled off at 45° C. 200 ml of ice-water are added to the residue, and the mixture is stirred at room temperature for 3 hours.

The reaction mixture is extracted 3 times with in each case 150 ml of methylene chloride. The combined methylene chloride phases are washed with 200 ml of saturated sodium bicarbonate solution and concentrated.

Purification is by distillation under high vacuum.

Yield: 25.47 g (37% of theory)

The following further compounds were prepared in a corresponding manner:

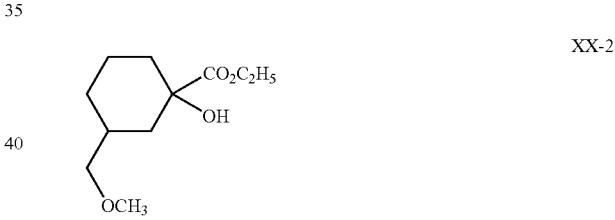

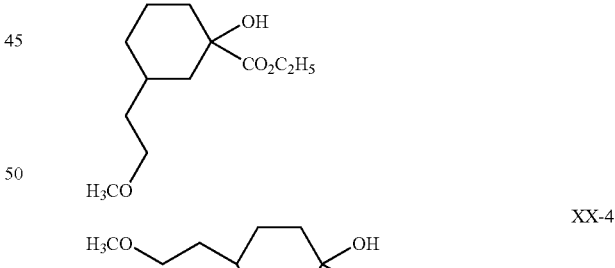

Determination of the log P Values

The log P values given in the table were determined in accordance with EEC Directive 79/831 Annex V.A8 by HPLC (High Performance Liquid Chromatography) on a reversed-phase column (C18). Temperature: 43° C.

Mobile phases for the determination in the acidic range (pH 2.3): 0.1% aqueous phosphoric acid, acetonitrile; linear gradient from 10% acetonitrile to 90% acetonitrile Calibration was carried out using unbranched alkan-2-ones (with 3 to 16 carbon atoms) whose log P values are known (determination of the log P values by the retention times using linear interpolation between two successive alkanones).

The lambda max values were determined in the maxima of the chromatographic signals using the UV spectra from 200 nm to 400 nm.

USE EXAMPLES

Example No. 1

Phaedon Test

PHAECO Spray Treatment

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha of a.i. after 7 d, an efficacy of ≧80%: I-1-a-1, I-1-a-2, I-1-a-3, I-1-a-4, I-1-a-5, I-1-a-6, I-1-a-7, I-1-a-10, I-1-a-11, I-1-a-13, I-1-a-14, I-1-a-15, I-1-a-16, I-1-a-18, I-1-a-19, I-1-a-21, I-1-a-22, I-1-a-23, I-1-a-24, I-1-a-25, I-1-a-28, I-1-a-30, I-1-a-31, I-1-a-32, I-1-a-33, I-1-a-34, I-1-a-35, I-1-a-36, I-1-a-37, I-1-a-38, I-1-a-39, I-1-a-40, I-1-a-41, I-1-a-42, I-1-a-48, I-1-a-51, I-1-a-52, I-1-a-53, I-1-a-54, I-1-a-55, I-1-a-56, I-1-a-57, I-1-a-58, I-1-a-59, I-1-a-60, I-1-b-7, I-1-b-12, I-1-b-13, I-1-b-14, I-1-b-15, I-1-b-16, I-1-b-19, I-1-b-21, I-1-b-23, I-1-c-1, I-1-c-2, I-1-c-6, I-1-c-7, I-1-c-8, I-1-c-9, I-1-c-10, I-1-c-13, I-1-c-16, I-1-c-17, I-1-c-18, I-1-c-19, I-1-c-20, I-1-c-21, I-1-c-22, I-1-c-23, I-1-c-27, I-1-c-28, I-1-c-32, I-1-c-33, I-1-c-35, I-1-c-36, I-2-a-1, I-2-a-2, I-2-a-8, I-2-a-12, I-2-a-16, I-2-a-17, I-2-a-18, I-2-a-26, I-2-a-28, I-2-b-1, I-2-c-1, I-2-c-2.

Example No. 2

Myzus Test

MYZUPE Spray Treatment

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha of a.i. after 5 d, an efficacy of ≧80%: I-1-a-1, I-1-a-2, I-1-a-3, I-1-a-5, I-1-a-6, I-1-a-7, I-1-a-8, I-1-a-9, I-1-a-10, I-1-a-11, I-1-a-12, I-1-a-13, I-1-a-14, I-1-a-15, I-1 a-17, I-1-a-19, I-1-a-21, I-1-a-22, I-1-a-23, I-1-a-24, I-1-a-25, I-1-a-26, I-1-a-27, I-1-a-28, I-1-a-29, I-1-a-30, I-1-a-31, I-1-a-32, I-1-a-33, I-1-a-34, I-1-a-35, I-1-a-36, I-1-a-37, I-1-a-38, I-1-a-39, I-1-a-40, I-1-a-41, I-1-a-42, I-1-a-44, I-1-a-45, I-1-a-46, I-1-a 48, I-1-a-50, I-1-a-51, I-1-a-52, I-1-a 53, I-1-a-54, I-1-a-55, I-1-a-56, I-1-a-57, I-1-a-58, I-1-a-59, I-1-a 60, I-1-b-1, I-1-b-5, I-1-b-6, I-1-b-7, I-1-b-11, I-1-b-12, I-1-b-13, I-1-b-14, I-1-b-15, I-1-b-16, I-1-b-17, I-1-b-19, I-1-b-21, I-1-b-22, I-1-b-23, I-1-c-1, I-1-c-2, I-1-c-4, I-1-c-5, I-1-c-6, I-1-c-7, I-1-c-8, I-1-c-9, I-1-c-10, I-1-c-11, I-1-c-12, I-1-c-13, I-1-c-16, I-1-c-17, I-1-c-18, I-1-c-19, I-1-c-20, I-1-c-21, I-1-c-22, I-1-c-23, I-1-c-24, I-1-c-27, I-1-c-28, I-1-c-31, I-1-c-32, I-1-c-33, I-1-c-35, I-1-c-36, I-2-a-1, I-2-a-2, I-2-a-3, I-2-a-4, I-2-a-5, I-2-a-6, I-2-a-8, I-2-a-9, I-2-a-10, I-2-a-11, I-2-a-12, I-2-a-13, I-2-a-14, I-2-a-16, I-2-a-17, I-2-a-18, I-2-a-20, I-2-a-21, I-2-a-22, I-2-a-24, I-2-a-26, I-2-a-28, I-2-a 29, I-2-a-31, I-2-a-33, I-2-a-34, I-2-a-35, I-2-b-1, I-2-c-1, I-2-c-2, I-2-c-3.

Example No. 3

*Spodoptera frugiperda* Test

SPODFR Spray Treatment

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Disks of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha of a.i. after 7 d, an efficacy of ≧80%: I-1-a-2, I-1-a-5, I-1-a-11, I-1-a-14, I-1-a-21, I-1-a-22, I-1-a-24, I-1-a-28, I-1-a-33, I-1-a-34, I-1-a-35, I-1-a 37, I-1-a 38, I-1-a-42, I-1-a-51, I-1-a-52, I-1-a-53, I-1-a-54, I-1-a-55, I-1-a-56, I-1-a-58, I-1-b-13, I-1-b-14, I-1-b-15, I-1-b-16, I-1-b-21, I-1-b-23, I-1-c-1, I-1-c-8, I-1-c-17, I-1-c-18, I-1-c-19, I-1-c-20, I-1-c-22, I-1-c-23, I-1-c-31, I-1-c-32, I-1-c-33, I-1-c-36, I-2-a-1, I-2-a-8, I-2-a-12, I-2-a-17, I-2-a-27, I-2-a-28, I-2-b-1, I-2-c-1, I-2-c-2.

Example No. 4

*Tetranychus* Test; OP Resistant

TETRUR Spray Treatment

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Disks of bean leaves (*Phaseolus vulgaris*) which are infested by all stages of the greenhouse rat spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha of a.i. after 5 d, an efficacy of ≧80%: I-1-a-2, I-1-a-7, I-1-a-11, I-1-a-14, I-1-a-20, I-1-a-27, I-1-a-28, I-1-a-36, I-1-a-38, I-1-a-39, I-1-a-41, I-1-a-42, I-1-a-44, I-1-a-45, I-1-a-46, I-1-a-51, I-1-a-52, I-1-a-53, I-1-a-55, I-1-a-56, I-1-b-1, I-1-b-9, I-1-b-11, I-1-b-16, I-1-b-21, I-1-b-23, I-1-c-10, I-1-c-11, I-1-c-12, I-1-c-13, I-1-c-16, I-1-c-18, I-1-c-21, I-1-c-23, I-1-c-24, I-1-c-27, I-1-c-33, I-1-c-36, I-2-a-1, I-2-a-2, I-2-a-3, I-2-a-6, I-2-a-7, I-2-a-8, I-2-a-10, I-2-a-11, I-2-a-12, I-2-a-17, I-2-b-1, I-2-c-2.

Example No. 5

*Myzus persicae* Test; Systemic Treatment

MYZUPE SYS

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration refers to the amount of active compound per volume unit of water (mg/l=ppm). The treated water is filled into vessels containing a pea plant (*Pisum sativum*), which is then infested with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show, at a concentration of 20 ppm, an efficacy of ≧80%: I-1-a-2, I-1-a-3, I-1-a-4, I-1-a-7, I-1-a-8, I-1-c-6.

Example No. 6

*Aphis gossypii* Test

APHIGO

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the active compound preparation of the desired concentration.

After the desired period of time, the kill in % is determined. 100% means that all aphids have been killed; 0% means that none of the aphids have been killed.

In this test, for example, the following compounds of the Preparation Examples show, at a concentration of 100 ppm, an efficacy of ≧80%: I-1-a-3, I-1-a-7, I-1-a-8, I-1-a-11, I-1-a-12, I-1-c-1, I-1-c-2, I-1-c-6, I-1-c-7.

Example No. 7

*Tetranychus* Test; OP Resistant/Systemic Treatment

TETRUR SYS

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Bean plants (*Phaseolus vulgaris*) which are heavily infested by all stages of the greenhouse rat spider mite (*Tetranychus urticae*) are watered with an active compound preparation of the desired concentration.

After the desired period of time, the activity in % is determined. 100% means that all spider mites have been killed; 0% means that none of the spider mites have been killed.

In this test, for example, the following compounds of the Preparation Examples show, at a concentration of 20 ppm, an efficacy of ≧80%: I-1-c-1, I-1-c-2.

Example No. 8

*Plutella* Test

PLUTMA

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the active compound preparation of the desired concentration and populated with caterpillars of the diamondback moth (*Plutella xylostella*) while the leaves are still moist.

After the desired period of time, the kill in % is determined. 100% means that all caterpillars have been killed; 0% means that none of the caterpillars have been killed.

In this test, for example, the following compounds of the Preparation Examples show, at a concentration of 100 ppm, an efficacy of ≧80%: I-1-a-5.

Example No. 9

*Spodoptera exigua* Test; Resistant Strain

SPODEX R

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the active compound preparation of the desired concentration and populated with caterpillars of the armyworm (*Spodoptera exigua*, resistant strain) while the leaves are still moist.

After the desired period of time, the kill in % is determined. 100% means that all caterpillars have been killed; 0% means that none of the caterpillars have been killed.

In this test, for example, the following compound of the Preparation Examples shows, at a concentration of 100 ppm, an efficacy of ≧80%: I-1-a-5.

Example No. 10

*Spodoptera exigua* Test

SPODEX

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the active compound preparation of the desired concentration and populated with caterpillars of the armyworm (*Spodoptera exigua*) while the leaves are still moist.

After the desired period of time, the kill in % is determined. 100% means that all caterpillars have been killed; 0% means that none of the caterpillars have been killed.

In this test, for example, the following compound of the Preparation Examples shows, at a concentration of 100 ppm, an efficacy of ≧80%: I-1-a-5.

Example 11

Herbicidal Pre-Emergence Action

Seeds of monocotyledonous and dicotyledonous weed and crop plants are placed in sandy loam in wood fibre pots and covered with soil. The test compounds, formulated in the form of wettable powders (WP) or as emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under good growth conditions for the test plants. The visual assessment of the damage on the test plants is carried out after a trial period of 3 weeks by comparison with untreated controls (herbicidal activity in percent (%): 100% activity=the plants have died, 0% activity=like control plants).

Herbicidal Post-Emergence Action

Seeds of monocotyledonous and dicotyledonous weed and crop plants are placed in sandy loam in wood fibre pots, covered with soil and cultivated in a greenhouse under good growth conditions. 2 to 3 weeks after sowing, the test plants are treated at the one-leaf stage. The test compounds, formulated as wettable powders (WP) or as emulsion concentrates (EC), are then, with a water application rate of 800 l/ha (converted), with 0.2% of wetting agent added, sprayed onto the green parts of the plants as an aqueous suspension. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants).

Applied by the pre-emergence method at 320 g/ha of a.i., the following compounds show an activity of ≧80% against *Lolium multiflorum* and *Setaria viridis*: I-1-a-3, I-1-a-4, I-1-a-7, I-1-a-8, I-1-a-9, I-1-a-11, I-1-a-12, I-1-a-13, I I-1-b-2, I-1-b-4, I-1-b-5, I-1-c-3, I-1-c-4, I-1-c-5, I-1-c-6, I-1-c-7, I-1-c-8.

Applied by the post-emergence method at 320 g/ha of a.i., the following compounds show an activity of ≧80% against *Avena sativa*, *Lolium multiflorum*, *Setaria viridis* and *Echinochloa crusgalli*: I-1-a-2, I-1-a-3, I-1-a-4, I-1-a-7, I-1-a-8, I-1-a-9, I-1-a-12, I-1-a-27, I-1-a-31, I-1-a-35, I-1-a-36, I-1-a-38, I-1 a-39, I-1-a-44, I-1-a-45, I-1-a-46, I-1-a-47, I-1-a-48, I-1-a-49, I-1-a-50, I-1-a-51, I-1-a-53, I-1-a 54, I-1-a-55, I-1-a-56, I-1-a-57, I-1-a-60, I-1-b-2, I-1-b-3, I-1-b-6, I-1-b-9, I-1-b-10, I-1-b-12, I-1-b-13, I-1-b-14, I-1-b-17, I-1-b-18, I-1-b-19, I-1-b-20, I-1-b-21, I-1-b-22, I-1-c-3, I-1-c-6, I-1-c-7, I-1-c-8, I-1-c-9, I-1-c-11, I-1-c-12, I-1-c-13, I-1-c-14, I-1-c-16, I-1-c-17, I-1-c-18, I-1-c-20, I-1-c-24, I-1-c-25, I-1-c-26, I-1-c-27, I-1-c-28, I-1-c-29, I-1-c-30, I-1-c-31.

Applied by the post-emergence method at 80 g/ha of a.i., the following compounds show an activity of ≧80% against *Echinochloa crus-galli*, *Lolium multiflorum* and *Setaria viridis*: I-1-a-15, I-1-a-18, I-1-a-19, I-1-a-23, I-1-a-25, I-1-a-26, I-1-a-27, I-1-a-31, I-1-a-32, I-1-a-36, I-1-a-39, I-1-a-41, I-1 a-42, I-1-a-44, I-1-a-45, I-1-a-46, I-1-a-47, I-1-a-48, I-1-a-49, I-1-a-50, I-1-a-51, I-1-a-55, I-1-a-60, I-1-b-6, I-1-b-7, I-1-b-8, I-1-b-9, I-1-b-10, I-1-b-17, I-1-b-18, I-1-b-19, I-1-b-20, I-1-b-21, I-1-c-11 I-1-c-12, I-1-c-13, I-1-c-14, I-1-c-16, I-1-c-18, I-1-c-24, I-1-c-25, I-1-c-26, I-1-c-27, I-1-c-30.

Profiling Tests

1. Herbicidal Pre-Emergence Action

Seeds of monocotyledonous and dicotyledonous weed and crop plants are placed in sandy loam soil in wood fibre pots or in plastic pots and covered with soil. The pots are watered slightly, and the soil surface is then treated with various dosages of the test compounds, formulated as wettable powders (WP) or liquid (EC), at a water application rate of 300 l/ha (converted). The pots with the plants are cultivated in a greenhouse, during the vegetation period also outdoors outside of the greenhouse, under good growth conditions. 3-4 weeks after sowing and the treatment of the pots, the activity of the preparations is rated visually in comparison to untreated controls (herbicidal activity in percent (%): 100% activity=the plants have died, 0% activity=like control plants).

Use of Safeners

If it is additionally to be tested as to whether safeners can improve the plant compatibility of test substances in the case of crop plants, the following options are used for applying the safener:

seeds of the crop plants are, before sowing, dressed with the safener substance (the amount of safener stated in percent, based on the weight of the seed)

before the application of the test substances, the pots of crop plants are sprayed with the safener at a certain application rate per hectare (usually 1 day before the application of the test substances)

the safener is applied together with the test substance as a tank mix (the amount of safener stated in g/ha or as a ratio, based on the herbicide).

By comparing the effect of the test substances on crop plants without or with safener treatment, it is possible to assess the effect of the safener substance.

2. Herbicidal Post-Emergence Action

Seeds of monocotyledonous and dicotyledonous weed and crop plants are placed in sandy loam soil in wood fibre pots or in plastic pots, covered with soil and cultivated in a greenhouse, during the vegetation period also outdoors outside of the greenhouse, under good growth conditions. 2-3 weeks after sowing, the test plants are treated at the one- to three-leaf stage. The test compounds, formulated as wettable powders (WP) or liquid (EC), are, in various dosages with a water application rate of 300 l/ha (converted), with wetting agent (0.2 to 0.3%) added, sprayed onto the plants and the surface of the soil. 3-4 weeks after the treatment of the test plants, the effect of the preparations is rated visually in comparison to untreated controls (herbicidal activity in percent (%): 100% activity=the plants have died, 0% activity=like control plants).

Use of Safeners

If it is additionally to be tested as to whether safeners can improve the plant compatibility of test substances in the case of crop plants, the following options are used for applying the safener:

- seeds of the crop plants are, before sowing, dressed with the safener substance (the amount of safener stated in percent, based on the weight of the seed)
- before the application of the test substances, the proper plants are sprayed with the safener at a certain application rate per hectare (usually 1 day before the application of the test substances)
- the safener is applied together with the test substance as a tank mix (the amount of safener stated in g/ha or as a ratio, based on the herbicide).

By comparing the effect of the test substances on crop plants without or with safener treatment, it is possible to assess the effect of the safener substance.

Container trials with cereal in a greenhouse
Mefenpyr 1 day prior to herbicide application
Post-emergence

| | 28 days after application | |
|---|---|---|
| | Application rate g of a.i./ha | Summer barley observed (%) |
| Ex. I-1-a-4 | 25 | 50 |
| Ex. I-1-a-4 + mefenpyr | 25 + 100 | 30 |

| | 10 days after application | |
|---|---|---|
| | Application rate g of a.i./ha | Summer wheat observed (%) |
| Ex. I-1-a-3 | 25 | 40 |
| | 12.5 | 20 |
| Ex. I-1-a-3 + mefenpyr | 25 + 100 | 20 |
| | 12.5 + 100 | 10 |

| | 28 days after application | |
|---|---|---|
| | Application rate g of a.i./ha | Summer barley observed (%) |
| Ex. I-1-a-3 | 25 | 60 |
| | 12.5 | 20 |
| Ex. I-1-a-3 + mefenpyr | 25 + 100 | 30 |
| | 12.5 + 100 | 10 |

Container trials with cereal in a greenhouse
Mefenpyr 1 day prior to herbicide application
Post-emergence

| | 28 days after application | |
|---|---|---|
| | Application rate g of a.i./ha | Summer wheat observed (%) |
| Ex. I-1-a-8 | 25 | 95 |
| | 12.5 | 90 |
| Ex. I-1-a-8 + mefenpyr | 25 + 100 | 60 |
| | 12.5 + 100 | 25 |

| | 28 days after application | | |
|---|---|---|---|
| | Application rate g of a.i./ha | Summer barley observed (%) | Summer wheat observed (%) |
| Ex. I-1-a-12 | 91 | 60 | 30 |
| | 46 | 30 | 20 |
| | 23 | 20 | 15 |
| | 11 | 10 | 10 |
| Ex. I-1-a-12 + mefenpyr | 91 + 100 | 10 | 10 |
| | 46 + 100 | 10 | 10 |
| | 23 + 100 | 7 | 7 |
| | 11 + 100 | 5 | 5 |

| | 28 days after application | |
|---|---|---|
| | Application rate g of a.i./ha | Summer barley observed (%) |
| Ex. I-1-b-6 | 12.5 | 70 |
| Ex. I-1-b-6 + mefenpyr | 12.5 + 100 | 30 |

Container trials with maize in the greenhouse
Ex. II-e-5 1 day prior to herbicide application
Pre-emergence

| | 28 days after application | |
|---|---|---|
| | Application rate g of a.i./ha | Maize - Arsenal observed (%) |
| Ex. I-1-a-4 | 25 | 65 |
| | 12.5 | 40 |
| Ex. I-1-a-4 + Ex. II-e-5 | 25 + 200 | 30 |
| | 12.5 + 200 | 30 |

| | 28 days after application | |
|---|---|---|
| | Application rate g of a.i./ha | Maize - Cecilia observed (%) |
| Ex. I-1-c-9 | 100 | 50 |
| Ex. I-1-c-9 + Ex. II-e-5 | 100 + 200 | 30 |

| | 28 days after application | |
|---|---|---|
| | Application rate g of a.i./ha | Maize - Arsenal observed (%) |
| Ex. I-1-c-7 | 25 | 60 |
| Ex. I-1-c-7 + Ex. II-e-5 | 25 + 200 | 25 |

| | 28 days after application | |
|---|---|---|
| | Application rate g of a.i./ha | Maize - Cecilia observed (%) |
| Ex. I-1-c-6 | 12.5 | 60 |
| Ex. I-1-c-6 + Ex. II-e-5 | 12.5 + 200 | 20 |

Example 12

Heliothis virescens Test

Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amounts of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco bud worm *Heliothis virescens* while the leaves are still moist.

After the desired period of time, the kill of the insects is determined.

Example 13

Critical Concentration Test/Soil Insects

Treatment of Transgenic Plants

Test insect: *Diabrotica balteata*-larvae in the soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

The invention claimed is:
1. A compound of formula (I)

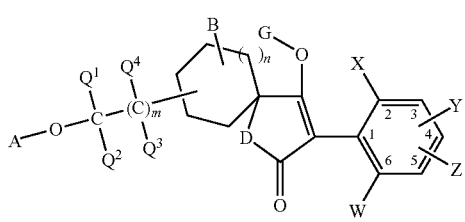

(I)

in which
W represents hydrogen, alkyl, alkenyl, alkynyl, halogen, alkoxy, haloalkyl, haloalkoxy or cyano,
X represents halogen, alkyl, alkenyl, alkynyl, alkoxy, alkoxyalkoxy, haloalkyl, haloalkoxy or cyano,
Y represents hydrogen, halogen, alkyl, alkoxy, cyano, haloalkyl, haloalkoxy; or represents in each case optionally substituted phenyl or heteroaryl,
Z represents hydrogen, halogen, alkyl, haloalkyl, cyano, alkoxy or haloalkoxy,
A represents hydrogen; represents in each case optionally halogen-substituted alkyl, alkenyl, alkynyl, alkoxyalkyl, alkylthioalkyl, saturated or unsaturated, optionally substituted cycloalkylalkyl in which optionally at least one ring atom is replaced by a heteroatom; or represents in each case optionally halogen-, alkyl-, haloalkyl-, alkoxy-, haloalkoxy-, cyano- or nitro-substituted aryl, arylalkyl, heteroaryl or heteroarylalkyl,
B represents hydrogen, alkyl or alkoxy,
D represents NH or oxygen,
$Q^1$, $Q^2$, $Q^3$ and $Q^4$ independently of one another represent hydrogen or alkyl, or
A and $Q^1$ together with the atoms to which they are attached represent a saturated or unsaturated ring which contains at least one heteroatom and is unsubstituted or substituted in the A,Q moiety,
m represents 0, 1 or 2,
n represents 0 or 1,
G represents hydrogen (a), (b)

$$\underset{R^1}{\overset{O}{\underset{\|}{\text{—C—}}}}$$

(c)

$$\underset{M}{\overset{L}{\underset{\|}{\text{—C—}}}}R^2,$$

(d)

$$\text{—SO}_2\text{—}R^3,$$

(e)

$$\underset{L}{\overset{R^4}{\underset{\|}{\text{—P}}}}\overset{}{\underset{R^5}{\text{,}}}$$

(f)

E, or (g)

$$\underset{L}{\overset{R^6}{\underset{\|}{\text{—C—N}}}}\overset{}{\underset{R^7}{\text{,}}}$$

in which
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl; represents in each case optionally halogen-, alkyl- or alkoxy-substituted cycloalkyl or heterocyclyl; or represents in each case optionally substituted phenyl, phenylalkyl, heteroaryl, phenoxyalkyl or heteroaryloxyalky,
$R^2$ represents in each case optionally halogen- or cyano-substituted alkyl, alkenyl, alkoxyalkyl or polyalkoxyalkyl; or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio; or represent in each case optionally substituted phenyl, benzyl, phenoxy or phenylthio, $R^6$ and $R^7$ independently of one another represent hydrogen; represent in each case optionally halogen- or cyano-substituted alkyl, cycloalkyl, alkenyl, alkoxy, alkoxy-alkyl; or represent in each case optionally substituted phenyl or benzyl, or together with the N atom to which they are attached form an optionally substituted ring which optionally contains oxygen or sulphur.

2. A compound of formula (I) according to claim 1 in which

W represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalky, $C_1$-$C_4$-haloalkoxy or cyano, X represents hydrogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y represents hydrogen, halogen, $C_1$-$C_6$-alkyl, $C_1$-$C_6$-alkoxy, cyano, $C_1$-$C_4$-haloalkyl, haloalkoxy; or represents $V^1$- and $V^2$-substituted phenyl or pyridyl, $V^1$ represents halogen, $C_1$-$C_{12}$-alkyl, $C_1$-$C_6$-alkoxy, $C_1$-$C_4$-haloalkyl, $C_1$-$C_4$-haloalkoxy, cyano or nitro, $V^2$ represents hydrogen, halogen, $C_1$-$C_6$-alkyl, $C_1$-$C_6$-alkoxy or $C_1$-$C_4$-haloalkyl, or $V^1$ and $V^2$ together represent $C_3$-$C_4$-alkanediyl optionally substituted by halogen and/or $C_1$-$C_2$-alkyl and optionally interrupted by one or two oxygen atoms, Z represents hydrogen, halogen, $C_1$-$C_6$-alkyl, $C_1$-$C_4$-haloalkyl, cyano, $C_1$-$C_6$-alkoxy or $C_1$-$C_4$-haloalkoxy, A represents hydrogen or in each case optionally halogen-substituted $C_1$-$C_8$-alkyl, $C_3$-$C_8$-alkenyl, $C_3$-$C_8$-alkynyl, $C_1$-$C_6$-alkoxy-$C_1$-$C_6$-alkyl, $C_1$-$C_6$-alkylthio-$C_1$-$C_6$-alkyl, optionally halogen- , $C_1$-$C_6$-alkyl- or $C_1$-$C_6$-alkoxy-substituted $C_3$-$C_8$-cycloalkyl-$C_1$-$C_4$-alkyl in which optionally one or two not directly adjacent ring members are replaced by oxygen, sulphur, or a combination of oxygen and sulphur; or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, heteroaryl having 5 to 6 ring atoms, phenyl-$C_1$-$C_4$-alkyl or heteroaryl-$C_1$-$C_4$-alkyl having 5 to 6 ring atoms, B represents hydrogen, $C_1$-$C_4$-alkyl or $C_1$-$C_4$-alkoxy, D represents NH or oxygen, $Q^1$, $Q^2$, $Q^3$ and $Q^4$ independently of one another represent hydrogen or $C_1$-$C_2$-alkyl, or A and $Q^1$ together with the atoms to which they are attached represent a saturated 5- to 6-membered ring which is interrupted by at least one heteroatom and is optionally substituted by $C_1$-$C_4$-alkyl, $C_1$-$C_4$-alkoxy, $C_1$-$C_4$-alkoxy-$C_1$-$C_2$-alkyl or $C_1$-$C_4$-haloalkyl, m represents 0, 1 or 2, n represents 0 or 1, G represents hydrogen (a),

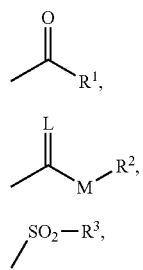

in which

E represents a metal ion or an ammonium ion,

L represents oxygen or sulphur and

M represents oxygen or sulphur, $R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl; represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen, sulphur, or a combination of oxygen and sulphur;

represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl;

represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl;

represents optionally halogen- or $C_1$-$C_6$-alkyl-substituted 5- or 6-membered heteroaryl having one or two heteroatoms selected from the group consisting of oxygen, sulphur and nitrogen;

represents optionally halogen- or $C_1$-$C_6$-alkyl-substituted phenoxy-$C_1$-$C_6$-alkyl; or represents optionally halogen-, amino- or $C_1$-$C_6$-alkyl-substituted 5- or 6-membered heteroaryloxy-$C_1$-$C_6$-alkyl having one or two heteroatoms selected from the group consisting of oxygen, sulphur and nitrogen, $R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$alkyl or poly-$C_1$-$C_8$-alkoxy-$C_2$-$C_8$-alkyl; represents optionally halogen-, $C_1$-$C_6$-alkyl- or $C_1$-$C_6$-alkoxy-substituted $C_3$-$C_8$-cycloalkyl; or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalky-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$alkoxy, $C_1$-$C_8$-alkylamino, di($C_1$-$C_8$-alkyl) amino, $C_1$-$C_8$-alkylthio or $C_3$-$C_8$-alkenylthio; or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio, $C_1$-$C_4$-alkyl- or $C_1$-$C_4$-haloalkyl-substituted phenyl, phenoxy or phenyl-thio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$- alkoxy, $C_3$-$C_8$-alkenyl or $C_1$-$C_8$-alkoxy-$C_2$-$C_8$-alkyl; represent in each case optionally halogen-, $C_1$-$C_8$-alkyl-, $C_1$-$C_8$-haloalkyl- or $C_1$-$C_8$alkoxy-substituted phenyl or benzyl; or $R^6$ and $R^7$ together represent an optionally $C_1$-$C_6$-alkyl-substituted $C_3$-$C_6$-alkylene radical in which optionally one methylene group is replaced by oxygen or sulphur.

3. A compound of formula (I) according to claim 1 in which
W represents hydrogen, fluorine, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy,
X represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano,
Y in the 4-position represents hydrogen, fluorine, chlorine, bromine, iodine, methoxy, ethoxy, cyano, trifluoromethyl, difluoromethoxy or trifluoromethoxy,
Z represents hydrogen,
A represents hydrogen, represents $C_1$-$C_6$-alkyl, $C_3$-$C_6$-alkenyl, $C_3$-$C_6$-alkynyl, $C_1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$-alkoxy,
B represents hydrogen, $C_1$-$C_2$-alkyl or $C_1$-$C_2$-alkoxy,
D represents NH or oxygen,
$Q^1$, $Q^2$, $Q^3$ and $Q^4$ independently of one another represent hydrogen or methyl, or
A and $Q^1$ together with the atoms to which they are attached represent a saturated 5- to 6-membered ring which is interrupted by at least one oxygen atom and which is optionally substituted by methyl, ethyl, methoxy, ethoxy, methoxymethyl, ethoxymethyl or trifluoromethyl,
m represents 0 or 1,
n represents 1,
G represents hydrogen (a), (b)

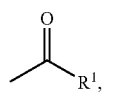

(c)

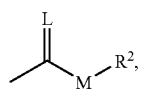

(d)

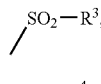

(e)

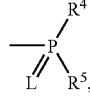

(f) E or (g)

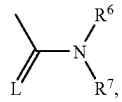

in which
E represents a metal ion or an ammonium ion,
L represents oxygen or sulphur,
M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine; represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur;
represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;
represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;
represents pyrazolyl, thiazolyl, pyridyl, pyrimidyl, furanyl or thienyl, each of which is optionally mono- to disubstituted by fluorine, chlorine, bromine or $C_1$-$C_4$-alkyl;
represents phenoxy-$C_1$-$C_5$-alkyl which is optionally mono- to disubstituted by fluorine, chlorine, bromine or $C_1$-$C_4$-alkyl; or
represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl,
$R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine,
represents $C_3$-$C_7$-cycloalkyl which is optionally mono- to disubstituted by fluorine, chlorine, $C_1$-$C_4$-alkyl or $C_1$-$C_4$-alkoxy; or
represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy,
$R^3$ represents $C_1$-$C_6$-alkyl which is optionally mono- to trisubstituted by fluorine or chlorine; or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro,
$R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine; or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl,
$R^6$ and $R^7$ independently of one another represent hydrogen; represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine; represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy; or $R^6$ and $R^7$ together represent an optionally $C_1$-$C_4$-alkyl-substituted $C_3$-$C_6$-alkylene radical in which optionally one methylene group is replaced by oxygen or sulphur.

4. A compound of formula (I) according to claim 1 in which

W represents hydrogen, chlorine, bromine, methyl, ethyl, methoxy, ethoxy or trifluoromethyl, X represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position represents hydrogen, chlorine, bromine, iodine, methoxy, trifluoromethyl or trifluoromethoxy, Z represents hydrogen, A represents hydrogen, represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine; or represents cyclopropylmethyl, cyclopentylmethyl or cyclohexylmethyl, B represents hydrogen, D represents NH or oxygen, $Q^1$, $Q^2$, $Q^3$ and $Q^4$ represent hydrogen, or A and $Q^1$ together with the atoms to which they are attached represent a saturated 5- to 6-membered ring which is interrupted by at least one oxygen atom and is optionally substituted by methyl or ethyl, m represents 0 or 1, n represents 1, G represents hydrogen (a),

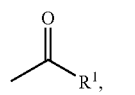
(b)

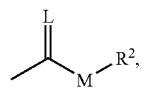
(c)

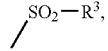
(d)

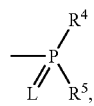
E or
(e)

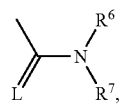
(f)

(g)

in which

E represents a metal ion or an ammonium ion,

L represents oxygen or sulphur, and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;

represents phenyl which is optionally mono- to disubstituted by fluorine, chlorine, bromine, cyano, nitro, methyl, ethyl, n-propyl, iso-propyl, methoxy, ethoxy, trifluoromethyl or trifluoromethoxy; or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;

represents cyclopentyl or cyclohexyl;

or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio; or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl; represent phenyl which is optionally mono- to disubstituted by fluorine, chlorine, bromine, methyl, methoxy or trifluoromethyl; or $R^6$ and $R^7$ together represent a $C_5$-$C_6$-alkylene radical in which optionally one methylene group is replaced by oxygen or sulphur.

5. A compound of formula (I) according to claim 1 in which

W represents chlorine, methyl or ethyl,

X represents chlorine, methyl, ethyl, methoxy or ethoxy,

Y in the 4-position represents chlorine, bromine, iodine or methoxy,

Z represents hydrogen,

A represents $C_1$-$C_4$-alkyl,

B represents hydrogen,

D represents NH or oxygen, $Q^1$, $Q^2$, $Q^3$ and $Q^4$ represent hydrogen, m represents 0 or 1, n represents 1, G represents hydrogen (a),

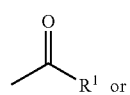
(b)

or

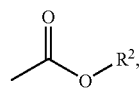
(c)

in which $R^1$ represents $C_1$-$C_{10}$-alkyl, $C_1$-$C_4$-alkoxy-$C_1$-$C_2$-alkyl or cyclopropyl, $R^2$ represents $C_1$-$C_{10}$-alkyl or benzyl.

6. A process for preparing a compound of formula (I) according to claim 1, comprising (A) obtaining a compound of formula (I-1-a)

(I-1-a)

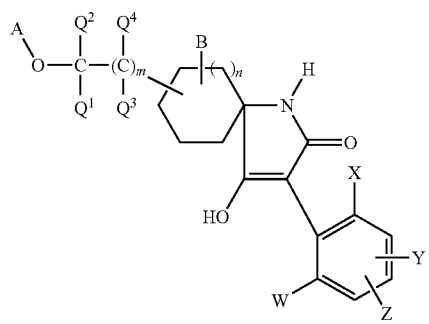

in which

A, B, m, n, $Q^1$, $Q^2$, $Q^3$, $Q^4$, W, X, Y and Z are as defined in claim 1, by the intramolecular condensation of a compound of formula (II)

(II)

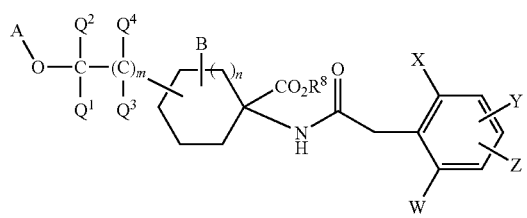

in which

A, B, m, n, $Q^1$, $Q^2$, $Q^3$, $Q^4$, W, X, Y and Z are as defined in claim 1, and $R^8$ represents alkyl, in the presence of a diluent and a base, (B) obtaining a compound of formula (I-2-a)

(I-2-a)

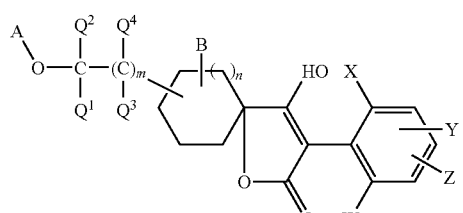

in which

A, B, m, n, $Q^1$, $Q^2$, $Q^3$, $Q^4$, W, X, Y and Z are as defined in claim 1, by the intramolecular condensation of a compound of formula (III)

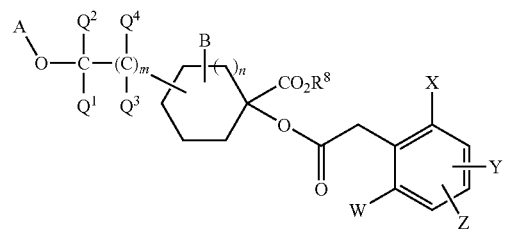

in which

A, B, m, n, $Q^1$, $Q^2$, $Q^3$, $Q^4$, W, X, Y, Z and $R^8$ are as defined in claim 1, in the presence of a diluent and a base, (C) obtaining a compound of formulae (I-1-b) or (I-2-b)

(I-1-b)

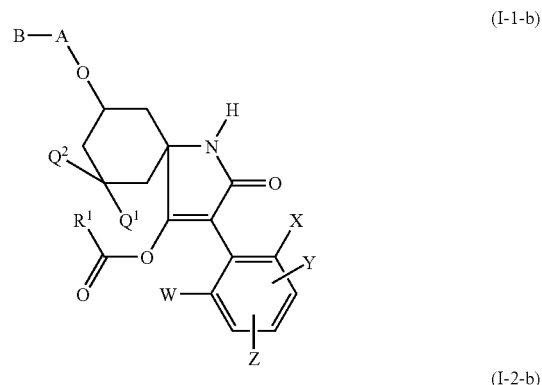

(I-2-b)

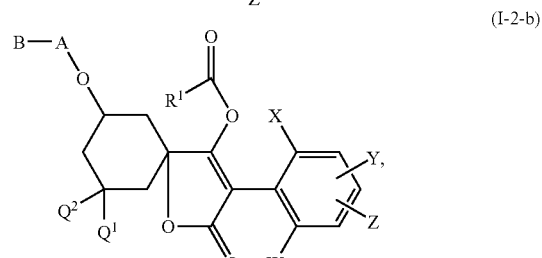

in which $R^1$, A, B, m, n, $Q^1$, $Q^2$, $Q^3$, $Q^4$, W, X, Y and Z are as defined in claim 1, by reacting a compound of formulae (I-1-a) or (I-2-a), a) with a compound of formula (IV)

(IV)

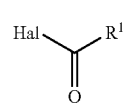

in which $R^1$ is as defined above, and

Hal represents halogen, or b) with a carboxylic anhydride of formula (V)

$R^1$—CO—O—CO—$R^1$ (V)

in which $R^1$ is as defined above, optionally in the presence of a diluent and an acid binder, (D) obtaining a compound of formulae (I-1-c) or (I-2-c)

(I-1-c)

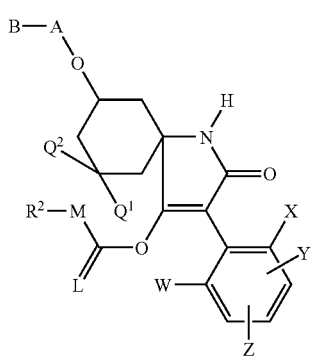

(I-2-c)

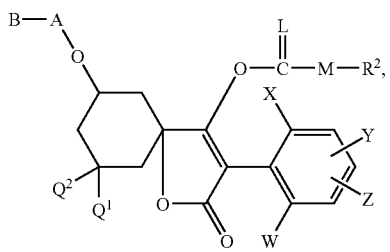

in which $R^2$, A, B, m, n, $Q^1$, $Q^2$, $Q^3$, $Q^4$, W, X, Y and Z are as defined in claim 1 and L represents oxygen, by reacting a compound of formulae (I-1-a) or (I-2-a),
with a chloroformic ester or a chloroformic thioester of formula (VI)

$$R^2\text{-M-CO-Cl} \qquad (VI)$$

in which
$R^2$ and M are as defined above,
optionally in the presence of a diluent and an acid binder,
(E) obtaining a compound of formulae (I-1-c) or (I-2-c) in which $R^2$, A, B, m, n, $Q^1$, $Q^2$, $Q^3$, $Q^4$, M, W, X, Y and Z are as defined in claim 1 and L represents sulphur, by reacting a compound of formulae (I-1-a) or (I-2-a),
with a chloromonothioformic ester or a chlorodithioformic ester of formula (VII)

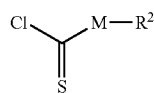

(VII)

in which
M and $R^2$ are as defined above,
optionally in the presence of a diluent and an acid binder,
(F) obtaining a compound of formulae (I-1-d) or (I-2-d)

(I-1-d)

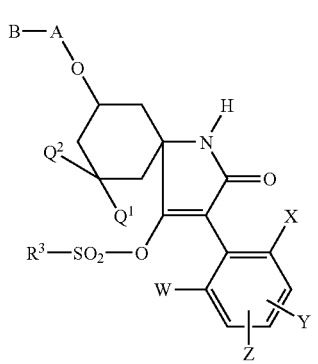

(I-2-d)

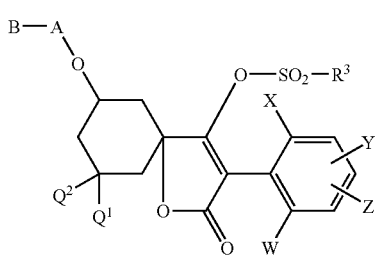

in which $R^3$, A, B, m, n, $Q^1$, $Q^2$, $Q^3$, $Q^4$, W, X, Y and Z are as defined in claim 1, by reacting a compound of formulae (I-1-a) or (I-2-a),
with a sulphonyl chloride of formula (VIII)

$$R^3\text{—SO}_2\text{—Cl} \qquad (VIII)$$

in which
$R^3$ is as defined above,
optionally in the presence of a diluent and an acid binder,
(G) obtaining a compound of formulae (I-1-e) or (I-2-e)

(I-1-e)

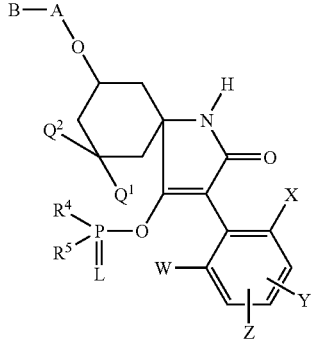

(I-2-e)

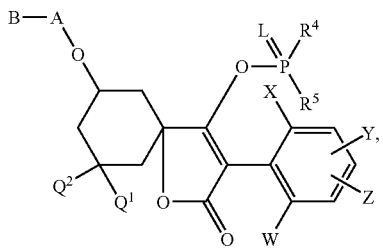

in which L, $R^4$, $R^5$, A, B, m, n, $Q^1$, $Q^2$, $Q^3$, $Q^4$, W, X, Y and Z are as defined in claim 1, by reacting a compound of formulae (1-1-a) or (I-2-a),
with a phosphorus compound of formula (IX)

(IX)

in which
L, $R^4$ and $R^5$ are as defined above, and
Hal represents halogen,
optionally in the presence of a diluent and an acid binder,
(H) obtaining a compound of formulae (I-1-f) or (I-2-f)

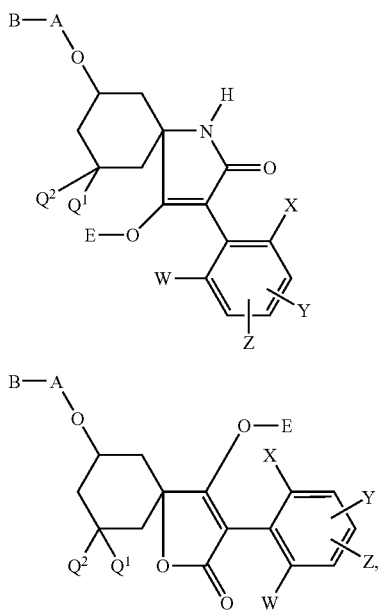

(I-1-f)

(I-2-f)

in which E, A, B, m, n, $Q^1$, $Q^2$, $Q^3$, $Q^4$, W, X, Y and Z are as defined in claim 1, by reacting a compound of formulae (I-1-a) or (I-2-a),
with a metal compound or an amine of formulae (X) and (XI), respectively,

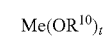

(X)

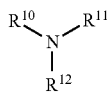

(XI)

in which
Me represents a mono- or divalent metal,
t represents 1 or 2, and
$R^{10}$, $R^{11}$, $R^{12}$ independently of one another represents hydrogen or alkyl, optionally in the presence of a diluent,
or
(I) obtaining a compound of formulae (I-1-g) or (I-2-g)

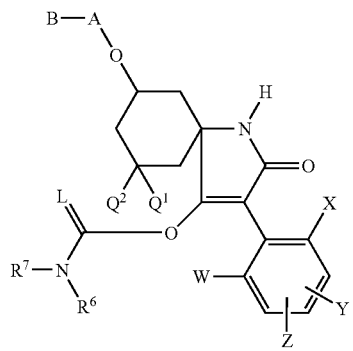

(I-1-g)

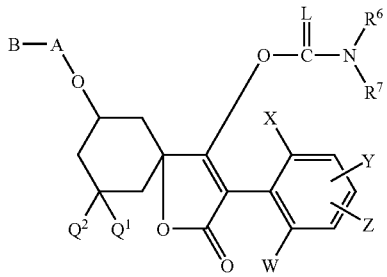

(I-2-g)

in which L, $R^6$, $R^7$, A, B, m, n, $Q^1$, $Q^2$, $Q^3$, $Q^4$, W, X, Y and Z are as defined in claim 1, by reacting a compound of formulae (I-1-a) or (I-2-a),
a) with an isocyanate or isothiocyanate of formula (XII)

(XII)

in which
$R^6$ and L are as defined above,
optionally in the presence of a diluent and a catalyst, or
b) with a carbamoyl chloride or a thiocarbamoyl chloride of formula (XIII)

(XIII)

in which
L, $R^6$ and $R^7$ are as defined above,
optionally in the presence of a diluent and an acid binder.

7. A composition comprising an effective amount of an active compound combination comprising,
(a') least one compound of formula (I) according to claim 1 and
(b') at least one crop plant compatibility-improving compound selected from the group consisting of
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethox-imino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy) propionic acid (mecoprop), diethyl 1-(2,4-dichorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl) acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl) butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1[4-(N-2-methoxybenzoylsulphamoyl)phenyl]-3-methylurea (N-(2-methoxybenzoyl)-4-[(methylaminocarbonyl)amino] benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbony)benzenesulphonamide, a compound of formula (IIa)

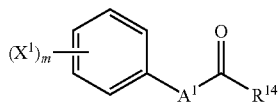

a compound of formula (IIb)

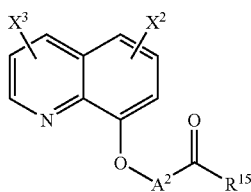

a compound of formula (IIc)

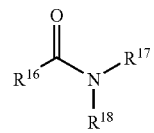

where
m represents 0, 1, 2, 3, 4 or 5,
$A^1$ represents one of the divalent heterocyclic groupings shown below

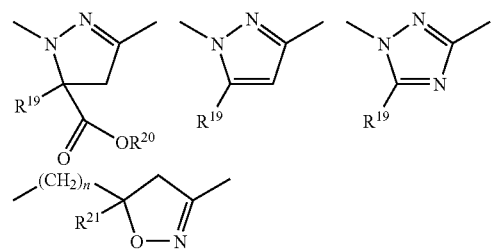

n represents 0, 1, 2, 3, 4 or 5,
$A^2$ represents optionally $C_1$-$C_4$-alkyl-, $C_1$-$C_4$-alkoxy-carbonyl-, or $C_1$-$C_4$-alkenyloxycarbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$alkyl)amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents optionally fluorine-, chlorine- or bromine-substituted $C_1$-$C_4$-alkyl,
$R^{17}$ represents hydrogen, in each case optionally fluorine-, chlorine- or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or represents optionally fluorine-, chlorine- and/or bromine- or $C_1$-$C_4$-alkyl-substituted phenyl,
$R^{18}$ represents hydrogen, in each case optionally fluorine-, chlorine- or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or represents optionally fluorine-, chlorine- and/or bromine- or $C_1$-$C_1$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, halogen, or represents in each case optionally fluorine-, chlorine- or bromine-substituted $C_1$-$C_4$-alkyl, $C_3$-$C_6$-cycloalkyl or phenyl,
$R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl,
$R^{21}$ represents hydrogen, cyano, halogen, or represents in each case optionally fluorine-, chlorine- or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$alkoxy or $C_1$-$C_4$-haloalkoxy, $X^2$ represents hydrogen, cyano, nitro, halogen, $C_1$-$C_4$-alkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-alkoxy or $C_1$-$C_4$-haloalkoxy, a compound or formula (IId)

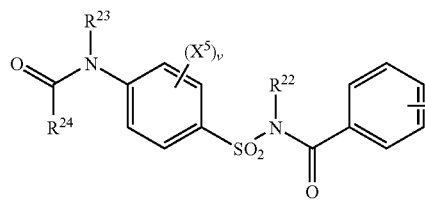

a compound of formula (IIe)

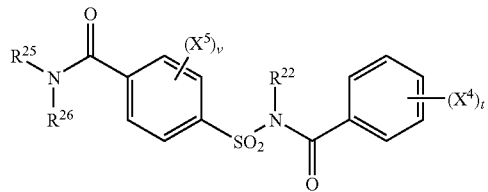

where t represents 0, 1, 2, 3, 4 or 5, v represents 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, C)-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

8. A pesticide, herbicide or fungicide composition comprising at least one compound of formula (I) according to claim 1.

9. A method for controlling animal pests, unwanted vegetation, or fungi, comprising contacting said pests, vegetation, fungi or their habitat with a compound of formula (I) according to claim 1.

10. A process of preparing a pesticide, herbicide or fungicide composition, comprising mixing a compound of formula (I) according to claim 1 with an extender, a surfactant, or a combination thereof.

11. The composition according to claim 7, in which the crop plant compatibility-improving compound is selected from the group consisting of cloquintocet-mexyl, fenchlorazole-ethyl, isoxadifen-ethyl, mefenpyr-diethyl, furilazole, fenclorim, cumyluron, dymron, a compound of formula IIe-5,

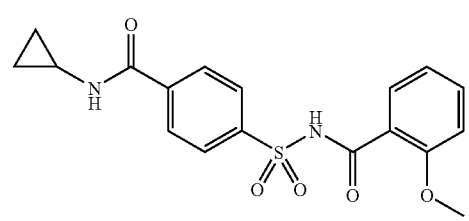

and a compound of formula IIe-11,

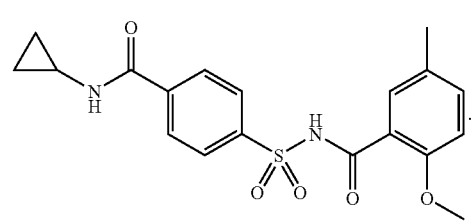

12. The composition according to claim 11, in which the crop plant compatibility-improving compound is mefenpyr-diethyl.

13. The composition according to claim 11, in which the crop plant compatibility-improving compound is the compound IIe-5.

14. A method for controlling unwanted vegetation, comprising contacting said vegetation on or its habitat with a composition according to claim 7.

15. A method for controlling unwanted vegetation, comprising contacting said vegetation or its habitat with a compound of formula (I) according to claim 1 and a crop plant compatibility-improving compound according to claim 7 separately in close temporal succession or as a mixture.

16. A compound of formula (H)

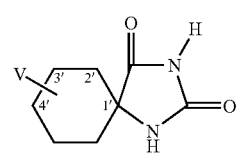

in which
V in the 3' or 4'-position represents

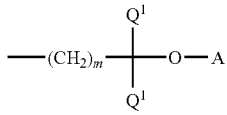

in which
A represents in each case optionally halogen-substituted alkyl, alkenyl, alkynyl, alkoxyalkyl, alkylthioalkyl, saturated or unsaturated, optionally substituted cycloalkylalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl, heteroaryl or heteroarylalkyl,
$Q^1$ and $Q^2$ independently of one another represent hydrogen or alkyl, or
A and $Q^1$ together with the atoms to which they are attached represent a saturated or unsaturated ring which contains at least one heteroatom and is unsubstituted or substituted in the A,Q moiety,
m represents 0, 1 or 2.

17. A compound of formula (I) according to claim 1 in which
W represents hydrogen, fluorine, chlorine, bromine or $C_1$-$C_4$-alkyl,
X represents chlorine, bromine, $C_1$-$C_4$-alkyl, $C_1$-$C_4$-alkoxy, $C_1$-$C_2$-haloalkyl, $C_1$-$C_2$-haloalkoxy or cyano,
Y in the 4-position represents the radical

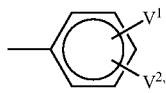

Z represents hydrogen,
$V^1$ represents fluorine, chlorine, $C_1$-$C_4$-alkyl, $C_1$-$C_4$-alkoxy, $C_1$-$C_2$-haloalkyl, $C_1$-$C_2$-haloalkoxy, cyano or nitro,
$V^2$ represents hydrogen, fluorine, chlorine, $C_1$-$C_4$-alkyl, $C_1$-$C_4$-alkoxy or $C_1$-$C_2$-haloalkyl, or
$V^1$ and $V^2$ together also represent —O—$CH_2$—O— or —O—$CF_2$—O—,
A represents hydrogen, represents $C_1$-$C_6$-alkyl, $C_3$-$C_6$-alkenyl, $C_3$-$C_6$-alkynyl, $C_1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$-alkoxy,
B represents hydrogen, $C_1$-$C_2$-alkyl or $C_1$-$C_2$-alkoxy,
D represents NH or oxygen,
$Q^1$, $Q^2$, $Q^3$ and $Q^4$ independently of one another represent hydrogen or methyl, or
A and $Q^1$ together with the atoms to which they are attached represent a saturated 5- to 6-membered ring which is interrupted by at least one oxygen atom and which is optionally substituted by methyl, ethyl, methoxy, ethoxy, methoxymethyl, ethoxymethyl or trifluoromethyl,
m represents 0 or 1,
n represents 1,
G represents hydrogen (a),

 (b)

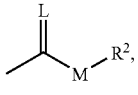 (c)

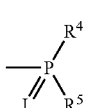 (d)

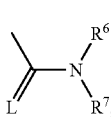 (e)

E or (f)

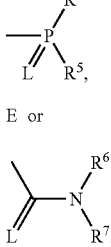 (g)

in which
E represents a metal ion or an ammonium ion,
L represents oxygen or sulphur,
M represents oxygen or sulphur,
$R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine; represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur;
represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;
represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;
represents pyrazolyl, thiazolyl, pyridyl, pyrimidyl, furanyl or thienyl, each of which is optionally mono- to disubstituted by fluorine, chlorine, bromine or $C_1$-$C_4$-alkyl;
represents phenoxy-$C_1$-$C_5$-alkyl which is optionally mono- to disubstituted by fluorine, chlorine, bromine or $C_1$-$C_4$-alkyl; or
represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl,
$R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine,
represents $C_3$-$C_7$-cycloalkyl which is optionally mono- to disubstituted by fluorine, chlorine, $C_1$-$C_4$-alkyl or $C_1$-$C_4$-alkoxy; or
represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine; or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine; or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkythio, $C_1$-$C_3$-alkyl or $C_1$-$C_3$-haloalkyl, $R^6$ and $R^7$ independently of one another represent hydrogen; represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine; represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy; or $R^6$ and $R^7$ together represent an optionally $C_1$-$C_4$-alkyl-substituted $C_3$-$C_6$-alkylene radical in which optionally one methylene group is replaced by oxygen or sulphur.

18. A compound of formula (I) according to claim 1 in which

W represents hydrogen, fluorine, chlorine, bromine or $C_1$-$C_4$-alkyl,

X represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 5-position represents the radical

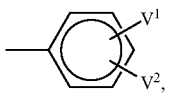

Z in the 4-position represents hydrogen, $V^1$ represents fluorine, chlorine, $C_1$-$C_4$-alkyl, $C_1$-$C_4$-alkoxy, $C_1$-$C_2$-haloalkyl, $C_1$-$C_2$-haloalkoxy, cyano or nitro, $V^2$ represents hydrogen, fluorine, chlorine, $C_1$-$C_4$-alkyl, $C_1$-$C_4$-alkoxy or $C_1$-$C_2$-haloalkyl, or $V^1$ and $V^2$ together likewise represent —O—$CH_2$—O— or —O—$CF_2$—O—, A represents hydrogen, represents $C_1$-$C_6$-alkyl, $C_3$-$C_6$-alkenyl, $C_3$-$C_6$-alkynyl, $C^1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$-alkoxy, B represents hydrogen, $C_1$-$C_2$-alkyl or $C_1$-$C_2$-alkoxy, D represents NH or oxygen, $Q^1$, $Q^2$, $Q^3$ and $Q^4$ independently of one another represent hydrogen or methyl, or A and $Q^1$ together with the atoms to which they are attached represent a saturated 5- to 6-membered ring which is interrupted by at least one oxygen atom and which is optionally substituted by methyl, ethyl, methoxy, ethoxy, methoxymethyl, ethoxymethyl or trifluoromethyl, m represents 0 or 1,
n represents 1,
G represents hydrogen (a), (b)
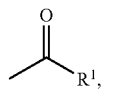

(c)
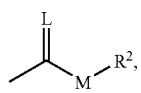

(d)
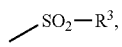

(e)
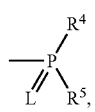

E or (f)

(g)
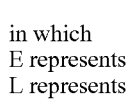

in which
E represents a metal ion or an ammonium ion,
L represents oxygen or sulphur,
M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine; represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur;

represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;

represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;

represents pyrazolyl, thiazolyl, pyridyl, pyrimidyl, fulanyl or thienyl, each of which is optionally mono- to disubstituted by fluorine, chlorine, bromine or $C_1$-$C_4$-alkyl;

represents phenoxy-$C_1$-$C_5$-alkyl which is optionally mono- to disubstituted by fluorine, chlorine, bromine or $C_1$-$C_4$-alkyl; or represents pyridyloxy-$C_1$-$C_5$-alkyl, pyrimidyloxy-$C_1$-$C_5$alkyl or thiazolyloxy -$C_1$-$C_5$-alkyl, each of which is optionally mono- to disubstituted by fluorine, chlorine, bromine, amino or $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- to disubstituted by fluorine, chlorine, $C_1$-$C_4$-alkyl or $C_1$-$C_4$-alkoxy; or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine; or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine; or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another represent hydrogen; represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine; represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy; or $R^6$ and $R^7$ together represent an optionally $C_1$-$C_4$-alkyl-substituted $C_3$-$C_6$-alkylene radical in which optionally one methylene group is replaced by oxygen or sulphur.

19. A compound of formula (I) according to claim 1 in which

W represents hydrogen, $C_1$-$C_4$-alkyl, $C_2$-$C_4$-alkenyl, $C_2$-$C_4$-alkynyl, $C_1$-$C_4$-alkoxy, fluorine, chlorine, bromine or trifluoromethyl, X represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position represents $C_1$-$C_4$-alkyl, Z represents hydrogen, A represents hydrogen, represents $C_1$-$C_6$-alkyl, $C_3$-$C_6$-alkenyl, $C_3$-$C_6$-alkynyl, $C_1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$alkoxy, B represents hydrogen, $C_1$-$C_2$-alkyl or $C_1$-$C_2$-alkoxy, D represents NH or oxygen, $Q^1$, $Q^2$, $Q^3$ and $Q^4$ independently of one another represent hydrogen or methyl, or A and $Q^1$ together with the atoms to which they are attached represent a saturated 5- to 6-membered ring which is interrupted by at least one oxygen atom and which is optionally substituted by methyl, ethyl, methoxy, ethoxy, methoxymethyl, ethoxymethyl or trifluoromethyl, m represents 0 or 1, n represents 1, G represents hydrogen (a),

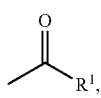
(b)

-continued

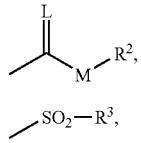
(c)

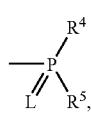
(d)

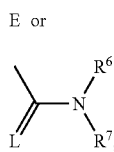
(e)

E or
(f)

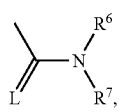
(g)

in which

E represents a metal ion or an ammonium ion,

L represents oxygen or sulphur

M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine; represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur;

represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;

represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;

represents pyrazolyl, thiazolyl, pyridyl, pyrimidyl, furanyl or thienyl, each of which is optionally mono- to disubstituted by fluorine, chlorine, bromine or $C_1$-$C_4$-alkyl;

represents phenoxy-$C_1$-$C_5$-alkyl which is optionally mono- to disubstituted by fluorine, chlorine, bromine or $C_1$-$C_4$-alkyl; or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- to disubstituted by fluorine, chlorine, $C_1$-$C_4$-alkyl or $C_1$-$C_4$-alkoxy; or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine; or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine; or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another represent hydrogen; represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine; represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy; or $R^6$ and $R^7$ together represent an optionally $C_1$-$C_4$-alkyl-substituted $C_3$-$C_6$-alkylene radical in which optionally one methylene group is replaced by oxygen or sulphur.

20. A compound of formula (I) according to claim 1 in which

W represents hydrogen, fluorine, chlorine, bromine, $C_1$-$C_4$-alkyl or $C_1$-$C_4$-alkoxy, X represents chlorine, bromine, iodine, $C_1$-$C_4$-alkyl, $C_1$-$C_4$-alkoxy, $C_1$-$C_2$-haloalkyl, $C_1$-$C_2$-haloalkoxy or cyano, Y in the 4-position represents hydrogen,

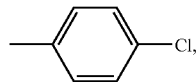

chlorine, bromine, iodine, $C_1$-$C_4$-alkyl, $C_1$-$C_2$-haloalkyl or $C_1$-$C_2$-haloalkoxy, Z in the 3- or 5-position represents fluorine, chlorine, bromine, iodine, $C_1$-$C_4$-alkyl, $C_1$-$C_2$-haloalkyl, $C_1$-$C_4$-alkoxy or $C_1$-$C_2$-haloalkoxy, A represents hydrogen, represents $C_1$-$C_6$-alkyl, $C_3$-$C_6$-alkenyl, $C_3$-$C_6$-alkynyl, $C_1$-$C_4$-alkoxy-$C_1$-$C_2$-alkyl, each of which is optionally mono- to trisubstituted by fluorine or chlorine, represents $C_3$-$C_6$-cycloalkyl-$C_1$-$C_2$-alkyl which is optionally mono- to disubstituted by fluorine, chlorine, $C_1$-$C_2$-alkyl or $C_1$-$C_2$-alkoxy, B represents hydrogen, $C_1$-$C_2$-alkyl or $C_1$-$C_2$-alkoxy, D represents NH or oxygen, $Q^1$, $Q^2$, $Q^3$ and $Q^4$ independently of one another represent hydrogen or methyl, or A and $Q^1$ together with the atoms to which they are attached represent a saturated 5- to 6-membered ring which is interrupted by at least one oxygen atom and which is optionally substituted by methyl, ethyl, methoxy, ethoxy, methoxymethyl, ethoxymethyl or trifluoromethyl, m represents 0 or 1, n represents 1, G represents hydrogen (a),

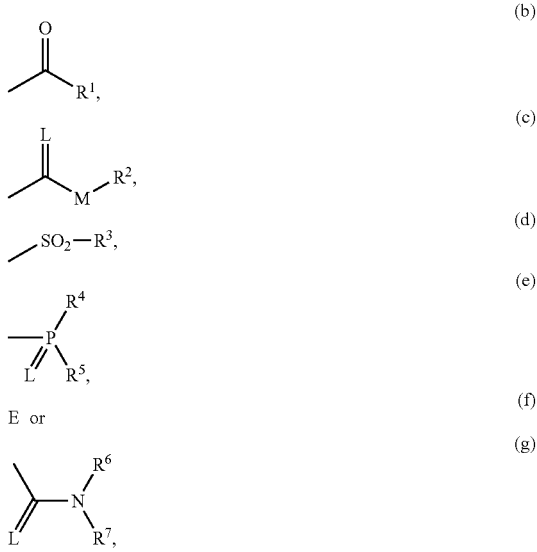

in which

E represents a metal ion or an ammonium ion,

L represents oxygen or sulphur,

M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_3$-$C_4$-alkyl or poly-$C_1$-$C_6$-alkoxy-$C_1$-$C_4$-alkyl, each of which is optionally mono- to trisubstituted by fluorine or chlorine; represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulphur;

represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl;

represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy;

represents pyrazolyl, thiazolyl, pyridyl, pyrimidyl, furanyl or thienyl, each of which is optionally mono- to disubstituted by fluorine, chlorine, bromine or $C_1$-$C_4$-alkyl;

represents phenoxy-$C_1$-$C_5$-alkyl which is optionally mono- to disubstituted by fluorine, chlorine, bromine or $C_1$-$C_4$-alkyl; or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- to disubstituted by fluorine, chlorine, $C_1$-$C_4$-alkyl or $C_1$-$C_4$-alkoxy; or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine; or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine; or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another represent hydrogen; represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine; represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy; or $R^6$ and $R^7$ together represent an optionally $C_1$-$C_4$-alkyl-substituted $C_3$-$C_6$-alkylene radical in which optionally one methylene group is replaced by oxygen or sulphur.

21. A compound of formula (I) according to claim 1 in which

W represents hydrogen, chlorine, bromine, methyl or ethyl,

X represents chlorine, bromine, methyl, ethyl, propyl, methoxy, trifluoromethyl, difluoromethoxy, trifluoromethoxy or cyano, Y in the 4-position represents the radical

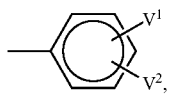

Z represents hydrogen, $V^1$ represents fluorine, chlorine, methyl, methoxy, trifluoromethyl, trifluoromethoxy or cyano, $V^2$ represents hydrogen, fluorine, chlorine, methyl, methoxy or trifluoromethyl, A represents hydrogen, represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine; or represents cyclopropylmethyl, cyclopentylmethyl or cyclohexylmethyl, B represents hydrogen, D represents NH or oxygen, $Q^1$, $Q^2$, $Q^3$ and $Q^4$ represent hydrogen, or A and $Q^1$ together with the atoms to which they are attached represent a saturated 5- to 6-membered ring which is interrupted by at least one oxygen atom and is optionally substituted by methyl or ethyl, m represents 0 or 1, n represents 1, G represents hydrogen (a),

(b)

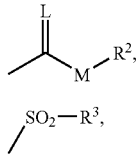
(c)

(d)

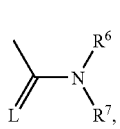
(e)

E or
(f)

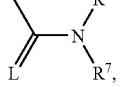
(g)

in which

E represents a metal ion or an ammonium ion,

L represents oxygen or sulphur, and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;

represents phenyl which is optionally mono- to disubstituted by fluorine, chlorine, bromine, cyano, nitro, methyl, ethyl, n-propyl, iso-propyl, methoxy, ethoxy, trifluoromethyl or trifluoromethoxy; or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;

represents cyclopentyl or cyclohexyl;

or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio; or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl; represent phenyl which is optionally mono- to disubstituted by fluorine, chlorine, bromine, methyl, methoxy or trifluoromethyl; or $R^6$ and $R^7$ together represent a $C_5$-$C_6$-alky- 22. A compound of formula (I) according to claim 1 in which W represents hydrogen, chlorine or methyl, X represents chlorine, methyl, trifluoromethyl, methoxy, difluoromethoxy, trifluoromethoxy or cyano, Y in the 5-position represents the radical

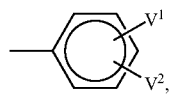

Z in the 4-position represents hydrogen, $V^1$ represents fluorine, chlorine, methyl, methoxy, trifluoromethyl, trifluoromethoxy or cyano, $V^2$ represents hydrogen, fluorine, chlorine, methyl, methoxy or trifluoromethyl, A represents hydrogen, represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine; or represents cyclopropylmethyl, cyclopentylmethyl or cyclohexylmethyl, B represents hydrogen, D represents NH or oxygen, $Q^1$, $Q^2$, $Q^3$ and $Q^4$ represent hydrogen, or A and $Q^1$ together with the atoms to which they are attached represent a saturated 5- to 6-membered ring which is interrupted by at least one oxygen atom and is optionally substituted by methyl or ethyl, m represents 0 or 1, n represents 1, G represents hydrogen (a),

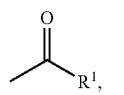 (b)

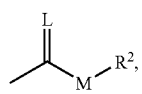 (c)

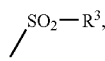 (d)

 (e)

E or (f)

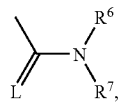 (g)

in which

E represents a metal ion or an ammonium ion,

L represents oxygen or sulphur, and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;

represents phenyl which is optionally mono- to disubstituted by fluorine, chlorine, bromine, cyano, nitro, methyl, ethyl, n-propyl, iso-propyl, methoxy, ethoxy, trifluoromethyl or trifluoromethoxy; or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;

represents cyclopentyl or cyclohexyl;

or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio; or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl; represent phenyl which is optionally mono- to disubstituted by fluorine, chlorine, bromine, methyl, methoxy or trifluoromethyl; or $R^6$ and $R^7$ together represent a $C_5$-$C_6$-alkylene radical in which optionally one methylene group is replaced by oxygen or sulphur.

23. A compound of formula (I) according to claim 1 in which

W represents hydrogen, methyl, ethyl, methoxy, ethoxy, chlorine or bromine,

X represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position represents methyl or ethyl, Z represents hydrogen, A represents hydrogen, represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine; or represents cyclopropylmethyl, cyclopentylmethyl or cyclohexylmethyl, B represents hydrogen, D represents NH or oxygen, $Q^1$, $Q^2$, $Q^3$ and $Q^4$ represent hydrogen, or A and $Q^1$ together with the atoms to which they are attached represent a saturated 5- to 6-membered ring which is interrupted by at least one oxygen atom and is optionally substituted by methyl or ethyl, m represents 0 or 1, n represents 1, G represents hydrogen (a),

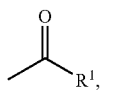 (b)

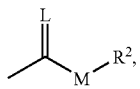 (c)

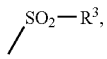 (d)

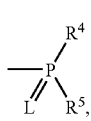 (e)

E or (f)

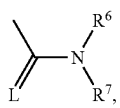 (g)

in which

E represents a metal ion or an ammonium ion,

L represents oxygen or sulphur, and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;

represents phenyl which is optionally mono- to disubstituted by fluorine, chlorine, bromine, cyano, nitro, methyl, ethyl, n-propyl, iso-propyl, methoxy, ethoxy, trifluoromethyl or trifluoromethoxy; or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;

represents cyclopentyl or cyclohexyl;

or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio; or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$alkoxy, $C_3$-$C_4$-alkenyl or $C_1$-$C_4$-alkoxy-$C_2$-$C_4$-alkyl; represent phenyl which is optionally mono- to disubstituted by fluorine, chlorine, bromine, methyl, methoxy or trifluoromethyl; or $R^6$ and $R^7$ together represent a $C_5$-$C_6$-alkylene radical in which optionally one methylene group is replaced by oxygen or sulphur.

24. A compound of formula (I) according to claim 1 in which

W represents hydrogen, chlorine, bromine, methyl or ethyl,

X represents chlorine, bromine, iodine, methyl, ethyl, methoxy, trifluoromethyl, difluoromethoxy or trifluoromethoxy, Y in the 4-position represents hydrogen,

chlorine, bromine, methyl or ethyl,

Z in the 3- or 5-position represents fluorine, chlorine, bromine, iodine, methyl, ethyl, trifluoromethyl or trifluoromethoxy, A represents hydrogen, represents $C_1$-$C_4$-alkyl, $C_3$-$C_4$-alkenyl, $C_3$-$C_4$-alkynyl or $C_1$-$C_2$-alkoxy-$C_1$-$C_2$-alkyl, each of which is optionally mono- to trisubstituted by fluorine; or represents cyclopropylmethyl, cyclopentylmethyl or cyclohexylmethyl, B represents hydrogen, D represents NH or oxygen, $Q^1$, $Q^2$, $Q^3$ and $Q^4$ represent hydrogen, or A and $Q^1$ together with the atoms to which they are attached represent a saturated 5- to 6-membered ring which is interrupted by at least one oxygen atom and is optionally substituted by methyl or ethyl, m represents 0 or 1, n represents 1, G represents hydrogen (a),

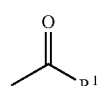 (b)

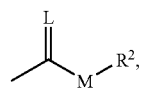 (c)

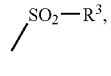 (d)

 (e)

E or (f)

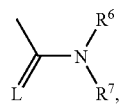 (g)

in which

E represents a metal ion or an ammonium ion,

L represents oxygen or sulphur, and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine; represents $C_3$-$C_6$-cycloalkyl which is optionally monosubstituted by fluorine, chlorine, methyl, ethyl or methoxy;

represents phenyl which is optionally mono- to disubstituted by fluorine, chlorine, bromine, cyano, nitro, methyl, ethyl, n-propyl, iso-propyl, methoxy, ethoxy, trifluoromethyl or trifluoromethoxy; or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine;

represents cyclopentyl or cyclohexyl;

or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine; or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio; or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl; represent phenyl which is optionally mono- to disubstituted by fluorine, chlorine, bromine, methyl, methoxy or trifluoromethyl; or $R^6$ and $R^2$ together represent a $C_5$-$C_6$-alkylene radical in which optionally one methylene group is replaced by oxygen or sulphur.

25. A compound of formula (I) according to claim 1 in which

W represents hydrogen or methyl,
X represents chlorine or methyl,
Y in the 5-position represents

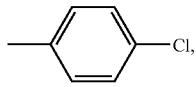

Z in the 4-position represents hydrogen,
A represents $C_1$-$C_4$-alkyl,
B represents hydrogen,
D represents NH or oxygen,
$Q^1$, $Q^2$, $Q^3$ and $Q^4$ represent hydrogen,
m represents 0 or 1,
n represents 1,
G represents hydrogen (a)

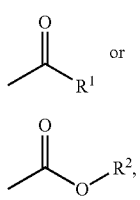

in which
$R^1$ represents $C_1$-$C_{10}$-alkyl, $C_1$-$C_4$-alkoxy-$C_1$-$C_2$-alkyl or cyclopropyl,
$R^2$ represents $C_1$-$C_{10}$-alkyl or benzyl.

26. A compound of formula (I) according to claim 1 in which

W represents methyl, ethyl or methoxy,
X represents chlorine, bromine, methyl, ethyl or methoxy,
Y in the 4-position represents methyl,
Z represents hydrogen,
A represents $C_1$-$C_4$-alkyl,
B represents hydrogen,
D represents NH or oxygen,
$Q^1$, $Q^2$, $Q^3$ and $Q^4$ represent hydrogen,
m represents 0 or 1,
n represents 1,
G represents hydrogen (a),

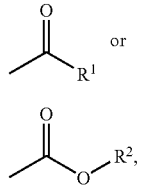

in which
$R^1$ represents $C_1$-$C_{10}$-alkyl, $C_1$-$C_4$-alkoxy-$C_1$-$C_2$-alkyl or cyclopropyl,
$R^2$ represents $C_1$-$C_{10}$-alkyl or benzyl.

27. A compound of formula (I) according to claim 1 in which,

W represents hydrogen or methyl,
X represents bromine, methyl or methoxy,
Y in the 4-position represents

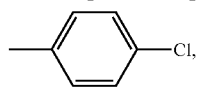

hydrogen, chlorine or methyl,
Z in the 3- or 5-position represents methyl,
A represents $C_1$-$C_4$-alkyl,
B represents hydrogen,
D represents NH or oxygen,
$Q^1$, $Q^2$, $Q^3$ and $Q^4$ represent hydrogen,
m represents 0 or 1,
n represents 1,
G represents hydrogen (a),

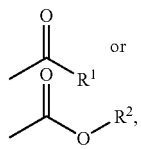

in which
$R^1$ represents $C_1$-$C_{10}$-alkyl, $C_1$-$C_4$-alkoxy-$C_1$-$C_2$-alkyl or cyclopropyl,
$R^2$ represents $C_1$-$C_{10}$-alkyl or benzyl.

* * * * *